(12) United States Patent
Weck et al.

(10) Patent No.: US 11,291,620 B2
(45) Date of Patent: Apr. 5, 2022

(54) AVOBENZONE-DENDRIMER CONJUGATES

(71) Applicant: NEW YORK UNIVERSITY, New York, NY (US)

(72) Inventors: Marcus Weck, New York, NY (US); Elizabeth Anne Kaufman, West Harrison, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/977,340

(22) PCT Filed: Mar. 8, 2019

(86) PCT No.: PCT/US2019/021336
§ 371 (c)(1),
(2) Date: Sep. 1, 2020

(87) PCT Pub. No.: WO2019/173705
PCT Pub. Date: Sep. 12, 2019

(65) Prior Publication Data
US 2021/0100733 A1    Apr. 8, 2021

Related U.S. Application Data

(60) Provisional application No. 62/640,558, filed on Mar. 8, 2018.

(51) Int. Cl.
*A61K 8/88* (2006.01)
*A61K 8/35* (2006.01)
*A61Q 17/04* (2006.01)
*C08F 283/00* (2006.01)

(52) U.S. Cl.
CPC .............. *A61K 8/88* (2013.01); *A61K 8/35* (2013.01); *A61Q 17/04* (2013.01); *C08F 283/00* (2013.01)

(58) Field of Classification Search
CPC ... A61K 8/35; A61K 8/88; A61K 8/42; C07K 7/02; A61Q 17/04; C08F 283/00
See application file for complete search history.

(56) References Cited

U.S. PATENT DOCUMENTS

| | | |
|---|---|---|
| 8,377,871 B2 | 2/2013 | Kallenbach et al. |
| 9,079,937 B2 | 7/2015 | Kallenbach et al. |
| 9,125,829 B2 | 9/2015 | Bonda et al. |
| 2011/0217375 A1 | 9/2011 | Kallenbach et al. |
| 2013/0252880 A1 | 9/2013 | Kallenbach et al. |
| 2014/0050681 A1 | 2/2014 | Bonda et al. |
| 2014/0170090 A1 | 6/2014 | Thaggard |
| 2016/0120785 A1 | 5/2016 | Halpern Chirch et al. |

OTHER PUBLICATIONS

PCT/2019021336, International Search Report and Written Opinion (dated May 8, 2019).
PCT/US2019/021336, International Preliminary Report on Patentability (dated Sep. 17, 2020).

*Primary Examiner* — Nannette Holloman
(74) *Attorney, Agent, or Firm* — Troutman Pepper Hamilton Sanders LLP (Rochester)

(57) ABSTRACT

The present invention relates to avobenzone-dendrimer conjugates comprising: a polyamide dendrimer conjugated with 1 to 18 units of avobenzone. Also disclosed are sunscreen formulations comprising an avobenzone-dendrimer conjugate and a dermatologically acceptable vehicle.

5 Claims, 60 Drawing Sheets

AVOBENZONE-DENDRIMER CONJUGATES

This application is a national stage application under 35 U.S.C. § 371 of International Application No. PCT/US2019/021336, filed Mar. 8, 2019, which claims priority benefit of U.S. Provisional Application No. 62/640,558, filed Mar. 8, 2018, each of which is hereby incorporated by reference in its entirety.

FIELD OF THE INVENTION

The present invention relates to the avobenzone-dendrimer conjugates.

BACKGROUND OF THE INVENTION

Skin cancer affects millions of people each year (Siegel et al., "Impact of Eliminating Socioeconomic and Racial Disparities on Premature Cancer Deaths," *CA. Cancer J. Clin.* 61:212-36 (2011); Siegel et al., "Cancer Statistics 2013," *CA. Cancer J Clin.* 63:11-30 (2013)). The major cause of skin cancer is UV damage (Butler et al., "Increased Prevalence of Left-Sided Skin Cancers," *J. Am. Academic Dertmatol.* 63:1006-10 (2010)), which is easily avoidable through the use of sunscreen (Marionnet et al., "A Broad Spectrum Sunscreen Prevents UVA Radiation-Induced Gene Expression in Reconstructed Skin in Vitro and in Human Skin in Vivo," *Exp. Dermatol.* 20:477-82 (2011); Diffey, "A Method for Broad Spectrum Classification of Sunscreens," *Ind. J. Cosmet. Sci.* 16:47-52 (1994)). Sunscreen has been shown to drastically decrease UV damage to the skin (Damian et al., "Broad-Spectrum Sunscreens Provide Greater Protection Against Ultraviolet-Radiation-Induced Suppression of Contact Hypersenetivity to a Recall Antigen in Humans," *J. Invest. Dermatol.* 109:146-51 (1997)). UV rays are generally considered to fall into two categories, UV-A (315-400 nm), responsible for symptomatic skin aging, and UV-B (280-315 nm), responsible for skin cancer (Dumaz et al., "The Role of UV-B Light in Skin Carcinogenesis Through the Analysis of p53 Mutations in Squamous Cell Carcinomas of Hairless Mice," *Carcinogenesis* 18:897-904 (1997); Dillon "UV-B as a Pro-Aging an Pro-Cataract Factor," *Doc. Opthalmol.* 88:339-44 (1995); Armstrong et al, "Sun Exposure and Skin Cancer," *Australas. J. Dermatology* 38:S1-S6 (1997)) Both types of radiation cause irreparable damage to the skin (Smith et al., "Alterations in Human Dermal Connective Tissue with Age and Chronic Sun Damage," *J. Invest. Dermatol.* 347-50 (1962); Davis, "Sun and Active Patients," *Phys. Sports Med.* 28:79-85 (2016)). Ideal sun care products have a broad absorbance across the UV spectrum, are transparent on the skin, have good film formation, are light stable, and have pleasant rheological properties (Semenzato et al., "Rheological Characterization of Sunscreen Emulsions," *Prog. Trends Rheol.* 593-94 (1998); Gupta, "Evaluation of Sunscreen Agents," *J. Soc. Cos. Chem.* 18:143-74 (1967)).

Avobenzone, a component in many sunscreens, is the only FDA-approved UVA-A filter that does not sensitize the skin and absorbs in the low energy UV range (Hexsel et al., "Current Sunscreen Issues: 2007 Food and Drug Administration Sunscreen Labelling Recommendations and Combination Sunscreen/Insect Repellent Products," *J. Am. Acad. Dermatol.* 59:316-23 (2008); Beasley et al., "Characterization of the UVA Protection Provided by Avobenzone, Zinc Oxide, Titanium Dioxide in Broad-Spectrum Sunscreen Products," *Am. J. Clin. Dermatol.* 11:414-21 (2010)). Despite widespread use of avobenzone, the compound has several inherent drawbacks, notably, its instability to light exposure, which reduces its longevity (Aspée et al., "Transient Enol Isomers of Dibenzomethane and Avobenzone as Efficient Hydrogen Donors Toward a Nitroxide Pre-Flourescent Probe," *J. Phoochem. Photobiol.* 83:481-85 (2007); Mturi et al., "Photostability of the Sunscreen Agent 4-Tert-butyl-4'-methoxydibenzoylmethane (Avobenzone) in Solvents of Different Polarity and Proticity," *J. Photochem. Photobiol.* 200:410-20 (2008); Afonso et al., "Photodegradation of Avobenzone: Stabilization Effect of Antioxidants," *J. Photochem. Photobiol. B.* 140:36-40 (2014); Sayre et al., "Unexpected Photolysis of the Sunscreen Octinoxate in the Presence of the Sunscreen Avobenzone," *J. Photochem. Photobiol.* 81:452-56 (2005)). After exposure to UVA irradiation the enol undergoes either photoisomerization to the diketone or cis/trans isomerization, eventually resulting in homolytic cleavage of the carbon-carbon bond (FIG. 1).

The present invention is directed to overcoming these and other deficiencies in the art.

SUMMARY OF THE INVENTION

One aspect of the present invention relates to an avobenzone-dendrimer conjugate comprising: a polyamide dendrimer conjugated with 1 to 18 units of avobenzone.

In at least one embodiment, the avobenzone-dendrimer conjugate has from 1 to 6 units of avobenzone and has a formula selected from the group consisting of:

(a) Formula IA:

wherein:

A is an amide dendrimer core;

each B is, independently, a moiety of formula

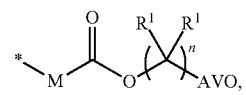

wherein:

*- is the point of attachment to A;

M is optionally present and, if present, is an aromatic or aliphatic moiety;

each $R^1$ is selected from the group consisting of H and $C_{1-3}$ alkyl;

each AVO is, independently, a capping group or avobenzone, wherein at least one AVO is avobenzone; and n is an integer from 1 to 30; and (b) Formula IB:

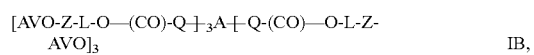

wherein:

A is an amide dendrimer core;

Q is optionally present and, if present, is an aromatic or aliphatic moiety;

each L is a linker;

each Z is optionally present and, if present, is a spacer; and each AVO is, independently, a capping group or avobenzone.

In at least one embodiment, the avobenzone-dendrimer conjugate has a formula of Formula II:

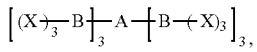

wherein:
A is an amide dendrimer core;
each B is, independently, a moiety of formula

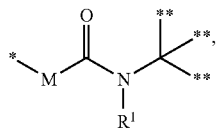

wherein:
*- is the point of attachment to A;
** is the point of attachment to X;
M is an aromatic or aliphatic moiety; and
each $R^1$ is selected from the group consisting of H and $C_{1-3}$ alkyl; and
each X is, independently, a moiety of formula ***-Q-(CO)—O-L-Z-AVO, wherein:
***- is the point of attachment to B;
Q is optionally present and, if present, is an aromatic or aliphatic moiety;
each L is a linker;
each Z is optionally present and, if present, is a spacer; and
each AVO is, independently, a capping group or avobenzone.

In at least one embodiment, the avobenzone-dendrimer conjugate has from 1 to 16 units of avobenzone and has a formula of Formula III:

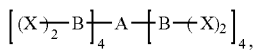

wherein:
A is an amide dendrimer core;
each B is, independently, a moiety of formula

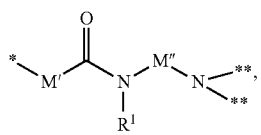

wherein:
*- is the point of attachment to A;
** is the point of attachment to X;
each M' and M" are, independently, an aromatic or aliphatic moiety; and
each $R^1$ is selected from the group consisting of H and $C_{1-3}$ alkyl; and each X is, independently, a moiety of formula ***-Q-(CO)—O-L-Z-AVO, wherein:
***- is the point of attachment to B;
Q is optionally present and, if present, is an aromatic or aliphatic moiety;
each L is a linker;
each Z is optionally present and, if present, is a spacer; and
each AVO is, independently, a capping group or avobenzone.

Another aspect of the present invention is sunscreen formulations. These sunscreen formulations comprise an avobenzone-dendrimer conjugate as described herein and a dermatologically acceptable vehicle.

Active ingredients in cosmetics have a wide array of applications from UV filters to antioxidants. These molecules can also have undesirable reactivity. Avobenzone is a photo-unstable ingredient used in many sunscreen formulations to slow UV-A induced skin damage. Described herein is the synthesis of avobenzone-functionalized dendrimers. The described ligation strategy can stabilize the avobenzone and impart better UV-activity.

DETAILED DESCRIPTION OF THE INVENTION

Figure 1:
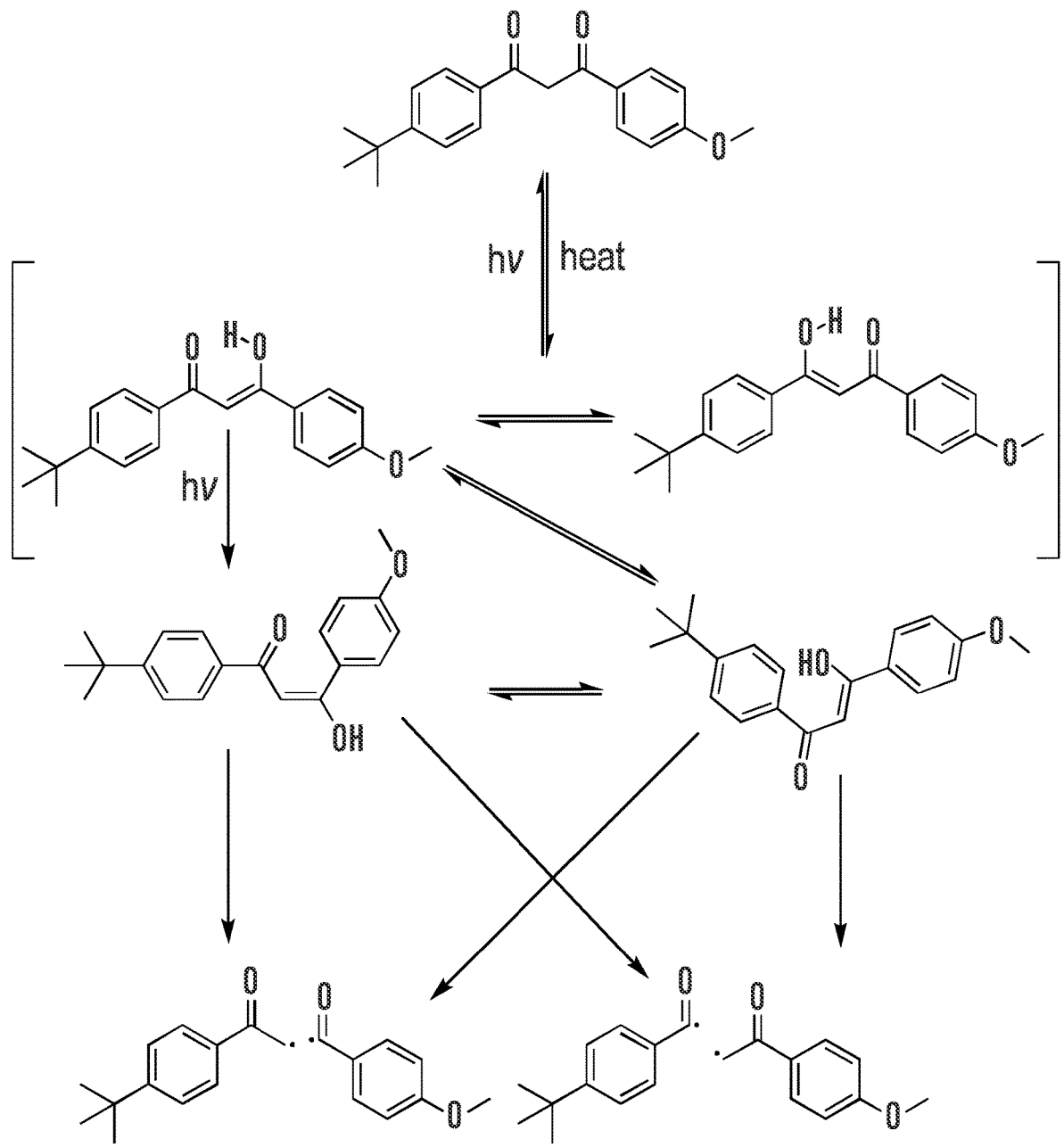
FIG. 1 is a schematic diagram showing photoisomerization and photodegradation of avobenzone.

The present invention relates generally to avobenzone-dendrimer conjugates. Preferences and options for a given aspect, feature, embodiment, or parameter of the invention should, unless the context indicates otherwise, be regarded as having been disclosed in combination with any and all preferences and options for all other aspects, features, embodiments, and parameters of the invention.

Dendrimers have been extensively studied as vehicles for the delivery of therapeutics or as carriers for in vivo imaging (Lee et al., *Nat. Biotech.* 23(12):1517-26 (2005); Esfand & Tomalia, *Drug Discov. Today* 6(8):427-36 (2001); Sadler & Tam, *Rev. Mol. Biotechnol.* 90:195-229 (2002); Cloninger, *Curr. Opin. Chem. Biol.* 6:742-48 (2002); Niederhafner et al., *J. Peptide Sci.* 11:757-88 (2005); Tekade et al., *Chem. Rev.* 109(1):49-87 (2009), each of which is hereby incorporated by reference in its entirety). Dendrimers are highly branched macromolecules with well defined three-dimensional architectures (GEORGE R. NEWKOME ET AL, DENDRIMERS AND DENDRONS: CONCEPTS, SYNTHESIS, APPLICATIONS (2001), which is hereby incorporated by reference in its entirety). The appeal of dendrimers lies in their unique perfectly branched architectures, which affords them different properties than corresponding linear polymers of the same composition and molecular weights (Lee et al., *Nat. Biotech.* 23(12):1517-26 (2005), which is hereby incorporated by reference in its entirety). As dendrimers increase in generation, they exponentially increase the number of termini, while only linearly increasing in radius; thus, the termini become more densely packed giving the entire structure a globular shape, where the termini radiate outwards from a central core.

One aspect of the present invention relates to an avobenzone-dendrimer conjugate comprising: a polyamide dendrimer conjugated with 1 to 18 units (i.e., 1, 2, 3, 4, 5, 6, 7, 8, 9, 10, 11, 12, 13, 14, 15, 16, 17, 18, 1-2, 1-3, 1-4, 1-5, 1-6, 1-7, 1-8, 1-9, 1-10, 1-11, 1-12, 1-13, 1-14, 1-15, 1-16, 1-17, 1-18, 2-3, 2-4, 2-5, 2-6, 2-7, 2-8, 2-9, 2-10, 2-11, 2-12, 2-13, 2-14, 2-15, 2-16, 2-17, 2-18, 3-4, 3-5, 3-6, 3-7, 3-8, 3-9, 3-10, 3-11, 3-12, 3-13, 3-14, 3-15, 3-16, 3-17, 3-18, 4-5, 4-6, 4-7, 4-8, 4-9, 4-10, 4-11, 4-12, 4-13, 4-14, 4-15, 4-16, 4-17, 4-18, 5-6, 5-7, 5-8, 5-9, 5-10, 5-11, 5-12, 5-13, 5-14, 5-15, 5-16, 5-17, 5-18, 6-7, 6-8, 6-9, 6-10, 6-11, 6-12, 6-13, 6-14, 6-15, 6-16, 6-17, 6-18, 7-8, 7-9, 7-10, 7-11, 7-12, 7-13, 7-14, 7-15, 7-16, 7-17, 7-18, 8-9, 8-10, 8-11, 8-12, 8-13, 8-14, 8-15, 8-16, 8-17, 8-18, 9-10, 9-11, 9-12, 9-13, 9-14, 9-15, 9-16, 9-17, 9-18, 10-11, 10-12, 10-13, 10-14, 10-15, 10-16, 10-17, 10-18, 11-12, 11-13, 11-14, 11-15, 11-16, 11-17, 11-18, 12-13, 12-14, 12-15, 12-16, 12-17, 12-18, 13-14, 13-15, 13-16, 13-17, 13-18, 14-15, 14-16, 14-17, 14-18, 15-16, 15-17, 15-18, 16-17, 16-18, or 17-18 units) of avobenzone. Preferably, the conjugate has 6, 16, or 18 terminal branches.

In at least one embodiment of the avobenzone-dendrimer conjugate, each unit of avobenzone is conjugated to the dendrimer via a linker and, optionally, a spacer.

In at least one embodiment, the avobenzone-dendrimer conjugate has 6 terminal branches and 1 to 6 units (i.e., 1, 2, 3, 4, 5, 6, 1-2, 1-3, 1-4, 1-5, 1-6, 2-3, 2-4, 2-5, 2-6, 3-4, 3-5, 3-6, 4-5, 4-6, or 5-6 units) of avobenzone. Such conjugates include, for example, avobenzone-dendrimer conjugates of Formula IA and Formula IB, as follows.

(a) Formula IA:

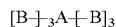

IA wherein:
A is an amide dendrimer core;
each B is, independently, a moiety of formula

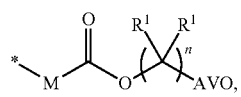

wherein:
*- is the point of attachment to A;
M is optionally present and, if present, is an aromatic or aliphatic moiety;
each $R^1$ is selected from the group consisting of H and $C_{1-3}$ alkyl;
each AVO is, independently, a capping group or avobenzone, wherein at least one AVO is avobenzone; and
n is an integer from 1 to 30.

(b) Formula IB:

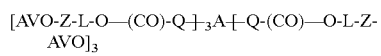

IB, wherein:
A is an amide dendrimer core;
Q is optionally present and, if present, is an aromatic or aliphatic moiety;
each L is a linker;
each Z is optionally present and, if present, is a spacer; and
each AVO is, independently, a capping group or avobenzone.

In at least one embodiment, the avobenzone-dendrimer conjugate has 18 terminal branches and 1 to 18 units (i.e., 1, 2, 3, 4, 5, 6, 7, 8, 9, 10, 11, 12, 13, 14, 15, 16, 17, 18, 1-2, 1-3, 1-4, 1-5, 16, 1-7, 1-8, 1-9, 1-10, 1-11, 1-12, 1-13, 1-14, 1-15, 1-16, 1-17, 1-18, 2-3, 2-4, 2-5, 2-6, 2-7, 2-8, 2-9, 2-10, 2-11, 2-12, 2-13, 2-14, 2-15, 2-16, 2-17, 2-18, 3-4, 3-5, 3-6, 3-7, 3-8, 3-9, 3-10, 3-11, 3-12, 3-13, 3-14, 3-15, 3-16, 3-17, 3-18, 4-5, 4-6, 4-7, 4-8, 4-9, 4-10, 4-11, 4-12, 4-13, 4-14, 4-15, 4-16, 4-17, 4-18, 5-6, 5-7, 5-8, 5-9, 5-10, 5-11, 5-12, 5-13, 5-14, 5-15, 5-16, 5-17, 5-18, 6-7, 6-8, 6-9, 6-10, 6-11, 6-12, 6-13, 6-14, 6-15, 6-16, 6-17, 6-18, 7-8, 7-9, 7-10, 7-11, 7-12, 7-13, 7-14, 7-15, 7-16, 7-17, 7-18, 8-9, 8-10, 8-11, 8-12, 8-13, 8-14, 8-15, 8-16, 8-17, 8-18, 9-10, 9-11, 9-12, 9-13, 9-14, 9-15, 9-16, 9-17, 9-18, 10-11, 10-12, 10-13, 10-14, 10-15, 10-16, 10-17, 10-18, 11-12, 11-13, 11-14, 11-15, 11-16, 11-17, 11-18, 12-13, 12-14, 12-15, 12-16, 12-17, 12-18, 13-14, 13-15, 13-16, 13-17, 13-18, 14-15, 14-16, 14-17, 14-18, 15-16, 15-17, 15-18, 16-17, 16-18, or 17-18 units) of avobenzone. Such conjugates include, for example, avobenzone-dendrimer conjugates of Formula II:

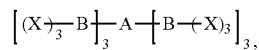

II wherein:
A is an amide dendrimer core;
each B is, independently, a moiety of formula

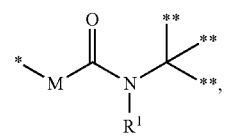

wherein:
*- is the point of attachment to A;
** is the point of attachment to X;
M is an aromatic or aliphatic moiety; and
each $R^1$ is selected from the group consisting of H and $C_{1-3}$ alkyl; and
each X is, independently, a moiety of formula ***-Q-(CO)—O-L-Z-AVO, wherein:
***- is the point of attachment to B;
Q is optionally present and, if present, is an aromatic or aliphatic moiety;
each L is a linker;
each Z is optionally present and, if present, is a spacer; and
each AVO is, independently, a capping group or avobenzone.

In at least one embodiment, the avobenzone-dendrimer conjugate has 16 terminal branches and 1 to 16 units (i.e., 1, 2, 3, 4, 5, 6, 7, 8, 9, 10, 11, 12, 13, 14, 15, 16, 1-2, 1-3, 1-4, 1-5, 1-6, 1-7, 1-8, 1-9, 1-10, 1-11, 1-12, 1-13, 1-14, 1-15, 1-16, 2-3, 2-4, 2-5, 2-6, 2-7, 2-8, 2-9, 2-10, 2-11, 2-12, 2-13, 2-14, 2-15, 2-16, 3-4, 3-5, 3-6, 3-7, 3-8, 3-9, 3-10, 3-11, 3-12, 3-13, 3-14, 3-15, 3-16, 4-5, 4-6, 4-7, 4-8, 4-9, 4-10, 4-11, 4-12, 4-13, 4-14, 4-15, 4-16, 5-6, 5-7, 5-8, 5-9, 5-10, 5-11, 5-12, 5-13, 5-14, 5-15, 5-16, 6-7, 6-8, 6-9, 6-10, 6-11, 6-12, 6-13, 6-14, 6-15, 6-16, 7-8, 7-9, 7-10, 7-11, 7-12, 7-13, 7-14, 7-15, 7-16, 8-9, 8-10, 8-11, 8-12, 8-13, 8-14, 8-15, 8-16, 9-10, 9-11, 9-12, 9-13, 9-14, 9-15, 9-16, 10-11, 10-12, 10-13, 10-14, 10-15, 10-16, 11-12, 11-13, 11-14, 11-15, 11-16, 12-13, 12-14, 12-15, 12-16, 13-14, 13-15, 13-16, 14-15, 14-16, or 15-16 units) of avobenzone. Such conjugates include, for example, avobenzone-dendrimer conjugates of Formula III:

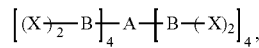

III wherein:
A is an amide dendrimer core;
each B is, independently, a moiety of formula

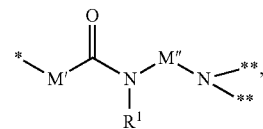

wherein:

*- is the point of attachment to A;

** is the point of attachment to X;

each M' and M" are, independently, an aromatic or aliphatic moiety; and each $R^1$ is selected from the group consisting of H and $C_{1-3}$ alkyl; and each X is, independently, a moiety of formula ***-Q-(CO)—O-L-Z-AVO, wherein:

***- is the point of attachment to B;

Q is optionally present and, if present, is an aromatic or aliphatic moiety;

each L is a linker;

each Z is optionally present and, if present, is a spacer; and each AVO is, independently, a capping group or avobenzone.

AVO in Formula IA, Formula IB, Formula II, and Formula III is an avobenzone molecule or a capping group. As used herein, a capping group is any group that is suitable for terminating a non-functionalized dendron (i.e., a dendron that does not contain an avobenzone molecule). Various capping groups can be used in accordance with the present invention, as will be apparent to the skilled artisan. Suitable capping groups include, without limitation, hydrogen, alkyls, acids (e.g., carboxylic acid), azides, esters, amides, amines, and alcohols. In at least one embodiment, the capping group is functionally inert. Each capping group can be the same or different. (In Examples 1-9, infra, AVO is always avobenzone.)

"A" in Formula IA, Formula IB, Formula II, and Formula III is an amide dendrimer core. Various types of amide dendrimer cores have been described in the art. Suitable cores include those described in Tarallo et al., *Int. J. Nanomed.* 8:521-34 (2013); Carberry et al., *Chem. Eur. J.* 1813678-85 (2012); Jung et al., *Afacromolecules* 44:9075-83 (2011); Ornelas et al., *J. Am. Chem. Soc.* 132:3923-31 (2010); Ornelas et al., *Chem. Commun.* 5710-12 (2009); Goyal et al., *Adv. Synth. Catal.* 350:1816-22 (2008); and Yoon et al., *Org. Lett.* 9:2051-54 (2007), each of which is hereby incorporated by reference in its entirety.

In at least one embodiment of Formula IA, Formula IB, and Formula II, the amide dendrimer core A is a moiety of formula

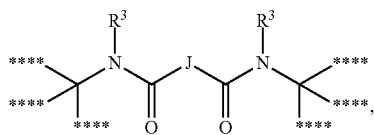

wherein ****- is the point of attachment to B or Q; each $R^3$ is selected from the group consisting of H and $C_{1-11}$ (i.e., $C_1$, $C_2$, $C_3$, $C_4$, $C_5$, $C_6$, $C_7$, $C_8$, $C_9$, $C_{10}$, $C_{11}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{2-3}$, $C_{2-4}$, $C_{2-5}$, $C_{2-6}$, $C_{2-7}$, $C_{2-8}$, $C_{2-9}$, $C_{1-10}$, $C_{2-11}$, $C_{3-4}$, $C_{3-5}$, $C_{3-6}$, $C_{3-7}$, $C_{3-8}$, $C_{3-9}$, $C_{3-10}$, $C_{3-11}$, $C_{4-5}$, $C_{4-6}$, $C_{4-7}$, $C_{4-8}$, $C_{4-9}$, $C_{4-10}$, $C_{4-11}$, $C_{5-6}$, $C_{5-7}$, $C_{5-8}$, $C_{5-9}$, $C_{5-10}$, $C_{5-11}$, $C_{6-7}$, $C_{6-8}$, $C_{6-9}$, $C_{6-10}$, $C_{6-11}$, $C_{7-8}$, $C_{7-9}$, $C_{7-10}$, $C_{7-11}$, $C_{8-9}$, $C_{8-10}$, $C_{8-11}$, $C_{9-10}$, $C_{9-11}$, or $C_{10-11}$) alkyl; and J is an aromatic or aliphatic moiety. Suitable examples include, without limitation:

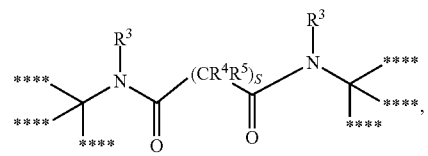

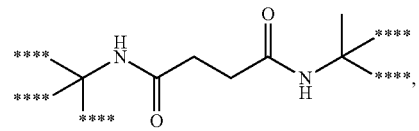

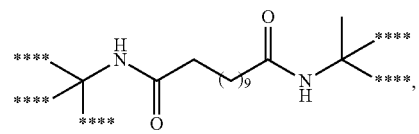

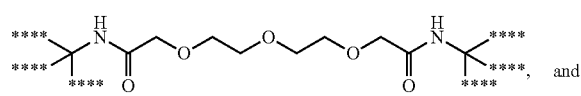

and

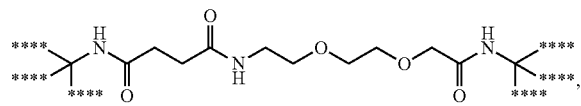

wherein s is 1 to 20 (i.e., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) and each $R^4$ and $R^5$ are independently selected from the group consisting of H, halogen, alkyl, alkenyl, alkynyl, cycloalkyl, hydroxyalkyl, thiol, thioalkyl, alkylthioalkyl, alkoxy, aldehyde, ketone, acid, amine, amide, alcohol, heterocyclyl, aryl, heteroaryl, arylalkyl, and acyl.

In at least one embodiment of Formula III, the amide dendrimer core A is a moiety of formula

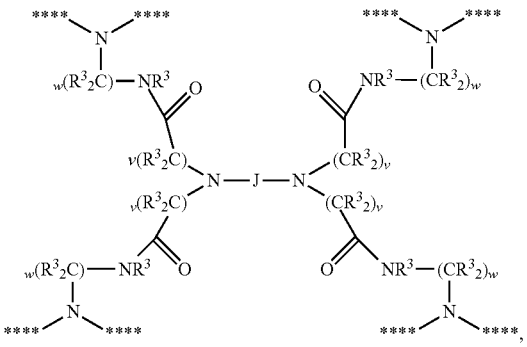

wherein ****- is the point of attachment to B; each $R^3$ is selected from the group consisting of H and $C_{1-11}$ (i.e., $C_1$, $C_2$, $C_3$, $C_4$, $C_5$, $C_6$, $C_7$, $C_8$, $C_9$, $C_{10}$, $C_{11}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{2-3}$, $C_{2-4}$, $C_{2-5}$, $C_{2-6}$, $C_{2-7}$, $C_{2-8}$, $C_{2-9}$, $C_{1-10}$, $C_{2-11}$, $C_{3-4}$, $C_{3-5}$, $C_{3-6}$, $C_{3-7}$, $C_{3-8}$, $C_{3-9}$, $C_{3-10}$, $C_{3-11}$, $C_{4-5}$, $C_{4-6}$, $C_{4-7}$, $C_{4-8}$, $C_{4-9}$, $C_{4-10}$, $C_{4-11}$, $C_{5-6}$, $C_{5-7}$, $C_{5-8}$, $C_{5-9}$, $C_{5-10}$, $C_{5-11}$, $C_{6-7}$, $C_{6-8}$, $C_{6-9}$, $C_{6-10}$, $C_{6-11}$, $C_{7-8}$, $C_{7-9}$, $C_{7-10}$, $C_{7-11}$, $C_{8-9}$, $C_{8-10}$, $C_{8-11}$, $C_{9-10}$, $C_{9-11}$, or $C_{10-11}$) alkyl; each v is independently 2 to 20 (i.e., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20); each w is independently 2 to 20 (i.e., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20); and J is an aromatic or aliphatic moiety. In at least one embodiment, each v is the same; in at least one embodiment, each w is the same; in at least one embodiment, each v is the same and each w is the same. Suitable examples include, without limitation:

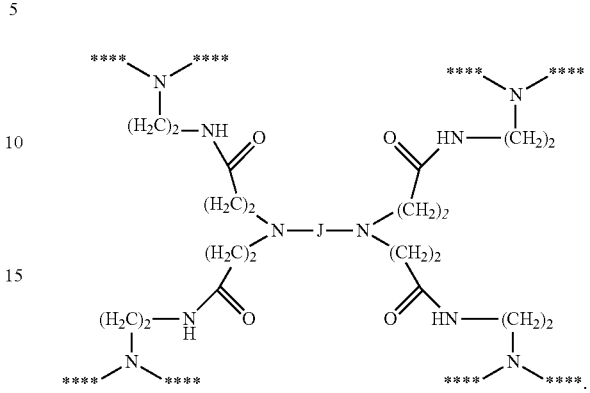

In Formula IA, Formula IB, Formula I, and Formula III, suitable J moieties for use in the amide dendrimer core include, for example, the aromatic and aliphatic moieties described in Tarallo et al., *Int. J. Nanomed.* 8:521-34 (2013); Carberry et al., *Chem. Eur. J.* 1813678-85 (2012); Jung et al., *Macromolecules* 44:9075-83 (2011); Ornelas et al., *J. Am. Chem. Soc.* 132:3923-31 (2010); Ornelas et al., *Chem. Commun.* 5710-12 (2009); Goyal et al., *Adv. Synth. Catal.* 350:1816-22 (2008); and Yoon et al., *Org. Lett.* 9:2051-54 (2007), each of which is hereby incorporated by reference in its entirety.

In at least one embodiment of the avobenzone-dendrimer conjugate of Formula IA, Formula IB, Formula II, and Formula II, J is a moiety of formula $-J^1-J^2-J^3-J^4-J^5-J^6-J^7-J^8-J^9-J^{10}-J^{11}-J^{12}-J^{13}-J^{14}-J^{15}-J^{16}-J^{17}-$; wherein $J^1$, $J^2$, $J^3$, $J^4$, $J^5$, $J^6$, $J^7$, $J^8$, $J^9$, $J^{10}$, $J^{11}$, $J^{12}$, $J^{13}$, $J^{14}$, $J^{15}$, $J^{16}$, and $J^{17}$ are each, independently, absent or selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, C, —C(O)—, O, S, Si, N, NH, and P, wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, C, —C(O)—, O, S, Si, N, NH, and P is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; and with the proviso that at least one of $J^1$, $J^2$, $J^3$, $J^4$, $J^5$, $J^6$, $J^7$, $J^8$, $J^9$, $J^{10}$, $J^{11}$, $J^{12}$, $J^{13}$, $J^{14}$, $J^{15}$, $J^{16}$, and $J^{17}$ is present.

In at least one embodiment of the avobenzone-dendrimer conjugate of Formula IA, Formula IB, Formula II, and Formula III, J is selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$ $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, —C(O)—, —C(O)O—, —O—, —S—, —S(O)—, —S(O)$_2$—, —OP(O)(OH)—, —OP(O)($R^{20}$)—, —OP(OH)$_2$—, —OP($R^{20}$)$_2$—, —NH—, —N($R^{20}$)—, —NHC(O)—, —N($R^{20}$)C(O)—, —Si($R^{21}R^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl; wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, —C(O)—, —C(O)O—, —O—, —S—, —S(O)—, —S(O)$_2$—, —OP(O)(OH)—, —OP(O)($R^{20}$)—, —OP(OH)$_2$—, —OP($R^{20}$)$_2$—, —NH—, —N($R^{20}$)—, —NHC(O)—, —N($R^{20}$)C(O)—, —Si($R^{21}R^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl is optionally substituted from 1 to 10 times with a substituent independently selected at each occurrence from the group consisting of halogen, OH, $C_{1-20}$ alkoxy, and =O; $R^{20}$ is selected from the group consisting of $C_{1-20}$ alkyl, $C_{2-20}$ alkenyl, $C_{2-20}$ alkynyl, $C_{1-20}$ alkoxy, —OH, —SH, —$SC_{1-20}$ alkyl, —COOH, amine, and aryl; and $R^{21}$ and $R^{22}$ are independently selected from the group consisting of $C_{1-20}$ alkyl, $C_{2-20}$ alkenyl, —$OC_{1-20}$ alkyl, amine, —$OSi(C_{1-20}$ alkyl$)_3$, —$OSi(C_{1-20}$ alkyl$)_2(C_{2-20}$ alkenyl), and —$OSi(C_{1-20}$ alkyl)$(C_{2-20}$ alkenyl$)_2$.

In at least one embodiment of the avobenzone-dendrimer conjugate of Formula IA, Formula IB, Formula II, and Formula III, J is an aromatic or aliphatic moiety of formula —$(CR^4R^5)_s$—, wherein s is 1 to 20 (i.e., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) and each $R^4$ and $R^5$ are independently selected from the group consisting of H, halogen, alkyl, alkenyl, alkynyl, cycloalkyl, hydroxyalkyl, thiol, thioalkyl, alkylthioalkyl, alkoxy, aldehyde, ketone, acid, amine, amide, alcohol, heterocyclyl, aryl, heteroaryl, arylalkyl, and acyl. In at least one embodiment, at least one of $R^4$ and $R^5$ is a $C_{1-11}$ alkyl optionally substituted with from 1 to 3 (i.e., 1, 2, 3, 1-2, 1-3, or 2-3) substituents independently selected at each occurrence thereof from $C_{1-11}$ alkyl, halogen, —CN, —$COOR^6$, —$C(O)R^7$, —$OR^8$, —$NR^9R^{10}$, —$S(O)_xR^{11}$, —$SR^{12}$, and aryl; where $R^6, R^7, R^8, R^9, R^{10}, R^{11}$ and $R^{12}$ are independently selected from the group consisting of H, $C_{1-11}$ alkyl, aryl, and heteroaryl; and x is 1 or 2.

In at least one embodiment of the avobenzone-dendrimer conjugate of Formula IA and Formula II, M is a moiety of formula-$M^1$-$M^2$-$M^3$-$M^4$-$M^5$-$M^6$-$M^7$-$M^8$-$M^9$-$M^{10}$-$M^{11}$-$M^{12}$-$M^{13}$-$M^{14}$-$M^{15}$-$M^{16}$-$M^{17}$-; wherein $M^1, M^2, M^3, M^4, M^5, M^6, M^7, M^8, M^9, M^{10}, M^{11}, M^{12}, M^{13}, M^{14}, M^{15}, M^{16}$, and $M^{17}$ are each, independently, absent or selected from the group consisting of $C_{1-20}$ (i.e., $C_1, C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{1-2}, C_{1-3}, C_{1-4}, C_{1-5}, C_{1-6}, C_{1-7}, C_{1-8}, C_{1-9}, C_{1-10}, C_{1-11}, C_{1-12}, C_{1-13}, C_{1-14}, C_{1-15}, C_{1-16}, C_{1-17}, C_{1-18}, C_{1-19}, C_{1-20}, C_{2-3}, C_{2-4}, C_{2-5}, C_{2-6}, C_{2-7}, C_{2-8}, C_{2-9}, C_{2-10}, C_{2-11}, C_{2-12}, C_{2-13}, C_{2-14}, C_{2-15}, C_{2-16}, C_{2-17}, C_{2-18}, C_{2-19}, C_{2-20}, C_{3-4}, C_{3-5}, C_{3-6}, C_{3-7}, C_{3-8}, C_{3-9}, C_{3-10}, C_{3-11}, C_{3-12}, C_{3-13}, C_{3-14}, C_{3-15}, C_{3-16}, C_{3-17}, C_{3-18}, C_{3-19}, C_{3-20}, C_{4-5}, C_{4-6}, C_{4-7}, C_{4-8}, C_{4-9}, C_{4-10}, C_{4-11}, C_{4-12}, C_{4-13}, C_{4-14}, C_{4-15}, C_{4-16}, C_{4-17}, C_{4-18}, C_{4-19}, C_{4-20}, C_{5-6}, C_{5-7}, C_{5-8}, C_{5-9}, C_{5-10}, C_{5-11}, C_{5-12}, C_{5-13}, C_{5-14}, C_{5-15}, C_{5-16}, C_{5-17}, C_{5-18}, C_{5-19}, C_{5-20}, C_{6-7}, C_{6-8}, C_{6-9}, C_{6-10}, C_{6-11}, C_{6-12}, C_{6-13}, C_{6-14}, C_{6-15}, C_{6-16}, C_{6-17}, C_{6-18}, C_{6-19}, C_{6-20}, C_{7-8}, C_{7-9}, C_{7-10}, C_{7-11}, C_{7-12}, C_{7-13}, C_{7-14}, C_{7-15}, C_{7-16}, C_{7-17}, C_{7-18}, C_{7-19}, C_{7-20}, C_{8-9}, C_{8-10}, C_{8-11}, C_{8-12}, C_{8-13}, C_{8-14}, C_{8-15}, C_{8-16}, C_{8-17}, C_{8-18}, C_{8-19}, C_{8-20}, C_{9-10}, C_{9-11}, C_{9-12}, C_{9-13}, C_{9-14}, C_{9-15}, C_{9-16}, C_{9-17}, C_{9-18}, C_{9-19}, C_{9-20}, C_{10-11}, C_{10-12}, C_{10-13}, C_{10-14}, C_{10-15}, C_{10-16}, C_{10-17}, C_{10-18}, C_{10-19}, C_{10-20}, C_{11-12}, C_{11-13}, C_{11-14}, C_{11-15}, C_{11-16}, C_{11-17}, C_{11-18}, C_{11-19}, C_{11-20}, C_{12-13}, C_{12-14}, C_{12-15}, C_{12-16}, C_{12-17}, C_{12-18}, C_{12-19}, C_{12-20}, C_{13-14}, C_{13-15}, C_{13-16}, C_{13-17}, C_{13-18}, C_{13-19}, C_{13-20}, C_{14-15}, C_{14-16}, C_{14-17}, C_{14-18}, C_{14-19}, C_{14-20}, C_{15-16}, C_{15-17}, C_{15-18}, C_{15-19}, C_{15-20}, C_{16-17}, C_{16-18}, C_{16-19}, C_{16-20}, C_{17-18}, C_{17-19}, C_{17-20}, C_{18-19}, C_{18-20}$, or $C_{19-20}$) alkylene, $C_{1-20}$ (i.e., $C_1, C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{1-2}, C_{1-3}, C_{1-4}, C_{1-5}, C_{1-6}, C_{1-7}, C_{1-8}, C_{1-9}, C_{1-10}, C_{1-11}, C_{1-12}, C_{1-13}, C_{1-14}, C_{1-15}, C_{1-16}, C_{1-17}, C_{1-18}, C_{1-19}, C_{1-20}, C_{2-3}, C_{2-4}, C_{2-5}, C_{2-6}, C_{2-7}, C_{2-8}, C_{2-9}, C_{2-10}, C_{2-11}, C_{2-12}, C_{2-13}, C_{2-14}, C_{2-15}, C_{2-16}, C_{2-17}, C_{2-18}, C_{2-19}, C_{2-20}, C_{3-4}, C_{3-5}, C_{3-6}, C_{3-7}, C_{3-8}, C_{3-9}, C_{3-10}, C_{3-11}, C_{3-12}, C_{3-13}, C_{3-14}, C_{3-15}, C_{3-16}, C_{3-17}, C_{3-18}, C_{3-19}, C_{3-20}, C_{4-5}, C_{4-6}, C_{4-7}, C_{4-8}, C_{4-9}, C_{4-10}, C_{4-11}, C_{4-12}, C_{4-13}, C_{4-14}, C_{4-15}, C_{4-16}, C_{4-17}, C_{4-18}, C_{4-19}, C_{4-20}, C_{5-6}, C_{5-7}, C_{5-8}, C_{5-9}, C_{5-10}, C_{5-11}, C_{5-12}, C_{5-13}, C_{5-14}, C_{5-15}, C_{5-16}, C_{5-17}, C_{5-18}, C_{5-19}, C_{5-20}, C_{6-7}, C_{6-8}, C_{6-9}, C_{6-10}, C_{6-11}, C_{6-12}, C_{6-13}, C_{6-14}, C_{6-15}, C_{6-16}, C_{6-17}, C_{6-18}, C_{6-19}, C_{6-20}, C_{7-8}, C_{7-9}, C_{7-10}, C_{7-11}, C_{7-12}, C_{7-13}, C_{7-14}, C_{7-15}, C_{7-16}, C_{7-17}, C_{7-18}, C_{7-19}, C_{7-20}, C_{8-9}, C_{8-10}, C_{8-11}, C_{8-12}, C_{8-13}, C_{8-14}, C_{8-15}, C_{8-16}, C_{8-17}, C_{8-18}, C_{8-19}, C_{8-20}, C_{9-10}, C_{9-11}, C_{9-12}, C_{9-13}, C_{9-14}, C_{9-15}, C_{9-16}, C_{9-17}, C_{9-18}, C_{9-19}, C_{9-20}, C_{10-11}, C_{10-12}, C_{10-13}, C_{10-14}, C_{10-15}, C_{10-16}, C_{10-17}, C_{10-18}, C_{10-19}, C_{10-20}, C_{11-12}, C_{11-13}, C_{11-14}, C_{11-15}, C_{11-16}, C_{11-17}, C_{11-18}, C_{11-19}, C_{11-20}, C_{12-13}, C_{12-14}, C_{12-15}, C_{12-16}, C_{12-17}, C_{12-18}, C_{12-19}, C_{12-20}, C_{13-14}, C_{13-15}, C_{13-16}, C_{13-17}, C_{13-18}, C_{13-19}, C_{13-20}, C_{14-15}, C_{14-16}, C_{14-17}, C_{14-18}, C_{14-19}, C_{14-20}, C_{15-16}, C_{15-17}, C_{15-18}, C_{15-19}, C_{15-20}, C_{16-17}, C_{16-18}, C_{16-19}, C_{16-20}, C_{17-18}, C_{17-19}, C_{17-20}, C_{18-19}, C_{18-20}$, or $C_{19-20}$) perfluoroalkylene, $C_{2-20}$ (i.e., $C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{2-3}, C_{2-4}, C_{2-5}, C_{2-6}, C_{2-7}, C_{2-8}, C_{2-9}, C_{2-10}, C_{2-11}, C_{2-12}, C_{2-13}, C_{2-14}, C_{2-15}, C_{2-16}, C_{2-17}, C_{2-18}, C_{2-19}, C_{2-20}, C_{3-4}, C_{3-5}, C_{3-6}, C_{3-7}, C_{3-8}, C_{3-9}, C_{3-10}, C_{3-11}, C_{3-12}, C_{3-13}, C_{3-14}, C_{3-15}, C_{3-16}, C_{3-17}, C_{3-18}, C_{3-19}, C_{3-20}, C_{4-5}, C_{4-6}, C_{4-7}, C_{4-8}, C_{4-9}, C_{4-10}, C_{4-11}, C_{4-12}, C_{4-13}, C_{4-14}, C_{4-15}, C_{4-16}, C_{4-17}, C_{4-18}, C_{4-19}, C_{4-20}, C_{5-6}, C_{5-7}, C_{5-8}, C_{5-9}, C_{5-10}, C_{5-11}, C_{5-12}, C_{5-13}, C_{5-14}, C_{5-15}, C_{5-16}, C_{5-17}, C_{5-18}, C_{5-19}, C_{5-20}, C_{6-7}, C_{6-8}, C_{6-9}, C_{6-10}, C_{6-11}, C_{6-12}, C_{6-13}, C_{6-14}, C_{6-15}, C_{6-16}, C_{6-17}, C_{6-18}, C_{6-19}, C_{6-20}, C_{7-8}, C_{7-9}, C_{7-10}, C_{7-11}, C_{7-12}, C_{7-13}, C_{7-14}, C_{7-15}, C_{7-16}, C_{7-17}, C_{7-18}, C_{7-19}, C_{7-20}, C_{8-9}, C_{8-10}, C_{8-11}, C_{8-12}, C_{8-13}, C_{8-14}, C_{8-15}, C_{8-16}, C_{8-17}, C_{8-18}, C_{8-19}, C_{8-20}, C_{9-10}, C_{9-11}, C_{9-12}, C_{9-13}, C_{9-14}, C_{9-15}, C_{9-16}, C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, C, —C(O)—, O, S, Si, N, NH, and P, wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, C, —C(O)—, O, S, Si, N, NH, and P is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; and with the proviso that in Formula II at least one of $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, $M^{16}$, and $M^{17}$ is present.

In at least one embodiment of the avobenzone-dendrimer conjugate of Formula IA and Formula II, M is selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, —C(O)—, —C(O)O—, —O—, —S—, —S(O)—, —S(O)$_2$—, —OP(O)(OH)—, —OP(O)(R$^{20}$)—, —OP(OH)$_2$—, —OP(R$^{20}$)$_2$—, —NH—, —N(R$^{20}$)—, —NHC(O)—, —N(R$^{20}$)C(O)—, —Si(R$^{21}$R$^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl; wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, —C(O)—, —C(O)O—, —O—, —S—, —S(O)—, —S(O)$_2$—, —OP(O)(OH)—, —OP(O)(R$^{20}$)—, —P(OH)$_2$—, —OP(R$^{20}$)$_2$—, —NH—, —N(R$^{20}$)—, —NHC(O)—, —N(R$^{20}$)C(O)—, —Si(R$^{21}$R$^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; R$^{20}$ is selected from the group consisting of $C_{1-20}$ alkyl, $C_{2-20}$ alkenyl, $C_{2-20}$ alkynyl, $C_{1-20}$ alkoxy, —OH, —SH, —SC$_{1-20}$ alkyl, —COOH, amine, and aryl; and R$^2$ and R$^{22}$ are independently selected from the group consisting of $C_{1-20}$ alkyl, $C_{2-20}$ alkenyl, —OC$_{1-20}$ alkyl, amine, —OSi(C$_{1-20}$ alkyl)$_3$, —OSi(C$_{1-20}$ alkyl)$_2$(C$_{2-20}$ alkenyl), and —OSi(C$_{1-20}$ alkyl (C$_{2-20}$ alkenyl)$_2$.

In at least one embodiment of the avobenzone-dendrimer conjugate of Formula IA and Formula H, M is a moiety of formula —(CR$^{13}$R$^{14}$)$_t$—, wherein t is 0 to 20 (i.e., 0, 1, 2, 3, 4, 5, 6, 7, 8, 9, 10, 11, 12, 13, 14, 15, 16, 17, 18, 19, 20, 0-1, 0-2, 0-3, 0-4, 0-5, 0-6, 0-7, 0-8, 0-9, 0-10, 0-11, 0-12, 0-13, 0-14, 0-15, 0-16, 0-17, 0-18, 0-19, 0-20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) (Formula IA) or 1 to 20 (i.e., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) (Formula II) and each $R^{13}$ and $R^{14}$ are independently selected from the group consisting of H and $C_{1-3}$ alkyl.

In at least one embodiment of the avobenzone-dendrimer conjugate of Formula II, M' and M" are each independently a moiety of formula-$M^1$-$M^2$-$M^3$-$M^4$-$M^5$-$M^6$-$M^7$-$M^8$-$M^9$-$M^{10}$-$M^{11}$-$M^{12}$-$M^{13}$-$M^{14}$-$M^{15}$-$M^{16}$-$M^{17}$-; wherein $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, $M^{16}$, and $M^{17}$ are each, independently, absent or selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, C, —C(O)—, O, S, Si, N, NH, and P, wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, C, —C(O)—, O, S, Si, N, NH, and P is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; and with the proviso that at least one of $M^1$, $M^2$, $M^3$, $M^4$, $M^5$, $M^6$, $M^7$, $M^8$, $M^9$, $M^{10}$, $M^{11}$, $M^{12}$, $M^{13}$, $M^{14}$, $M^{15}$, $M^{16}$, and $M^{17}$ is present.

In at least one embodiment of the avobenzone-dendrimer conjugate of Formula III, M' and M" are each independently selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{17-19}$, $C_{17-20}$, $C_{18-19}$, $C_{18-20}$, or $C_{19-20}$) perfluoroalkynylene, —C(O)—, —C(O)O—, —O—, —S—, —S(O)—, —S(O)$_2$—, —OP(O)(OH)—, —OP(O)($R^{20}$)—, —OP(OH)$_2$, —OP($R^{20}$)$_2$, —NH—, —N($R^{20}$)—, —NHC(O)—, —N($R^{20}$)C(O)—, —Si($R^{21}R^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl; wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, —C(O)—, —C(O)O—, —O—, —S—, —S(O)—, —S(O)$_2$—, —P(O)(OH)—, —OP(O)($R^2$)—, —P(OH)$_2$, —P($R^{20}$)$_2$, —NH—, —N($R^{20}$)—, —NHC(O)—, —N($R^{20}$)C(O)—, —Si($R^{21}R^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; $R^{20}$ is selected from the group consisting of $C_{1-20}$ alkyl, $C_{2-20}$ alkenyl, $C_{2-20}$ alkynyl, $C_{1-20}$ alkoxy, —OH, —SH, —S$C_{1-20}$ alkyl, —COOH, amine, and aryl; and $R^2$ and $R^{22}$ are independently selected from the group consisting of $C_{1-20}$ alkyl, $C_{2-20}$ alkenyl, —O$C_{1-20}$ alkyl, amine, —OSi($C_{1-20}$ alkyl)$_3$, —OSi($C_{1-20}$ alkyl)$_2$($C_{2-20}$ alkenyl), and —OSi($C_{1-20}$ alkyl)($C_{2-20}$ alkenyl)$_2$.

In at least one embodiment of the avobenzone-dendrimer conjugate of Formula III, M' and M" are each independently a moiety of formula —(C$R^{13}R^{14}$)—, wherein t is 1 to 20 (i.e., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) and each $R^{13}$ and $R^{14}$ are independently selected from the group consisting of H and $C_3$ alkyl.

In Formula IA, n is an integer from 1 to 30 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 5-26, 5-27, 5-28, 5-29, 5-30, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-29, 6-30, 7-8, 7-9, 7-10, 7-11, 7-12, 7-13, 7-14, 7-15, 7-16, 7-17, 7-18, 7-19, 7-20, 7-21, 7-22, 7-23, 7-24, 7-25, 7-26, 7-27, 7-28, 7-29, 7-30, 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30, preferably 1-19).

In at least one embodiment of the avobenzone-dendrimer conjugate of Formula IA, B is a moiety of formula

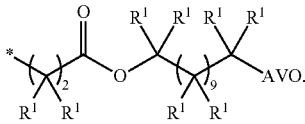

In at least one embodiment of the avobenzone-dendrimer conjugate of Formula II, B is selected from the group consisting of

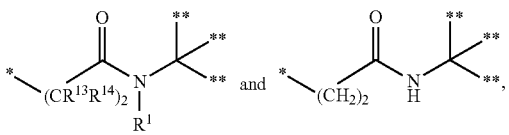

wherein each $R^{13}$ and $R^{14}$ are independently selected from the group consisting of H and $C_{1-3}$ alkyl.

In at least one embodiment of the avobenzone-dendrimer conjugate of Formula III, B is selected from the group consisting of:

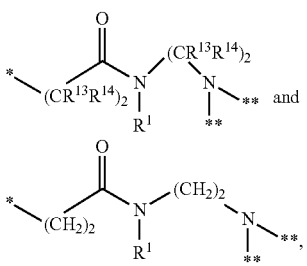

wherein each $R^{13}$ and $R^{14}$ are independently selected from the group consisting of H and $C_{1-3}$ alkyl.

In at least one embodiment of the avobenzone-dendrimer conjugate of Formula IB, Formula II, and Formula III, Q is a moiety of formula $-Q^1-Q^2-Q^3-Q^4-Q^5-Q^6-Q^7-Q^8-Q^9-Q^{10}-Q^{11}-Q^{12}-Q^{13}-Q^{14}-Q^{15}-Q^{16}-Q^{17}-$, wherein $Q^1$, $Q^2$, $Q^3$, $Q^4$, $Q^5$, $Q^6$, $Q^7$, $Q^8$, $Q^9$, $Q^{10}$, $Q^{11}$, $Q^{12}$, $Q^{13}$, $Q^{14}$, $Q^{15}$, $Q^{16}$, and $Q^{17}$ are each, independently, absent or selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, C, —C(O)—, O, S, Si, N, NH, and P, wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, C, —C(O)—, O, S, Si, N, NH, and P is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O.

In at least one embodiment of the avobenzone-dendrimer conjugate of Formula IB, Formula II, and Formula III, Q is selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, —C(O)—, —C(O)O—, —O—, —S—, —S(O)—, —S(O)$_2$—, —OP(O)(OH)—, —OP(O)(R$^{20}$)—, —OP(OH)$_2$—, —OP(R$^{20}$)$_2$, —NH—, —N(R$^{20}$)—, —NHC(O)—, —N(R$^{20}$)C(O)—, —Si(R$^{21}$R$^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl; wherein each $C_{1-20}$ alkylene, $C_{1-20}$ perfluoroalkylene, $C_{2-20}$ alkenylene, $C_{2-20}$ perfluoroalkenylene, $C_{2-20}$ alkynylene, $C_{2-20}$ perfluoroalkynylene, —C(O)—, —C(O)O—, —O—, —S—, —S(O)—, —S(O)$_2$—, —P(O)(OH)—, —P(O)(R$^{20}$)—, —OP(OH)$_2$—, —OP(R$^{20}$)$_2$—, —NH—, —N(R$^{20}$)—, —NHC(O)—, —N(R$^{20}$)C(O)—, —Si(R$^{21}$R$^{22}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; R$^{20}$ is selected from the group consisting of $C_{1-20}$ alkyl, $C_{2-20}$ alkenyl, $C_{2-20}$ alkynyl, $C_{1-20}$ alkoxy, —OH, —SH, —SC$_{1-20}$ alkyl, —COOH, amine, and aryl; and R$^{21}$ and R$^{22}$ are independently selected from the group consisting of $C_{1-20}$ alkyl, $C_{2-20}$ alkenyl, —OC$_{1-20}$ alkyl, amine, —OSi(C$_{1-20}$ alkyl)$_3$, —OSi(C$_{1-20}$ alkyl)$_2$(C$_{2-20}$ alkenyl), and —OSi(C$_{1-20}$ alkyl)(C$_{2-20}$ alkenyl)$_2$.

In at least one embodiment of the avobenzone-dendrimer conjugate of Formula IB and Formula II, Q is a moiety of formula —(CR$^{15}$R$^{16}$)$_u$—, wherein u is 0 to 20 (i.e., 0, 1, 2, 3, 4, 5, 6, 7, 8, 9, 10, 11, 12, 13, 14, 15, 16, 17, 18, 19, 20, 0-1, 0-2, 0-3, 0-4, 0-5, 0-6, 0-7, 0-8, 0-9, 0-10, 0-11, 0-12, 0-13, 0-14, 0-15, 0-16, 0-17, 0-18, 0-19, 0-20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) and each R$^{15}$ and R$^{16}$ are independently selected from the group consisting of H and $C_{1-3}$ alkyl.

In at least one embodiment of the avobenzone-dendrimer conjugate of Formula III, Q is a moiety of formula —(CR$^{15}$R$^{16}$)$_u$—(CO)—NR$^{17}$—(CR$^{15}$R$^{16}$)$_u$—NR$^{17}$—(CO)—(CR$^{15}$R$^{16}$)$_u$—, wherein each u is 0 to 20 (i.e., 0, 1, 2, 3, 4, 5, 6, 7, 8, 9, 10, 11, 12, 13, 14, 15, 16, 17, 18, 19, 20, 0-1, 0-2, 0-3, 0-4, 0-5, 0-6, 0-7, 0-8, 0-9, 0-10, 0-11, 0-12, 0-13, 0-14, 0-15, 0-16, 0-17, 0-18, 0-19, 0-20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, or 19-20) and each $R^{15}$, $R^{16}$, and $R^{17}$ is independently selected from the group consisting of H and $C_{1-3}$ alkyl.

L in Formula IB, Formula II, and Formula III is a linker. In at least one embodiment, each L, independently, is a covalent bond or is a saturated or unsaturated, branched or unbranched, optionally substituted carbon chain of from 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-46, 3-47, 3-48, 3-49, 3-50, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-46, 4-47, 4-48, 4-49, 4-50, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-37, 5-38, 5-39, 5-40, 5-41, 5-42, 5-43, 5-44, 5-45, 5-46, 5-47, 5-48, 5-49, 5-50, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-46, 6-47, 6-48, 6-49, 6-50, 7-8, 7-9, 7-10, 7-11, 7-12, 7-13, 7-14, 7-15, 7-16, 7-17, 7-18, 7-19, 7-20, 7-21, 7-22, 7-23, 7-24, 7-25, 7-26, 7-27, 7-28, 7-29, 7-30, 7-31, 7-32, 7-33, 7-34, 7-35, 7-36, 7-37, 7-38, 7-39, 7-40, 7-41, 7-42, 7-43, 7-44, 7-45, 7-46, 7-47, 7-48, 7-49, 7-50, 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 8-31, 8-32, 8-33, 8-34, 8-35, 8-36, 8-37, 8-38, 8-39, 8-40, 8-41, 8-42, 8-43, 8-44, 8-45, 8-46, 8-47, 8-48, 8-49, 8-50, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 9-31, 9-32, 9-33, 9-34, 9-35, 9-36, 9-37, 9-38, 9-39, 9-40, 9-41, 9-42, 9-43, 9-44, 9-45, 9-46, 9-47, 9-48, 9-49, 9-50, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 10-41, 10-42, 10-43, 10-44, 10-45, 10-46, 10-47, 10-48, 10-49, 10-50, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 11-31, 11-32, 11-33, 11-34, 11-35, 11-36, 11-37, 11-38, 11-39, 11-40, 11-41, 11-42, 11-43, 11-44, 11-45, 11-46, 11-47, 11-48, 11-49, 11-50, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 12-31, 12-32, 12-33, 12-34, 12-35, 12-36, 12-37, 12-38, 12-39, 12-40, 12-41, 12-42, 12-43, 12-44, 12-45, 12-46, 12-47, 12-48, 12-49, 12-50, 13-14, 13-15, 13-16, 13-17, 13-18, 13-19, 13-20, 13-21, 13-22, 13-23, 13-24, 13-25, 13-26, 13-27, 13-28, 13-29, 13-30, 13-31, 13-32, 13-33, 13-34, 13-35, 13-36, 13-37, 13-38, 13-39, 13-40, 13-41, 13-42, 13-43, 13-44, 13-45, 13-46, 13-47, 13-48, 13-49, 13-50, 14-15, 14-16, 14-17, 14-18, 14-19, 14-20, 14-21, 14-22, 14-23, 14-24, 14-25, 14-26, 14-27, 14-28, 14-29, 14-30, 14-31, 14-32, 14-33, 14-34, 14-35, 14-36, 14-37, 14-38, 14-39, 14-40, 14-41, 14-42, 14-43, 14-44, 14-45, 14-46, 14-47, 14-48, 14-49, 14-50, 15-16, 15-17, 15-18, 15-19, 15-20, 15-21, 15-22, 15-23, 15-24, 15-25, 15-26, 15-27, 15-28, 15-29, 15-30, 15-31, 15-32, 15-33, 15-34, 15-35, 15-36, 15-37, 15-38, 15-39, 15-40, 15-41, 15-42, 15-43, 15-44, 15-45, 15-46, 15-47, 15-48, 15-49, 15-50, 16-17, 16-18, 16-19, 16-20, 16-21, 16-22, 16-23, 16-24, 16-25, 16-26, 16-27, 16-28, 16-29, 16-30, 16-31, 16-32, 16-33, 16-34, 16-35, 16-36, 16-37, 16-38, 16-39, 16-40, 16-41, 16-42, 16-43, 16-44, 16-45, 16-46, 16-47, 16-48, 16-49, 16-50, 17-18, 17-19, 17-20, 17-21, 17-22, 17-23, 17-24, 17-25, 17-26, 17-27, 17-28, 17-29, 17-30, 17-31, 17-32, 17-33, 17-34, 17-35, 17-36, 17-37, 17-38, 17-39, 17-40, 17-41, 17-42, 17-43, 17-44, 17-45, 17-46, 17-47, 17-48, 17-49, 17-50, 18-19, 18-20, 18-21, 18-22, 18-23, 18-24, 18-25, 18-26, 18-27, 18-28, 18-29, 18-30, 18-31, 18-32, 18-33, 18-34, 18-35, 18-36, 18-37, 18-38, 18-39, 18-40, 18-41, 18-42, 18-43, 18-44, 18-45, 18-46, 18-47, 18-48, 18-49, 18-50, 19-20, 19-21, 19-22, 19-23, 19-24, 19-25, 19-26, 19-27, 19-28, 19-29, 19-30, 19-31, 19-32, 19-33, 19-34, 19-35, 19-36, 19-37, 19-38, 19-39, 19-40, 19-41, 19-42, 19-43, 19-44, 19-45, 19-46, 19-47, 19-48, 19-49, 19-50, 20-21, 20-22, 20-23, 20-24, 20-25, 20-26, 20-27, 20-28, 20-29, 20-30, 20-31, 20-32, 20-33, 20-34, 20-35, 20-36, 20-37, 20-38, 20-39, 20-40, 20-41, 20-42, 20-43, 20-44, 20-45, 20-46, 20-47, 20-48, 20-49, 20-50, 21-22, 21-23, 21-24, 21-25, 21-26, 21-27, 21-28, 21-29, 21-30, 21-31, 21-32, 21-33, 21-34, 21-35, 21-36, 21-37, 21-38, 21-39, 21-40, 21-41, 21-42, 21-43, 21-44, 21-45, 21-46, 21-47, 21-48, 21-49, 21-50, 22-23, 22-24, 22-25, 22-26, 22-27, 22-28, 22-29, 22-30, 22-31, 22-32, 22-33, 22-34, 22-35, 22-36, 22-37, 22-38, 22-39, 22-40, 22-41, 22-42, 22-43, 22-44, 22-45, 22-46, 22-47, 22-48, 22-49, 22-50, 23-24, 23-25, 23-26, 23-27, 23-28, 23-29, 23-30, 23-31, 23-32, 23-33, 23-34, 23-35, 23-36, 23-37, 23-38, 23-39, 23-40, 23-41, 23-42, 23-43, 23-44, 23-45, 23-46, 23-47, 23-48, 23-49, 23-50, 24-25, 24-26, 24-27, 24-28, 24-29, 24-30, 24-31, 24-32, 24-33, 24-34, 24-35, 24-36, 24-37, 24-38, 24-39, 24-40, 24-41, 24-42, 24-43, 24-44, 24-45, 24-46, 24-47, 24-48, 24-49, 24-50, 25-26, 25-27, 25-28, 25-29, 25-30, 25-31, 25-32, 25-33, 25-34, 25-35, 25-36, 25-37, 25-38, 25-39, 25-40, 25-41, 25-42, 25-43, 25-44, 25-45, 25-46, 25-47, 25-48, 25-49, 25-50, 26-27, 26-28, 26-29, 26-30, 26-31, 26-32, 26-33, 26-34, 26-35, 26-36, 26-37, 26-38, 26-39, 26-40, 26-41, 26-42, 26-43, 26-44, 26-45, 26-46, 26-47, 26-48, 26-49, 26-50, 27-28, 27-29, 27-30, 27-31, 27-32, 27-33, 27-34, 27-35, 27-36, 27-37, 27-38, 27-39, 27-40, 27-41, 27-42, 27-43, 27-44, 27-45, 27-46, 27-47, 27-48, 27-49, 27-50, 28-29, 28-30, 28-31, 28-32, 28-33, 28-34, 28-35, 28-36, 28-37, 28-38, 28-39, 28-40, 28-41, 28-42, 28-43, 28-44, 28-45, 28-46, 28-47, 28-48, 28-49, 28-50, 29-30, 29-31, 29-32, 29-33, 29-34, 29-35, 29-36, 29-37, 29-38, 29-39, 29-40, 29-41, 29-42, 29-43, 29-44, 29-45, 29-46, 29-47, 29-48, 29-49, 29-50, 30-31, 30-32, 30-33, 30-34, 30-35, 30-36, 30-37, 30-38, 30-39, 30-40, 30-41, 30-42, 30-43, 30-44, 30-45, 30-46, 30-47, 30-48, 30-49, 30-50, 31-32, 31-33, 31-34, 31-35, 31-36, 31-37, 31-38, 31-39, 31-40, 31-41, 31-42, 31-43, 31-44, 31-45, 31-46, 31-47, 31-48, 31-49, 31-50, 32-33, 32-34, 32-35, 32-36, 32-37, 32-38, 32-39, 32-40, 32-41, 32-42, 32-43, 32-44, 32-45, 32-46, 32-47, 32-48, 32-49, 32-50, 33-34, 33-35, 33-36, 33-37, 33-38, 33-39, 33-40, 33-41, 33-42, 33-43, 33-44, 33-45, 33-46, 33-47, 33-48, 33-49, 33-50, 34-35, 34-36, 34-37, 34-38, 34-39, 34-40, 34-41, 34-42, 34-43, 34-44, 34-45, 34-46, 34-47, 34-48, 34-49, 34-50, 35-36, 35-37, 35-38, 35-39, 35-40, 35-41, 35-42, 35-43, 35-44, 35-45, 35-46, 35-47, 35-48, 35-49, 35-50, 36-37, 36-38, 36-39, 36-40, 36-41, 36-42, 36-43, 36-44, 36-45, 36-46, 36-47, 36-48, 36-49, 36-50, 37-38, 37-39, 37-40, 37-41, 37-42, 37-43, 37-44, 37-45, 37-46, 37-47, 37-48, 37-49, 37-50, 38-39, 38-40, 38-41, 38-42, 38-43, 38-44, 38-45, 38-46, 38-47, 38-48, 38-49, 38-50, 39-40, 39-41, 39-42, 39-43, 39-44, 39-45, 39-46, 39-47, 39-48, 39-49, 39-50, 40-41, 40-42, 40-43, 40-44, 40-45, 40-46, 40-47, 40-48, 40-49, 40-50, 41-42, 41-43, 41-44, 41-45, 41-46, 41-47, 41-48, 41-49, 41-50, 42-43, 42-44, 42-45, 42-46, 42-47, 42-48, 42-49, 42-50, 43-44, 43-45, 43-46, 43-47, 43-48, 43-49, 43-50, 44-45, 44-46, 44-47, 44-48, 44-49, 44-50, 45-46, 45-47, 45-48, 45-49, 45-50, 46-47, 46-48, 46-49, 46-50, 47-48, 47-49, 47-50, 48-49, 48-50, 49-50) atoms in length, and optionally includes from 1 to 25 (i.e., 1, 2, 3, 4, 5, 6, 7, 8, 9, 10, 11, 12, 13, 14, 15, 16, 17, 18, 19, 20, 21, 22, 23, 24, 25, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 7-8, 7-9, 7-10, 7-11, 7-12, 7-13, 7-14, 7-15, 7-16, 7-17, 7-18, 7-19, 7-20, 7-21, 7-22, 7-23, 7-24, 7-25, 8-9, 8-10, 8-11, 8-12, 8-13, 8-14, 8-15, 8-16, 8-17, 8-18, 8-19, 8-20, 8-21, 8-22, 8-23, 8-24, 8-25, 9-10, 9-11, 9-12, 9-13, 9-14, 9-15, 9-16, 9-17, 9-18, 9-19, 9-20, 9-21, 9-22, 9-23, 9-24, 9-25, 10-11, 10-12, 10-13, 10-14, 10-15, 10-16, 10-17, 10-18, 10-19, 10-20, 10-21, 10-22, 10-23, 10-24, 10-25, 11-12, 11-13, 11-14, 11-15, 11-16, 11-17, 11-18, 11-19, 11-20, 11-21, 11-22, 11-23, 11-24, 11-25, 12-13, 12-14, 12-15, 12-16, 12-17, 12-18, 12-19, 12-20, 12-21, 12-22, 12-23, 12-24, 12-25, 13-14, 13-15, 13-16, 13-17, 13-18, 13-19, 13-20, 13-21, 13-22, 13-23, 13-24, 13-25, 14-15, 14-16, 14-17, 14-18, 14-19, 14-20, 14-21, 14-22, 14-23, 14-24, 14-25, 15-16, 15-17, 15-18, 15-19, 15-20, 15-21, 15-22, 15-23, 15-24, 15-25, 16-17, 16-18, 16-19, 16-20, 16-21, 16-22, 16-23, 16-24, 16-25, 17-18, 17-19, 17-20, 17-21, 17-22, 17-23, 17-24, 17-25, 18-19, 18-20, 18-21, 18-22, 18-23, 18-24, 18-25, 19-20, 19-21, 19-22, 19-23, 19-24, 19-25, 20-21, 20-22, 20-23, 20-24, 20-25, 21-22, 21-23, 21-24, 21-25, 22-23, 22-24, 22-25, 23-24, 23-25, or 24-25) heteroatoms in the chain. In at least one embodiment, each L, independently, is a covalent bond or:

(i) is a moiety of formula -$L^1$-$L^2$-$L^3$-$L^4$-$L^5$-$L^6$-$L^7$-$L^8$-$L^9$-$L^{10}$-$L^{11}$-$L^{12}$-$L^{13}$-$L^{14}$-$L^{15}$-$L^{16}$-$L^{17}$-; wherein $L^1$, $L^2$, $L^3$, $L^4$, $L^5$, $L^6$, $L^7$, $L^8$, $L^9$, $L^{10}$, $L^{11}$, $L^{12}$, $L^{13}$, $L^{14}$, $L^{15}$, $L^{16}$, and $L^{17}$ are each, independently, absent or selected from the group consisting of $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkylene, $C_{1-20}$ (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{1-11}$, $C_{1-12}$, $C_{1-13}$, $C_{1-14}$, $C_{1-15}$, $C_{1-16}$, $C_{1-17}$, $C_{1-18}$, $C_{1-19}$, $C_{1-20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkenylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) alkynylene, $C_{2-20}$ (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{2-3}$, $C_{2-4}$, $C_{2-5}$, $C_{2-6}$, $C_{2-7}$, $C_{2-8}$, $C_{2-9}$, $C_{2-10}$, $C_{2-11}$, $C_{2-12}$, $C_{2-13}$, $C_{2-14}$, $C_{2-15}$, $C_{2-16}$, $C_{2-17}$, $C_{2-18}$, $C_{2-19}$, $C_{2-20}$, $C_{3-4}$, $C_{3-5}$, $C_{3-6}$, $C_{3-7}$, $C_{3-8}$, $C_{3-9}$, $C_{3-10}$, $C_{3-11}$, $C_{3-12}$, $C_{3-13}$, $C_{3-14}$, $C_{3-15}$, $C_{3-16}$, $C_{3-17}$, $C_{3-18}$, $C_{3-19}$, $C_{3-20}$, $C_{4-5}$, $C_{4-6}$, $C_{4-7}$, $C_{4-8}$, $C_{4-9}$, $C_{4-10}$, $C_{4-11}$, $C_{4-12}$, $C_{4-13}$, $C_{4-14}$, $C_{4-15}$, $C_{4-16}$, $C_{4-17}$, $C_{4-18}$, $C_{4-19}$, $C_{4-20}$, $C_{5-6}$, $C_{5-7}$, $C_{5-8}$, $C_{5-9}$, $C_{5-10}$, $C_{5-11}$, $C_{5-12}$, $C_{5-13}$, $C_{5-14}$, $C_{5-15}$, $C_{5-16}$, $C_{5-17}$, $C_{5-18}$, $C_{5-19}$, $C_{5-20}$, $C_{6-7}$, $C_{6-8}$, $C_{6-9}$, $C_{6-10}$, $C_{6-11}$, $C_{6-12}$, $C_{6-13}$, $C_{6-14}$, $C_{6-15}$, $C_{6-16}$, $C_{6-17}$, $C_{6-18}$, $C_{6-19}$, $C_{6-20}$, $C_{7-8}$, $C_{7-9}$, $C_{7-10}$, $C_{7-11}$, $C_{7-12}$, $C_{7-13}$, $C_{7-14}$, $C_{7-15}$, $C_{7-16}$, $C_{7-17}$, $C_{7-18}$, $C_{7-19}$, $C_{7-20}$, $C_{8-9}$, $C_{8-10}$, $C_{8-11}$, $C_{8-12}$, $C_{8-13}$, $C_{8-14}$, $C_{8-15}$, $C_{8-16}$, $C_{8-17}$, $C_{8-18}$, $C_{8-19}$, $C_{8-20}$, $C_{9-10}$, $C_{9-11}$, $C_{9-12}$, $C_{9-13}$, $C_{9-14}$, $C_{9-15}$, $C_{9-16}$, $C_{9-17}$, $C_{9-18}$, $C_{9-19}$, $C_{9-20}$, $C_{10-11}$, $C_{10-12}$, $C_{10-13}$, $C_{10-14}$, $C_{10-15}$, $C_{10-16}$, $C_{10-17}$, $C_{10-18}$, $C_{10-19}$, $C_{10-20}$, $C_{11-12}$, $C_{11-13}$, $C_{11-14}$, $C_{11-15}$, $C_{11-16}$, $C_{11-17}$, $C_{11-18}$, $C_{11-19}$, $C_{11-20}$, $C_{12-13}$, $C_{12-14}$, $C_{12-15}$, $C_{12-16}$, $C_{12-17}$, $C_{12-18}$, $C_{12-19}$, $C_{12-20}$, $C_{13-14}$, $C_{13-15}$, $C_{13-16}$, $C_{13-17}$, $C_{13-18}$, $C_{13-19}$, $C_{13-20}$, $C_{14-15}$, $C_{14-16}$, $C_{14-17}$, $C_{14-18}$, $C_{14-19}$, $C_{14-20}$, $C_{15-16}$, $C_{15-17}$, $C_{15-18}$, $C_{15-19}$, $C_{15-20}$, $C_{16-17}$, $C_{16-18}$, $C_{16-19}$, $C_{16-20}$, $C_{17-18}$, $C_{17-19}$, $C_{17-20}$, $C_{18-19}$, $C_{18-20}$, or $C_{19-20}$) perfluoroalkynylene, C, —C(O)—, O, S, Si, N, NH, and P, wherein each $C_{1-20}$ alkylene, $C_{1-20}$ perfluoroalkylene, $C_{2-20}$ alkenylene, $C_{2-20}$ (perfluoroalkenylene, $C_{2-20}$ alkynylene, $C_{2-20}$, perfluoroalkynylene, C, —C(O)—, O, S, Si, N, NH, and P is optionally substituted from 1 to 10 (i.e., 1, 2, 3, 4, 5, 6, 7, 8, 9, 10, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10) times with a substituent independently selected at each occurrence from the group consisting of halogen, OH, $C_{1-20}$ alkoxy, and =O; and with the proviso that at least one of $L^1$, $L^2$, $L^3$, $L^4$, $L^5$, $L^6$, $L^7$, $L^8$, $L^9$, $L^{10}$, $L^{11}$, $L^{12}$, $L^{13}$, $L^{14}$, $L^{15}$, $L^{16}$, and $L^{17}$ is present; or (ii) has the formula —$R^{17}R^{18}R^{19}$—, wherein each $R^{17}$, $R^{18}$, and $R^{19}$ is optionally present and, if present, is independently selected from the group consisting of $C_{1-6}$ (i.e., $C_1$, $C_2$, $C_3$, $C_4$, $C_5$, $C_6$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) alkylene, $C_{1-6}$ (i.e., $C_1$, $C_2$, $C_3$, $C_4$, $C_5$, $C_6$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) perfluoroalkylene, $C_{2-6}$ (i.e., $C_2$, $C_3$, $C_4$, $C_5$, $C_6$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) alkenylene, $C_{2-6}$ (i.e., $C_2$, $C_3$, $C_4$, $C_5$, $C_6$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) perfluoroalkynylene, $C_{2-6}$ (i.e., $C_2$, $C_3$, $C_4$, $C_5$, $C_6$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) alkynylene, $C_{2-6}$ (i.e., $C_2$, $C_3$, $C_4$, $C_5$, $C_6$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, or $C_{5-6}$) perfluoroalkynylene, —C(O)—, —C(O)O—, —O—, —S—, —S(O)—, —S(O)$_2$—, —OP(O)(OH)—, —OP(O)($R^{20}$)—, —P(OH)$_2$—, —P($R^{20}$)$_2$—, —NH—, —N($R^{20}$)—, —NHC(O)—, —N($R^{20}$)C(O)—, —Si($R^{21}R^{21}$)—, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl; wherein each $C_{1-6}$ alkylene, $C_{1-6}$ perfluoroalkylene, $C_{2-6}$ alkenylene, $C_{2-6}$ perfluoroalkenylene, $C_{2-6}$ alkynylene, $C_{2-6}$, perfluoroalkynylene, cycloalkylene, hydroxyalkylene, thiol, thioalkylene, alkylthioalkylene, alkoxy, aldehyde, ketone, acid, amine, amide, alcohol, heterocyclylene, arylene, heteroarylene, arylalkylene, and acyl is optionally substituted with from 1 to 3 (i.e., 1, 2, 3, 1-2, 1-3, or 2-3) substituents independently selected at each occurrence from the group consisting of $C_{1-11}$ alkyl, halogen, —CN, —COOR$^6$, —C(O)R$^7$, —OR$^8$, —NR$^9$R$^{10}$, —S(O)$_x$R$^{11}$, —SR$^{12}$, and aryl, wherein R$^6$, R$^7$, R$^8$, R$^9$, R$^{10}$, R$^{11}$ and R$^{12}$ are each independently selected from the group consisting of H, $C_{1-11}$ alkyl, aryl, and heteroaryl; wherein each R$^{20}$ is independently selected from the group consisting of $C_{1-20}$ alkyl, $C_{2-20}$ alkenyl, $C_{2-20}$ alkynyl, $C_{1-20}$ alkoxy, —OH, —SH, —$SC_{1-20}$ alkyl, —COOH, amine, and aryl; $R^2$ and $R^{22}$ are independently selected from the group consisting of $C_{1-20}$ alkyl, $C_{2-20}$ alkenyl, —$OC_{1-20}$ alkyl, amine, —$OSi(C_{1-20}$ alkyl$)_3$, —$OSi(C_{1-20}$ alkyl$)_2(C_{2-20}$ alkenyl), and —$OSi(C_{1-20}$ alkyl$)(C_{2-20}$ alkenyl$)_2$; and x is 1 or 2; and with the proviso that at least one of $R^{17}$, $R^{18}$, and $R^{19}$ is present. In at least one embodiment, each L is the same.

Z in Formula IB, Formula II, and Formula III is an optional spacer that, as will be apparent to the skilled artisan, can be added to lengthen one or more branches of the dendrimer (to, e.g., increase the overall size of the conjugate, increase the distance between an avobenzone molecule and other groups within the dendrimer that may influence the avobenzone's activity, increase stability of the scaffold, increase flexibility of the scaffold, alter the solubility of the scaffold, etc.). In at least one embodiment, each Z is, independently, a unit formed from a bioconjugation reaction. In at least one embodiment, each Z is the same.

A variety of bioconjugation reactions can be used to produce a wide variety of spacers. Suitable bioconjugation reactions include, for example, click reactions (including copper catalyzed click reactions, strain promoted click reactions), Staudinger ligation (e.g., Saxon & Bertozzi, *Science* 287(5460):2007 (2000), which is hereby incorporated by reference in its entirety), Schiff base chemistry (e.g., Yamgar et al., *J. Chem. Pharm. Res.* 2(5):216-24 (2010), which is hereby incorporated by reference in its entirety), reactions involving the thiol group of a cytosine residue, reactions involving lysine residues, Diels-Alder reactions (e.g., Corey et al., *Angew. Chem. Int. Ed.* 41:1650-67 (2002), which is hereby incorporated by reference in its entirety), thiol one chemistry, amide formation, and various other bioconjugation reactions (e.g., as described in GREG T. HERMANSON, BIOCONJUGATE TECHNIQUES (3d ed. 2013), which is hereby incorporated by reference in its entirety).

In some embodiments, Z is formed by a click reaction. A suitable click reaction is a 1,3-dipolar cycloaddition reaction. Click reactions of this type involve, for example, the coupling of two different moieties (e.g., a peptide and a functional group, a first functional group and a second functional group) via a 1,3-dipolar cycloaddition reaction between an alkyne moiety (or equivalent thereof) on the surface of the first moiety and an azide moiety (or equivalent thereof) or any active end group (such as, for example, a primary amine end group, a hydroxyl end group, a carboxylic acid end group, a thiol end group, etc.) on the second moiety. "Click chemistry" is an attractive coupling method because, for example, it can be performed with a wide variety of solvent conditions including aqueous environments. For example, the stable triazole ring that results from coupling the alkyne with the azide in the 1,3-dipolar cycloaddition reaction is frequently achieved at quantitative yields and is considered to be biologically inert (see, e.g., Rostovtsev et al., *Angewandte Chem. Int. Ed.* 41(14):2596 (2002); Wu et al., *Angewandte Chem. Int. Ed.* 43(30):3928-32 (2004), each of which is hereby incorporated by reference in its entirety). As will be apparent to the skilled artisan, other click reactions may also be used to form spacer Z.

Suitable examples of Z include, without limitation, triazoles, alkylenes, and amides, where the triazole, alkylene, and amide can be optionally substituted.

In at least one embodiment of the avobenzone-dendrimer conjugate of Formula II, X is selected from the group consisting of *—$(CR^{15}R^{16})_2$—CO-L-Z-AVO, wherein $R^{15}$ and $R^{16}$ are independently selected from the group consisting of H and $C_{1-3}$ alkyl; *—$(CH_2)_2$—CO—O—Z-AVO; *—$(CH_2)_2$—CO—$CH_2$-AVO; and *—$(CH_2)_2$—CO-AVO.

In at least one embodiment, the the avobenzone-dendrimer conjugate is G1N, G2N, or G2P:

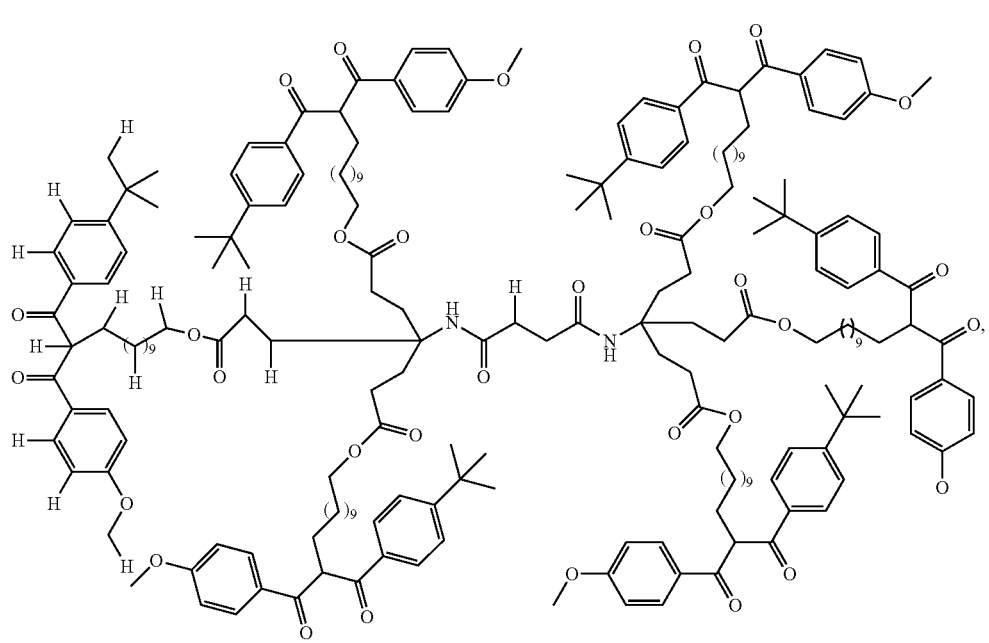

G1N

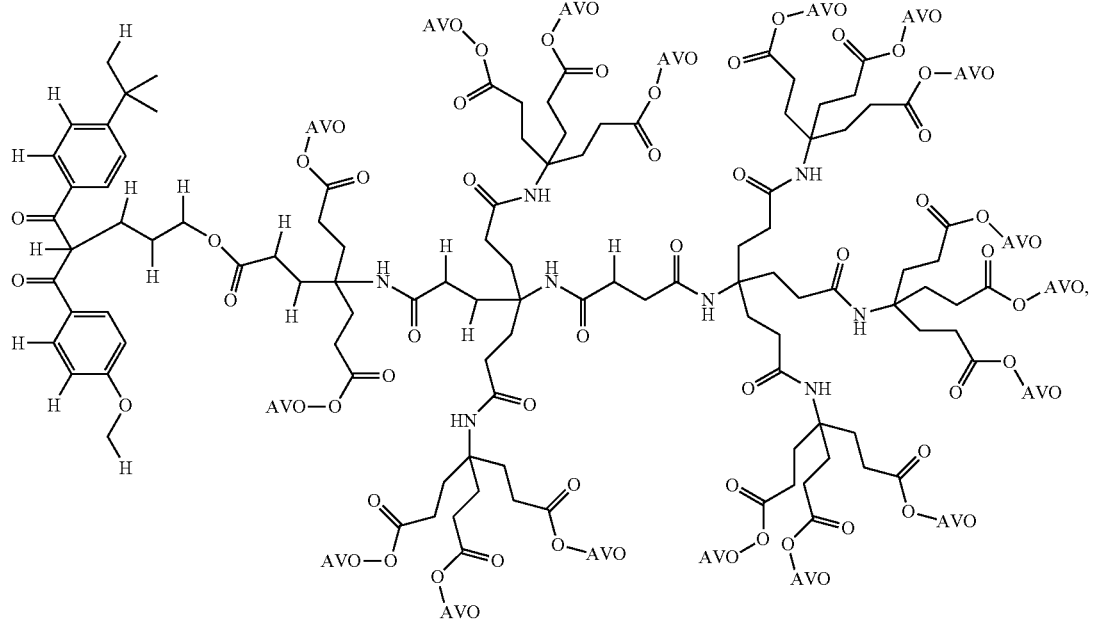
G2N
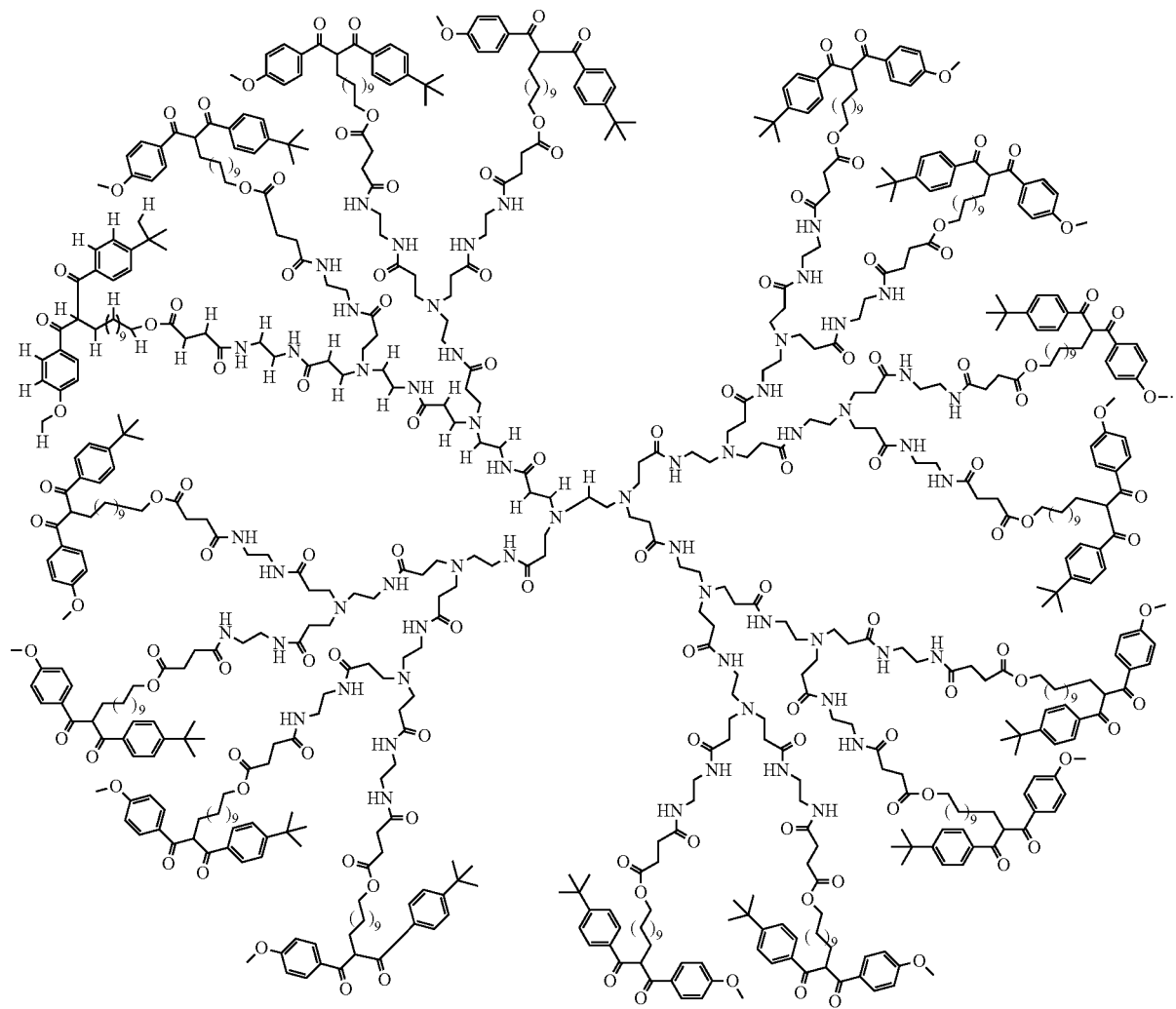
G2P

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" means an aliphatic hydrocarbon group which may be straight or branched having about 1 to about 20 (e.g., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain, unless otherwise specified. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl. An alkylene is a divalent, straight or branched chain alkane group.

The term "alkenyl" means an aliphatic hydrocarbon group containing one or more carbon-carbon double bonds and which may be straight or branched having about 2 to about 20 (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain. Preferred alkenyl groups have 2 to about 6 (e.g., 2, 3, 4, 5, 6, 2-3, 2-4, 2-5, 2-6, 3-4, 3-5, 3-6, 4-5, 4-6, 5-6) carbon atoms in the chain. Exemplary alkenyl groups include ethenyl, propenyl, n-butenyl, and i-butenyl. An alkenylene is a divalent, straight or branched chain alkene group.

The term "alkynyl" means an aliphatic hydrocarbon group containing one or more carbon-carbon triple bonds and which may be straight or branched having about 2 to about 20 (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain. Preferred alkynyl groups have 2 to about 6 (e.g., 2, 3, 4, 5, 6, 2-3, 2-4, 2-5, 2-6, 3-4, 3-5, 3-6, 4-5, 4-6, 5-6) carbon atoms in the chain. Exemplary alkynyl groups include ethynyl, propynyl, n-butynyl, 2-butynyl, 3-methyl-butynyl, and n-pentynyl. An alkynylene is a divalent, straight or branched chain alkyne.

The term "$C_{1-20}$ perfluoroalkylene" means a partially or totally fluorinated alkylene group. Exemplary $C_{1-20}$ perfluoroalkylene groups include —$CF_2$—, —CHF—, —CHF—$CHF_2$—, —CHF—CHF—, —$CH_2$—$CF_2$—, —$CH_2$—CHF—, —$CF_2$—$CF_2$—, —$CF_2$—CHF—, —$CH_2$—CHF—$CF_2$—, —$CH_2$—CHF—CHF—, —$CH_2$—$CH_2$—$CF_2$—, —$CH_2$—$CH_2$—CHF—, —$CH_2$—$CF_2$—$CF_2$—, —$CH_2$—$CF_2$—CHF—, —CHF—CHF—$CF_2$—, —CHF—CHF—CHF—, —CHF—$CH_2$—$CF_2$—, —CHF—$CH_2$—CHF—, —CHF—$CF_2$—$CF_2$—, —CHF—$CF_2$—CHF—, —$CF_2$—CHF—$CF_2$—, —$CF_2$—CHF—CHF—, —$CF_2$—$CH_2$—$CF_2$—, —$CF_2$—$CH_2$—CHF—, —$CF_2$—$CF_2$—$CF_2$—, and —$CF_2$—$CF_2$—CHF—.

The term "$C_{2-20}$ perfluoroalkenylene" means a partially or totally fluorinated alkenylene group. Exemplary $C_{2-20}$ perfluoroalkenylene groups include —CF=CF—, —CH=CF—, —$CF_2$—CF=CF—, —$CH_2$—CF=CF—, —CHF—CF=CF—, —$CH_2$—CH=CF—, —$CH_2$—CF=CH—, —$CF_2$—CH=CF—, —$CF_2$—CF=CF—, —CHF—CH=CF—, —CHF—CF=CH—, —CF=CF—$CF_2$—$CF_2$—, —CH=CH—$CF_2$—$CF_2$—, —CF=CH—$CF_2$—$CF_2$—, —CH=CF—$CF_2$—$CF_2$—, —CF=CF—CHF—CHF—, —CF=CF—$CH_2$—$CF_2$—, and —CF=CF—$CH_2$—$CHF_2$—.

The term "$C_{2-20}$ perfluoroalkynylene" means a partially or totally fluorinated alkynylene group. Exemplary $C_{2-20}$ perfluoroalkynylene groups include -$CF_2$—C≡C—, —CHF—C≡C—, —C≡C—$CF_2$—$CF_2$—, —C≡C—CHF—$CF_2$—, —C≡C—$CH_2$—$CF_2$—, —C≡C—CHF—CHF—, —C≡C—$CF_2$—CHF—, —C≡C—$CF_2$—$CH_2$—, —$CF_2$—C≡C—$CF_2$—, —$CH_2$—C≡C—$CF_2$—, —CHF—C≡C—$CF_2$—, —CHF—C≡C—CHF—, and —CHF—C≡C—$CF_2$—.

The term "cycloalkyl" refers to a non-aromatic saturated or unsaturated mono- or polycyclic ring system which may contain 3 to 9 (i.e., 3, 4, 5, 6, 7, 8, 9, 3-4, 3-5, 3-6, 3-7, 3-8, 3-9, 4-5, 4-6, 4-7, 4-8, 4-9, 5-6, 5-7, 5-8, 5-9, 6-7, 6-8, 6-9, 7-8, 7-9, or 8-9) carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane. A cycloalkylene is a divalent, straight or branched chain cycloalkane group.

The term "hydroxyalkyl" means an alkyl group substituted with one or more hydroxy substituents, wherein the alkyl group is as herein described. A hydroxyalkylene is a divalent, straight or branched chain hydroxyalkane group.

The term "thioalkyl" means an alkyl group substituted with one or more mecaptan (thiol) substituents, wherein the alkyl group is as herein described. A thioalkylene is a divalent, straight or branched chain thioalkane group.

The term "alkylthioalkyl" means a thioalkyl group substituted with one or more alkyl substituents, wherein the alkyl group is as herein described. Particularly, the thiol group of the thioalkyl can be substituted with one or more alkyl substituents. A alkylthioalkylene is a divalent, straight or branched chain alkylthioalkane group.

As used herein, the term "heterocyclyl" refers to a stable 3- to 18-membered (i.e., 3-, 4-, 5-, 6-, 7-, 8-, 9-, 10-, 11-, 12-, 13-, 14-, 15-, 16-, 17-, 18-, 3-4-, 3-5-, 3-6-, 3-7-, 3-8-, 3-9-, 3-10-, 3-11-, 3-12-, 3-13-, 3-14-, 3-15-, 3-16-, 3-17-, 3-18-, 4-5-, 4-6-, 4-7-, 4-8-, 4-9-, 4-10-, 4-11-, 4-12-, 4-13-, 4-14-, 4-15-, 4-16-, 4-17-, 4-18-, 5-6-, 5-7-, 5-8-, 5-9-, 5-10-, 5-11-, 5-12-, 5-13-, 5-14-, 5-15-, 5-16-, 5-17-, 5-18-, 6-7-, 6-8-, 6-9-, 6-10-, 6-11-, 6-12-, 6-13-, 6-14-, 6-15-, 6-16-, 6-17-, 6-18-, 7-8-, 7-9-, 7-10-, 7-11-, 7-12-, 7-13-, 7-14-, 7-15-, 7-16-, 7-17-, 7-18-, 8-9-, 8-10-, 8-11-, 8-12-, 8-13-, 8-14-, 8-15-, 8-16-, 8-17-, 8-18-, 9-10-, 9-11-, 9-12-, 9-13-, 9-14-, 9-15-, 9-16-, 9-17-, 9-18-, 10-11-, 10-12-, 10-13-, 10-14-, 10-15-, 10-16-, 10-17-, 10-18-, 11-12-, 11-13-, 11-14-, 11-15-, 11-16-, 11-17-, 11-18-, 12-13-, 12-14-, 12-15-, 12-16-, 12-17-, 12-18-, 13-14-, 13-15-, 13-16-, 13-17-, 13-18-, 14-15-, 14-16-, 14-17-, 14-18-, 15-16-, 15-17-, 15-18-, 16-17-, 16-18-, or 17-18-membered) ring system that consists of carbon atoms and from one to five (i.e., 1, 2, 3, 4, 5, 1-2, 1-3, 1-4, 1-5, 2-3, 2-4, 2-5, 3-4, 3-5, or 4-5) heteroatoms selected from the group consisting of nitrogen, oxygen, sulfur, and silicon. The heterocyclyl may be a monocyclic or a polycyclic ring system, which may include fused, bridged, or spiro ring systems; and the nitrogen, carbon, sulfur, or silicon atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

The term "heterocyclylene" means a group obtained by removal of a hydrogen atom from a heterocyclyl group. Non-limiting examples of heterocyclylene include piperidylene, pyrrolidinylene, piperazinylene, morpholinylene, thiomorpholinylene, thiazolidinylene, 1,4-dioxanylene, tetrahydrofuranylene, and tetrahydrothiophenylene.

As used herein, the term "aryl" refers to an aromatic monocyclic or polycyclic ring system containing from 6 to 19 (i.e., 6, 7, 8, 9, 10, 11, 12, 13, 14, 15, 16, 17, 18, 19, 6-7, 6-8, 6-9, 6-10, 6-11, 6-12, 6-13, 6-14, 6-15, 6-16, 6-17, 6-18, 6-19, 7-8, 7-9, 7-10, 7-11, 7-12, 7-13, 7-14, 7-15, 7-16, 7-17, 7-18, 7-19, 8-9, 8-10, 8-11, 8-12, 8-13, 8-14, 8-15, 8-16, 8-17, 8-18, 8-19, 9-10, 9-11, 9-12, 9-13, 9-14, 9-15, 9-16, 9-17, 9-18, 9-19, 10-11, 10-12, 10-13, 10-14, 10-15, 10-16, 10-17, 10-18, 10-19, 11-12, 11-13, 11-14, 11-15, 11-16, 11-17, 11-18, 11-19, 12-13, 12-14, 12-15, 12-16, 12-17, 12-18, 12-19, 13-14, 13-15, 13-16, 13-17, 13-18, 13-19, 14-15, 14-16, 14-17, 14-18, 14-19, 15-16, 15-17, 15-18, 15-19, 16-17, 16-18, 16-19, 17-18, 17-19, or 18-19) carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylene" means a group obtained by removal of a hydrogen atom from an aryl group. Non-limiting examples of arylene include phenylene and naphthylene.

As used herein, "heteroaryl" refers to an aromatic ring that consists of carbon atoms and from one to five (i.e., 1, 2, 3, 4, 5, 1-2, 1-3, 1-4, 1-5, 2-3, 2-4, 2-5, 3-4, 3-5, or 4-5) heteroatoms selected from the group consisting of nitrogen, oxygen, sulfur, and silicon. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The term "heteroarylene" means a group obtained by removal of a hydrogen atom from a heteroaryl group. Non-limiting examples of heteroarylene include pyridylene, pyrazinylene, furanylene, thienylene, and pyrimidinylene.

The term "arylalkyl" refers to a moiety of the formula —$R^aR^b$ where $R^a$ is an alkyl or cycloalkyl as defined above and $R^b$ is an aryl or heteroaryl as defined above.

The term "arylalkylene" means a group obtained by removal of a hydrogen atom from an arylalkyl group. Non-limiting examples of arylalkylene include phenylmethylene, phenylethylene, and phenylpropylene.

As used herein, the term "acyl" means a moiety of formula R-carbonyl, where R is an alkyl, cycloalkyl, aryl, or heteroaryl as defined above. Exemplary acyl groups include formyl, acetyl, propanoyl, benzoyl, and propenoyl.

The term "halogen" means fluorine, chlorine, bromine, or iodine.

The term "thiol" means a moiety of formula —SH.

The term "aldehyde" means a moiety of formula —C(O)H.

The term "ketone" means a moiety of formula —C(O)R, where R is a $C_{1-8}$ (i.e., $C_1$, $C_2$, $C_3$, $C_4$, $C_5$, $C_6$, $C_7$, $C_8$, $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{2-7}$, $C_{2-8}$, $C_{3-4}$, $C_{3-5}$, $C_{3-6}$, $C_{3-7}$, $C_{3-8}$, $C_{4-5}$, $C_{4-6}$, $C_{4-7}$, $C_{4-8}$, $C_{5-6}$, $C_{5-7}$, $C_{5-8}$, $C_{6-7}$, $C_{6-8}$, or $C_{7-8}$) alkyl, $C_{3-8}$ (i.e., $C_3$, $C_4$, $C_5$, $C_6$, $C_7$, $C_8$, $C_{3-4}$, $C_{3-5}$, $C_{3-6}$, $C_{3-7}$, $C_{3-8}$, $C_{4-5}$, $C_{4-6}$, $C_{4-7}$, $C_{4-8}$, $C_{5-6}$, $C_{5-7}$, $C_{5-8}$, $C_{6-7}$, $C_{6-8}$, or $C_{7-8}$ cycloalkyl, aryl, heteroaryl, heterocyclyl, or arylalkyl.

The term "amide" means a group having the formula —C(O)N($R^1$)($R^1$) or —C(O)N($R^1$)—. Amides include, e.g., —C(O)N(R)R—, —R—C(O)N($R^1$)R—, —CHR—C(O)N(R)R—, and —C(R)($R^1$)—C(O)N($R^1$)R—. Each R can be independently selected from the group consisting of a bond, $C_{1-8}$ alkylene, $C_{2-8}$ alkenylene, arylene, and heteroarylene, and each $R^1$ can be independently selected from the group consisting of hydrogen, $C_{1-8}$ alkyl, $C_{2-8}$ alkenyl, $C_{2-8}$ alkynyl, $C_{3-8}$ cycloalkyl, aryl, heteroaryl, heterocyclyl, and arylalkyl. Exemplary amides include, but are not limited to, —$C_{1-8}$ alkylene-C(O)N(aryl)-, —$C_{2-8}$ alkenylene-C(O)N(aryl)-, and —$C_{1-8}$ alkylene-C(O)N($C_{1-8}$ alkyl)- (e.g., —(CH$_2$)$_2$—C(O)N(CH$_3$)—).

The term "amine" refers to radicals of the general formula —NRR', wherein R and R' are independently selected from the group consisting of hydrogen, alkyl, aryl, and heteroaryl. Examples of amino groups include: —NH$_2$, —NHCH$_3$, —N(CH$_2$CH$_3$)$_2$, and —NHPh.

The term "alcohol" means a moiety of formula —COH.

The term "alkoxy" means groups of from 1 to 8 (i.e., 1, 2, 3, 4, 5, 6, 7, 8, 1-2, 1-3, 1-4, 1-5, 1-6, 1-7, 1-8, 2-3, 2-4, 2-5, 2-6, 2-7, 2-8, 3-4, 3-5, 3-6, 3-7, 3-8, 4-5, 4-6, 4-7, 4-8, 5-6, 5-7, 5-8, 6-7, 6-8, or 7-8) carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

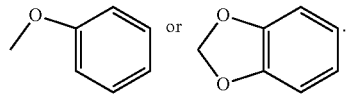

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three (i.e., 0, 1, 2, 3, 0-1, 0-2, 0-3, 1-2, 1-3, or 2-3) H atoms in each residue can be replaced with alkyl, halogen, haloalkyl, hydroxy, lower-alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Avobenzone-dendrimer conjugates of the present invention may be made using methods in the art. Suitable methods include those shown in Scheme 1 and described in Examples 2-7 below.

Scheme 1

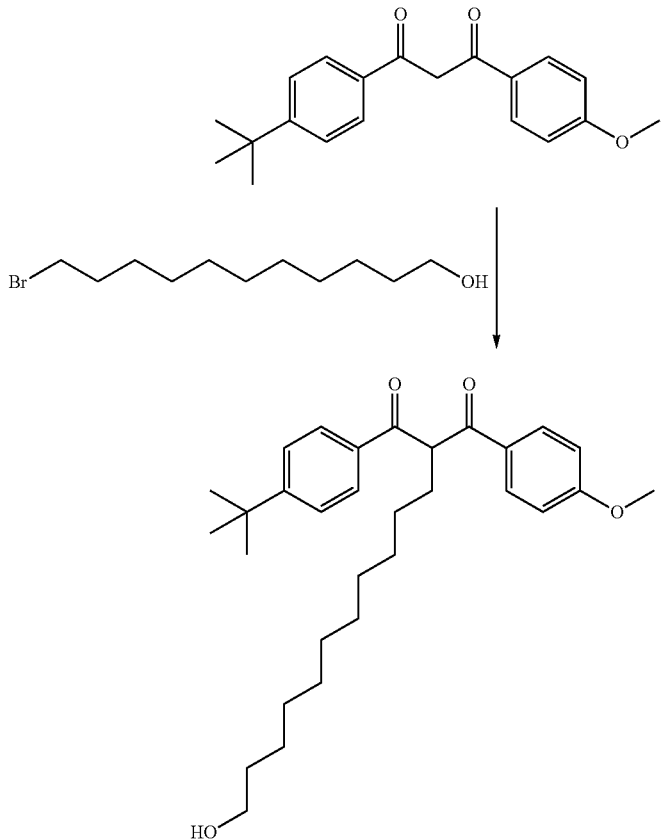

-continued

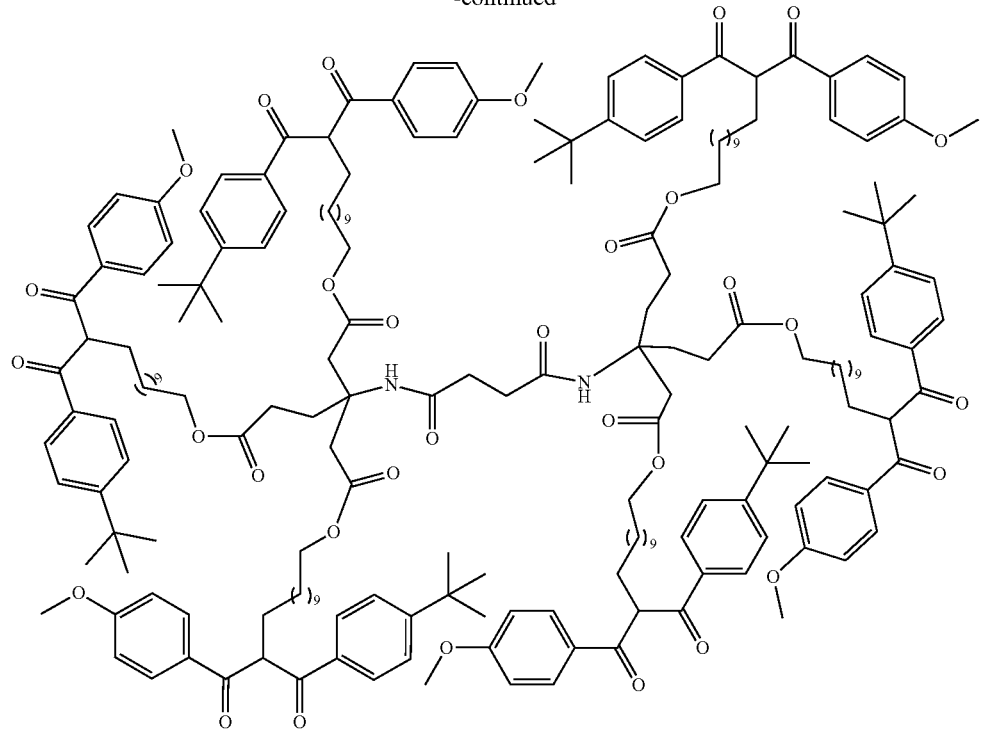

The present invention is further directed to a sunscreen formulation. This sunscreen formulation comprises an avobenzone-dendrimer conjugate according to the present invention and a dermatologically acceptable vehicle. Suitable avobenzone-dendrimer conjugates include those described above. As will be apparent to the skilled artisan, the formulation can include a single type of conjugate or a mixture of one or more different types of conjugate. In at least one embodiment of the sunscreen formulation, contains G1N, G2N, G2P, or any combination thereof.

The sunscreen formulations of the present invention can be formulated into a wide variety of product types, including creams, dispersions, emulsions (oil-in-water, water-in-oil, water-in-oil-in-water, and oil-in-water-in-silicone), gels, ointments, lotions, milks, mousses, sprays, tonics, and the like.

The sunscreen formulations of the present invention typically comprise a carrier (vehicle or diluent) or mixture of carriers. The carrier should be cosmetically and/or pharmaceutically acceptable, which reflects that the carrier is suitable for topical application onto the skin, and has good aesthetic properties. The carriers and additional components used to formulate such products vary with the product type and may be routinely chosen by one skilled in the art. The following is a description of some of these carriers and additional components.

The formulations can comprise a carrier, or a mixture of carriers, suitable for topical application onto human skin. The carrier(s) typically constitute(s) from about 0.5% to about 99.5% by weight, preferably from about 5.0% to about 99.5% by weight, more preferably from about 10.0% to about 98.0% by weight, of the formulation. As used herein, the phrase "suitable for topical application onto human skin" reflects that the carrier does not damage or negatively affect the aesthetics of or cause irritation to human skin.

Carriers suitable for use with the present invention include, for example, those used in the formulation of a wide variety of product types, including creams, dispersions, emulsions, gels, lotions, milks, mousses, sprays, and tonics.

The carriers used herein can include a wide range of components conventionally used in cosmetic/dermatological compositions. The carriers can contain a solvent to dissolve or disperse the sunscreen formulation. The carriers can also contain a wide variety of additional materials including, but not limited to, esters (such as isopropyl myristate), halogenated hydrocarbons (such as freons), hydrocarbons (such as decene, hexane, and isobutane), linalool, volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, dimethicone), alkyl derivatives of benzoic and hydroxybenzoic acid, and mixtures thereof.

Mousses and aerosol sprays can also include any of the conventional propellants to deliver the material as a foam, in the case of a mousse, or as a fine, uniform spray, in the case of an aerosol spray. Examples of suitable propellants include materials such as hydrofluorinated compounds, dichlorodifluoromethane, difluoroethane, dimethylether, isobutane, n-butane, propane, or trichlorofluromethane. A tonic or spray product having a low viscosity may also include an emulsifying agent. Examples of suitable emulsifying agents are anionic surfactants, cationic surfactants, nonionic surfactants, and mixtures thereof. Fluorosurfactants are especially preferred, particularly if the product is a spray composition and most especially if it is a spray composition having a relatively low level of volatile organic solvents, such as alcohols, and relatively high levels of water (i.e., in excess of about 10%, by weight, water). If such an emulsifying agent is included, it is preferably present at a level of from about 0.01% to about 7.5% by weight of the formulation. The level of propellant can be adjusted as desired, but is generally from about 3% to about 30% by weight of mousse compositions and from about 15% to about 50% by weight of the aerosol spray compositions.

Suitable spray compositions are well known in the art and include conventional, non-aerosol pump sprays, i.e., "atomizers," aerosol containers or cans having propellant, as described above, and also pump aerosol containers utilizing compressed air as the propellant. Pump aerosol containers are disclosed, for example, in U.S. Pat. No. 4,077,441 to Olofsson and U.S. Pat. No. 4,850,517 to Stege, each of which is hereby incorporated by reference in its entirety.

A wide variety of additional components can be employed in the sunscreen formulations herein. For example, the formulations of the present invention can comprise pharmaceutical additives or adjuvants.

Useful pharmaceutical active agents which may be conjointly administered according to the present invention include antimicrobial drugs: antibacterials, antifungals, antiprotozoans, and antivirals. Antimicrobial drugs preferred for inclusion in compositions of the present invention comprise pharmaceutically acceptable salts of β-lactam drugs, amantadine, amikacin, capreomycin, chlorhexidine, chlortetracycline, ciprofloxacin, clindamycin, doxycycline, erythromycin, ethambutol, gentamicin, kanamycin, lineomycin, methacycline, methenamine, metronidazole, miconazole, minocycline, neomycin, netilmicin, norfloxacin, oxytetracycline, paramomycin, pentamidine, quinolone drugs, streptomycin, tetracycline, tobramycin, and triclosan.

The subject formulations can contain various emulsifiers when formulated as emulsions. These emulsifiers are useful for emulsifying the various carrier components of the formulations herein. Suitable emulsifiers can include any of a wide variety of nonionic, cationic, anionic, and zwitterionic emulsifiers disclosed in the prior patents and other references (see, e.g., McCutcheon's 2017, Vol. 1: Detergents and Emulsifiers (North Am. ed. 2017); U.S. Pat. No. 5,011,681 to Ciotti et al.; U.S. Pat. No. 4,421,769 to Dixon et al.; U.S. Pat. No. 3,755,560 to Dickert et al., each of which is hereby incorporated by reference in its entirety).

Suitable emulsifier types include acyl lactylates, alkyl phosphates, carboxylic acid copolymers, esters and ethers of glucose, esters of glycerin, esters of propylene glycol, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps, and mixtures thereof.

Preferred emulsifiers can include, but are not limited to, ceteareth-20, ceteth-10, cetyl phosphate, diethanolamine cetyl phosphate, glyceryl stearate, PEG-100 stearate, polyethylene glycol 20 sorbitan monolaurate, polyethylene glycol 5 soya sterol, polysorbate 60, polysorbate 80, potassium cetyl phosphate, PPG-2 methyl glucose ether distearate, steareth-20, and mixtures thereof.

The sunscreen formulations can also contain various emollients. Examples of suitable emollients include, but are not limited to, highly branched hydrocarbons, non-polar carboxylic acid and alcohol esters, volatile and non-volatile silicone oils, and mixtures thereof (see, e.g., U.S. Pat. No. 4,919,934 to Deckner et al., which is hereby incorporated by reference in its entirety).

A variety of additional components can be incorporated into the subject sunscreen formulations. Non-limiting examples of these additional components include cationic polymers and thickeners, chelators, gums and thickeners, low pH thickening agents, polymers and materials for enhancing the film-forming and waterproofing properties and substantivity of the composition, sequestrants, skin penetrating aids, suspending agents, vitamins and derivatives thereof, preservatives and aesthetic components.

Exemplary film formers that, upon drying, produce a continuous film on skin are described at 2 International Cosmetic Ingredient Dictionary and Handbook 1636-38 ($7^{th}$ ed. 1997), which is hereby incorporated by reference in its entirety. These include, for example, various (meth)acrylate (co)polymers, polyvinyl alcohol, vinyl pyrrolidone (co)polymers, etc.

Exemplary preservatives, which are conventional in the art and which prevent or retard microbial growth and thus protect sunscreen formulations from spoilage, are set forth at 2 International Cosmetic Ingredient Dictionary and Handbook 1654 & 1655 ($7^{th}$ ed. 1997), which is hereby incorporated by reference in its entirety.

The sunscreen formulations of the present invention can be administered in conventional fashion to provide the desired benefit. Such methods of use generally involve topical application of an effective amount of the formulation onto the skin, which then is allowed to remain until absorbed into or removed from the skin.

The present invention may be further illustrated by reference to the following examples.

EXAMPLES

The following Examples are intended to illustrate, but by no means are intended to limit, the scope of the present invention as set forth in the appended claims.

Example 1—Materials and Methods

All chemicals were purchased from Sigma-Aldrich, Acros Organics, Alfa Aesar, Dendritech, or TCI international and used as received unless otherwise noted. Second generation Newkome-type dendrimer, aminononaester, succinate nonaester, and first generation Newkome-type acid dendrimer were synthesized as previously reported (Newkome et al., Chem. Rev. 110:6338-42 (2010), which is hereby incorporated by reference in its entirety) from starting materials purchased from Frontier Scientific. Dialysis membranes (SpectraPor 6) were purchased from Spectrum Labs and used after rinsing the membrane in water for 30 minutes. LC-MS data were recorded on an Agilent LCMSD Trap XCT spectrometer using electrospray ionization (ESI) and methanol as eluent for starting compounds and acetonitrile (0.1% TFA) for species purified by HPLC. $^1$H NMR spectra were recorded using a Bruker AV-400, -500, or -600 spectrometer (operating at 400.1 MHz, 500.2 MHz, or 600.2 MHz respectively). Chemical shifts are reported in ppm and the residual signals of the deuterated solvents were used as references. $^{13}$C NMR spectra were recorded on a Bruker AV-400 spectrometer (100 MHz). Deuterated solvents were purchased from Cambridge Isotope Laboratories.

Example 2—Synthesis of Avobenzone with Linker

Figure 5:
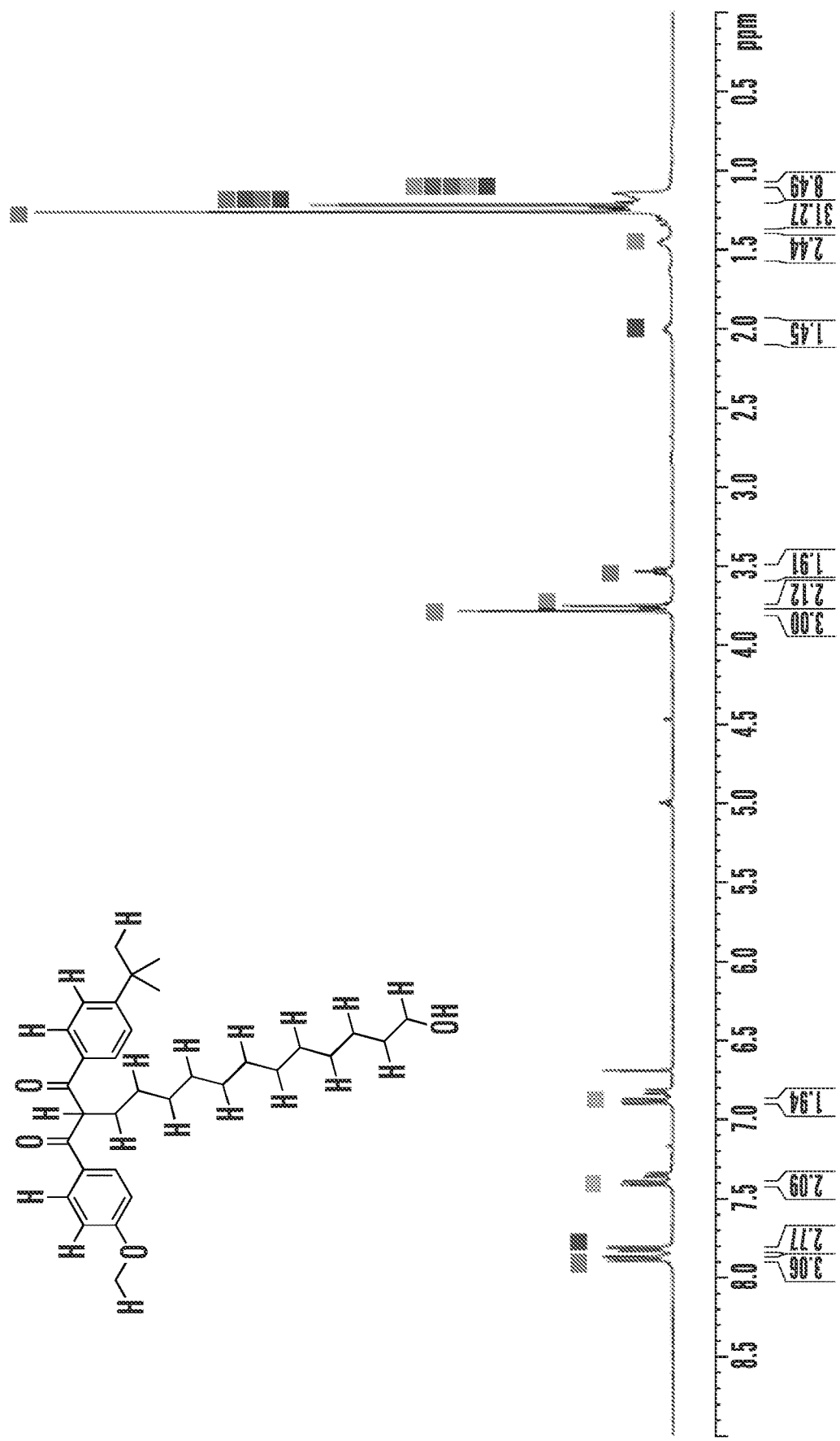
FIG. 5 is the $^1$H NMR spectrum of avobenzone with linker.
Figure 6:
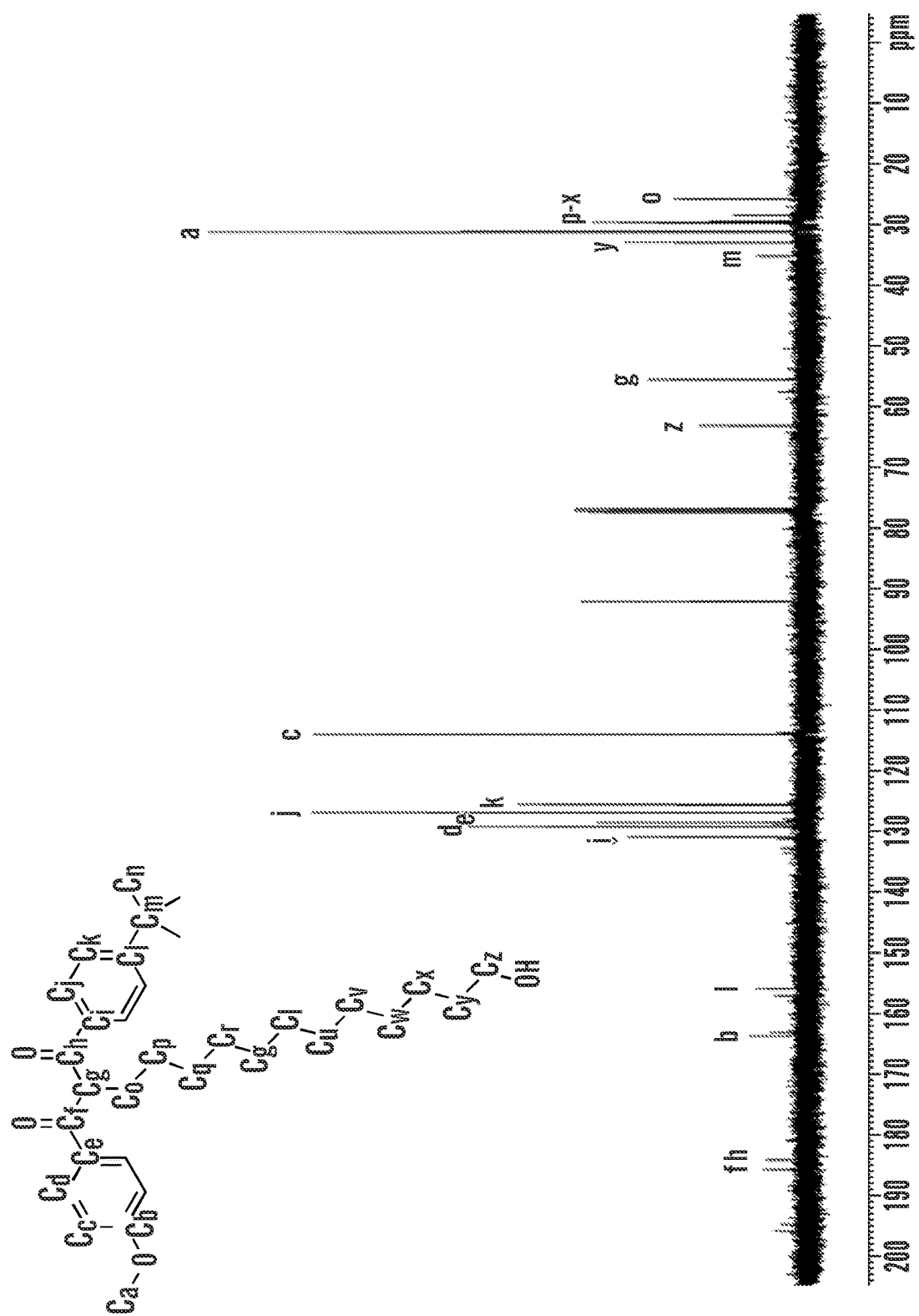
FIG. 6 is the $^{13}$C NMR spectrum of avobenzone with linker.
Figure 7:
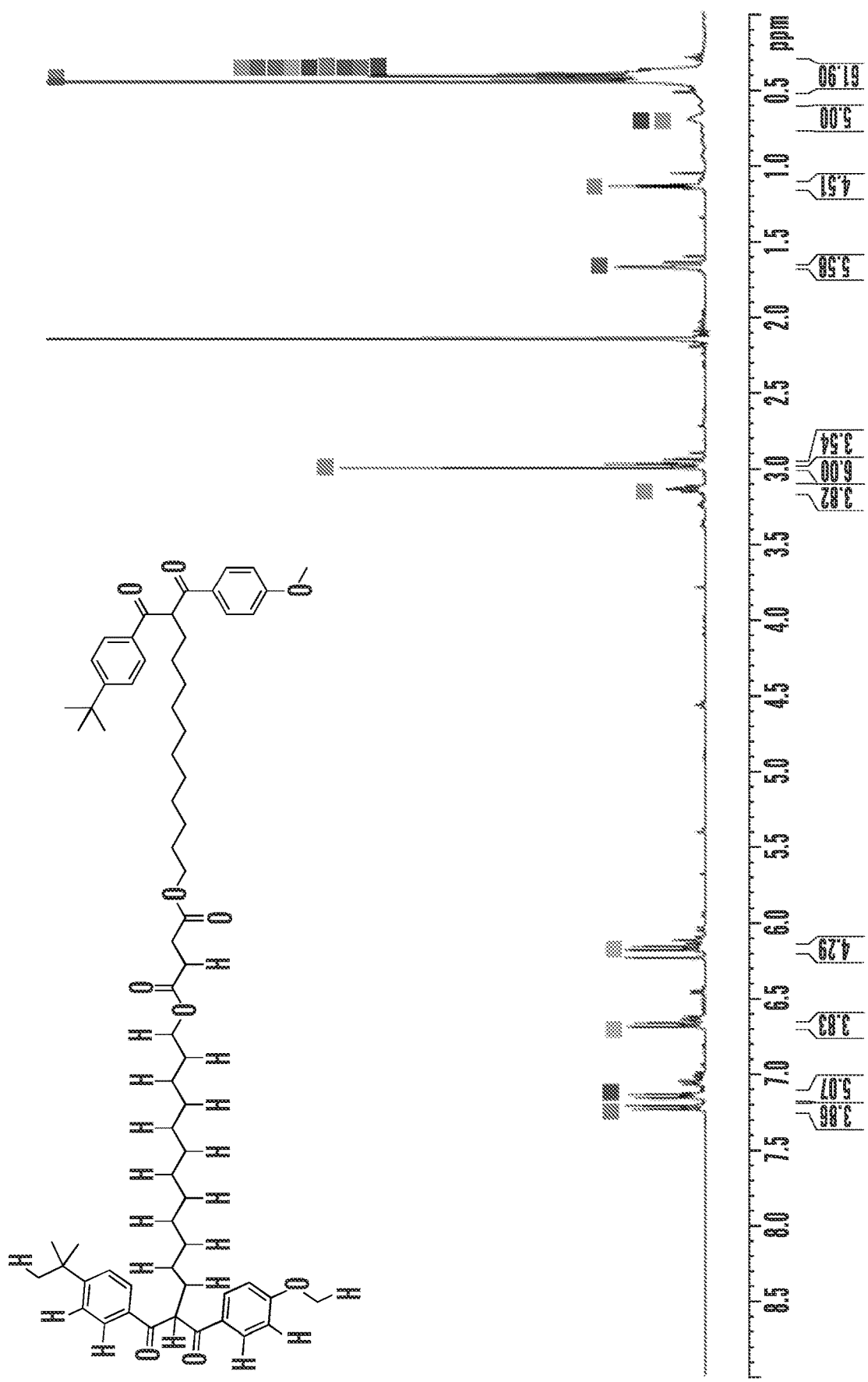
FIG. 7 is the $^1$H NMR spectrum of G0 avobenzone conjugate.
Figure 8:
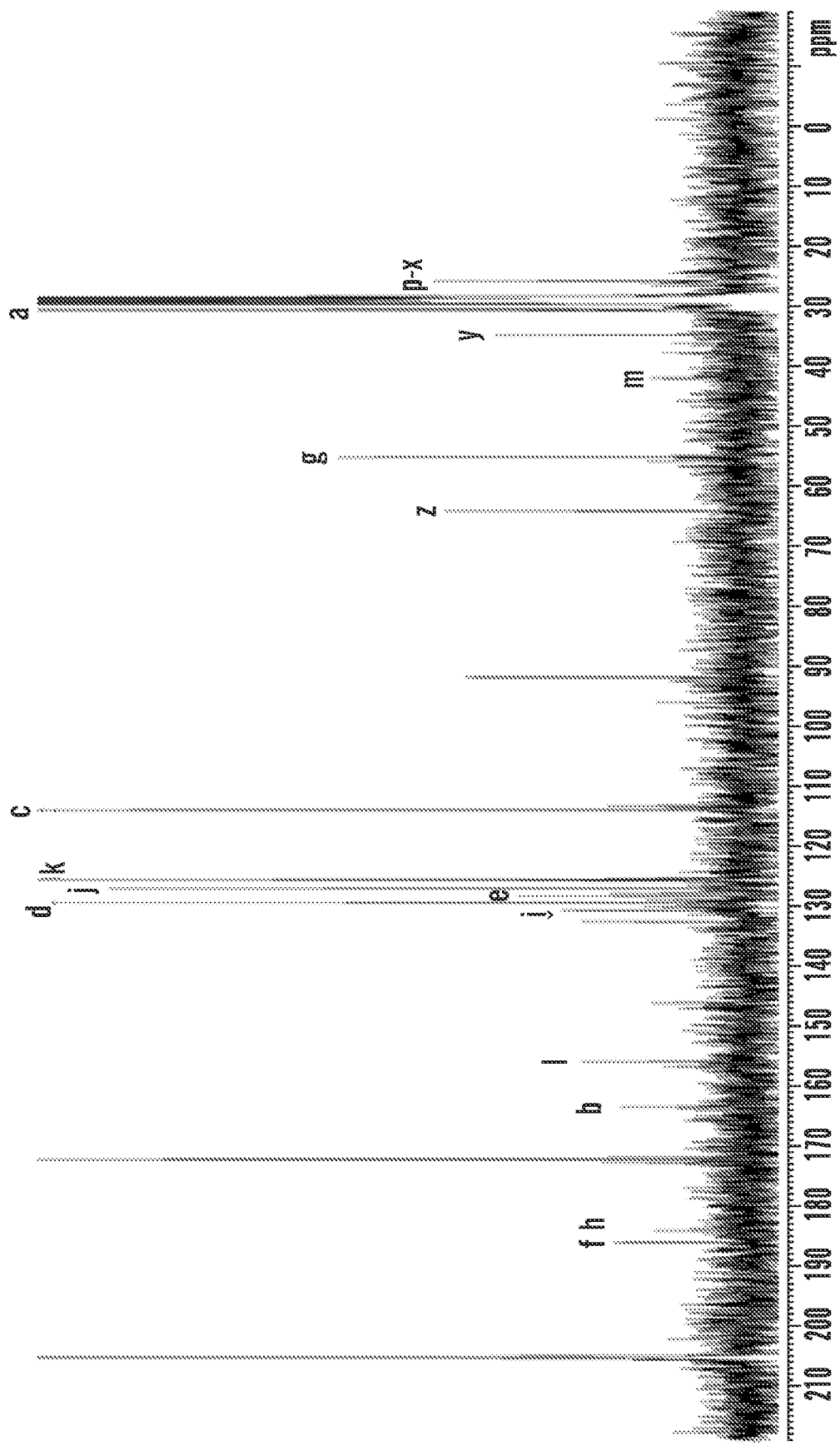
FIG. 8 is the $^{13}$C NMR spectrum of G0 avobenzone conjugate.
Figure 8:
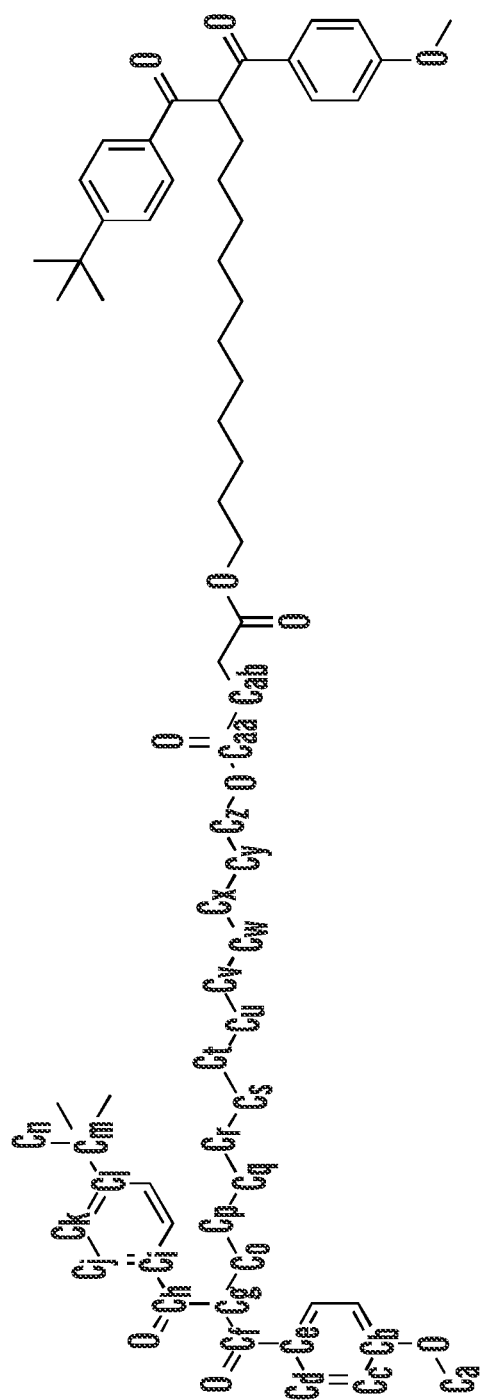
Figure 9:
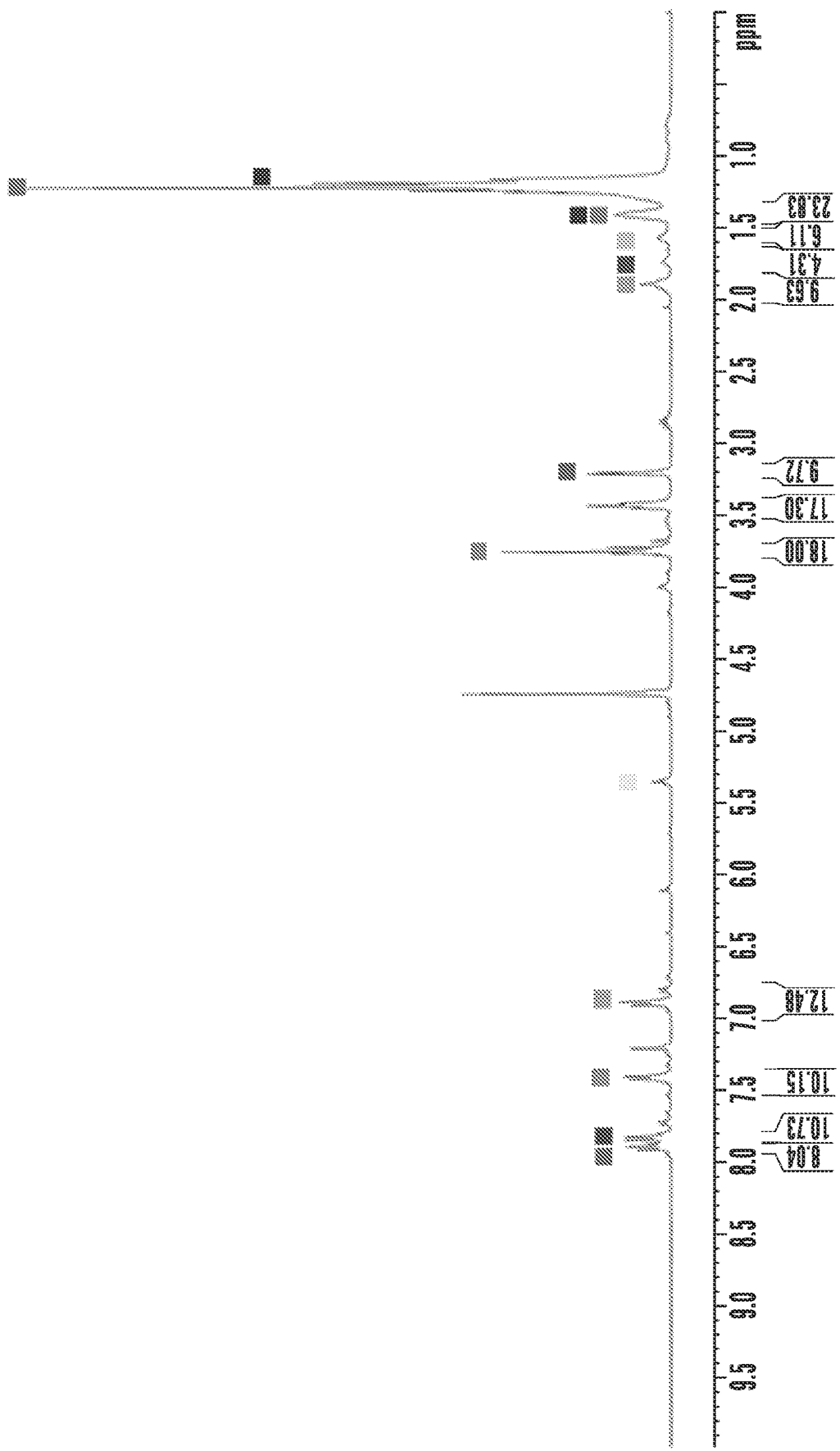
FIG. 9 is the $^1$H NMR spectrum of G1 Newkome-type avobenzone conjugate.
Figure 9:
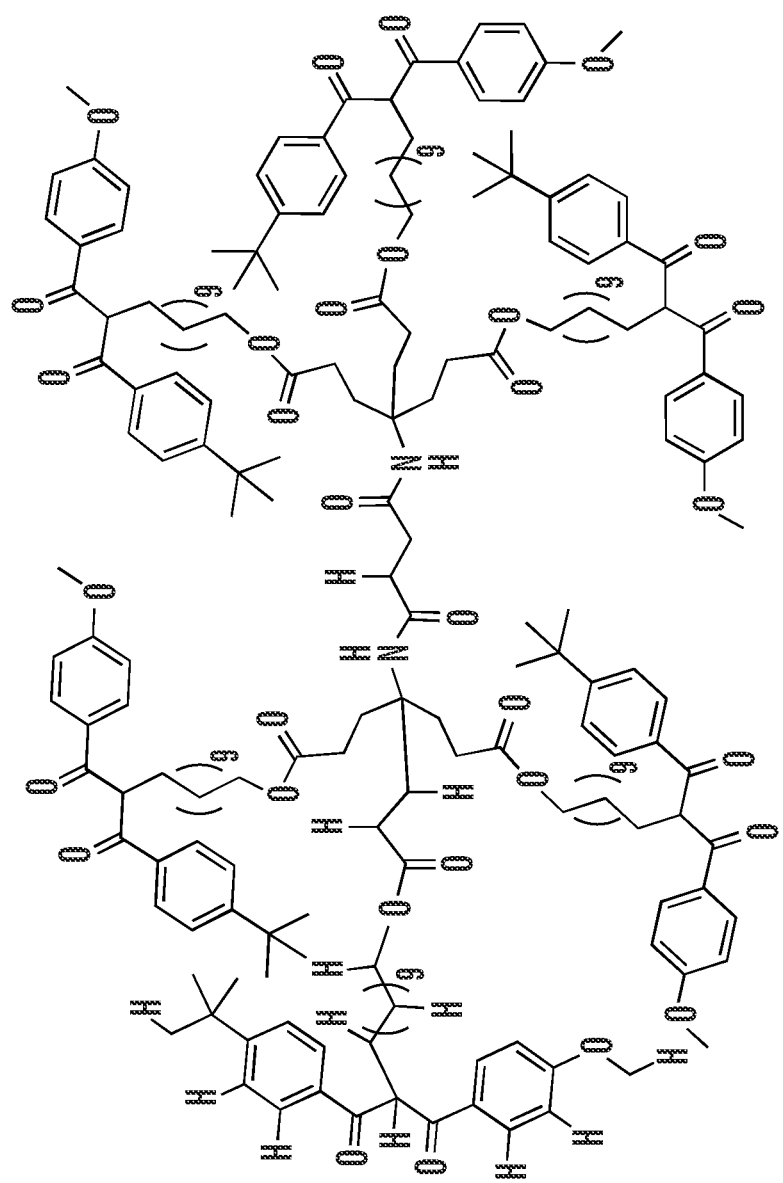
Figure 10:
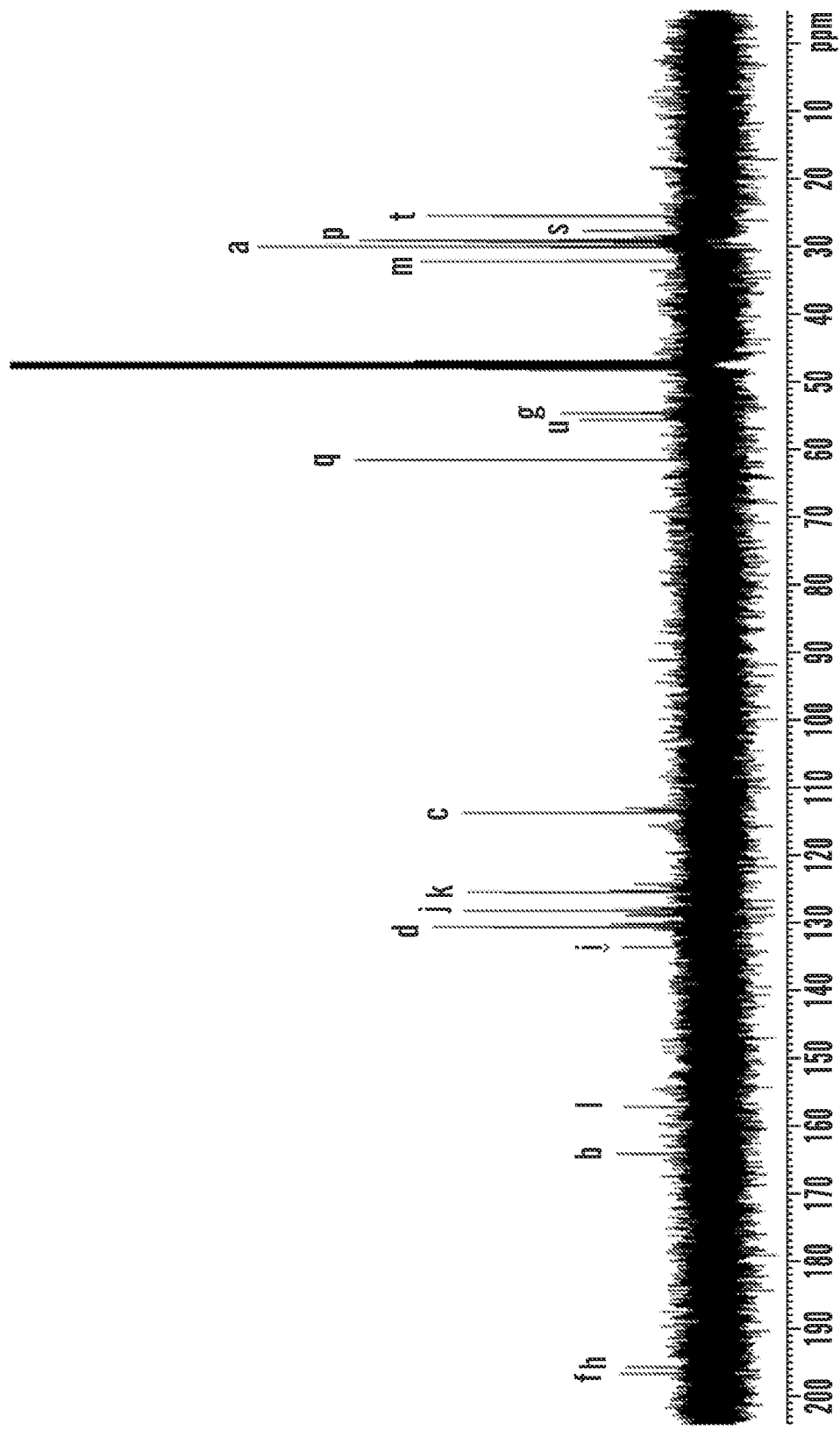
FIG. 10 is the $^{13}$C NMR spectrum of G1 Newkome-type avobenzone conjugate.
Figure 10:
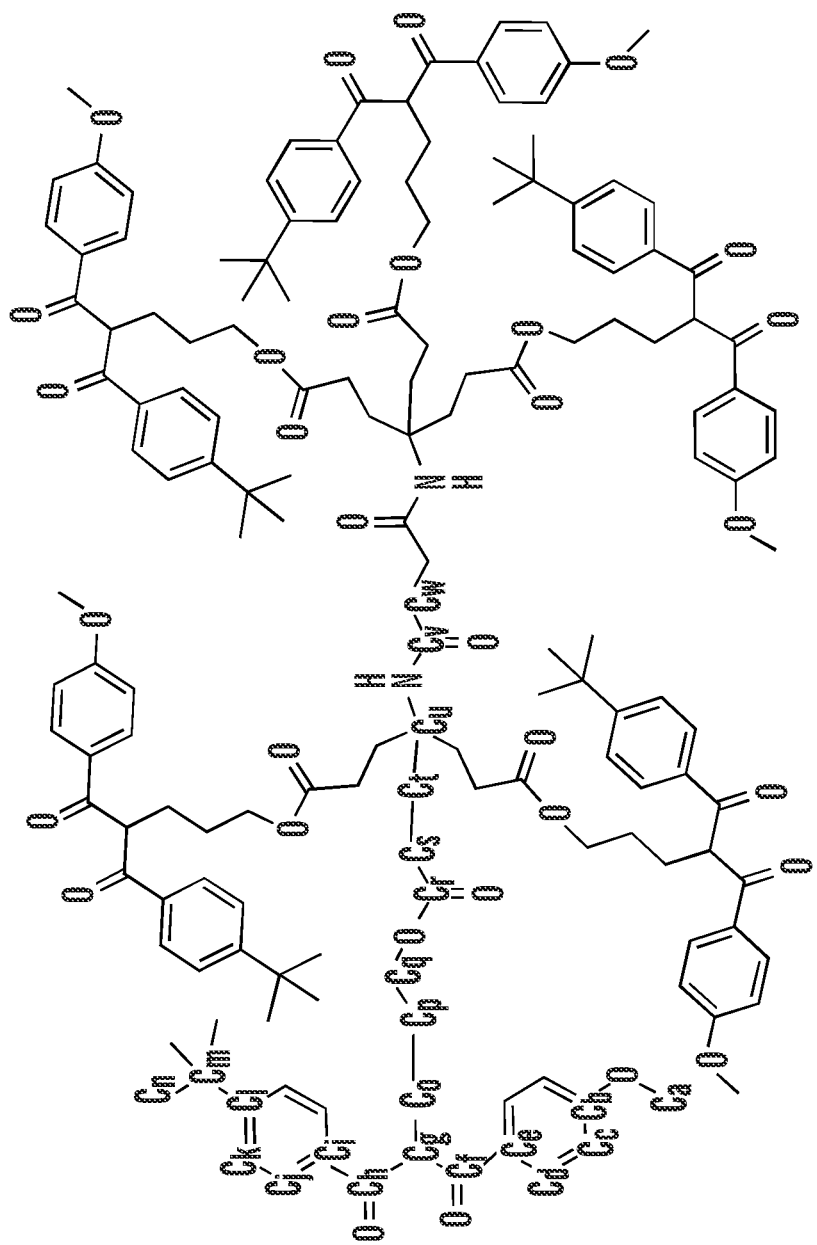

Avobenzone (0.501 g 1.61 mol) was placed in a microwave reaction vessel with 11-bromoundecanol (0.702 g 2.78 mmol). This was dissolved in DMF (4 mL) and 1,8-diazabicyclo[5.4.0]undec-7-ene (2 mL) was added. This was placed in the microwave and reacted for four hours at 70° C. followed by two days at room temperature. Condensation yielded a yellow oil that was taken up in ethyl acetate and rinsed three times with water and dried. The compound was purified with silica gel column chromatography 1:1 hexanes: ethyl acetate. Condensation yielded a yellow oil (0.441 g, 57%). $^1$H-NMR (FIG. 4-5) (400 MHz, CDCl$_3$, $\delta_{ppm}$): 7.89 (app d, J=8.8 Hz, 2H, C$_q$C$_q$CHArH, diketo); 7.83 (app d, J=8.8 Hz, 2H, OC$_q$ArH, diketo); 7.42 (app d, J=6.8 Hz, 2H, C$_q$C$_q$HArH, diketo); 6.90 (app d, J=7.2 Hz, 2H, OC$_q$ArH, diketo); 3.79 (s, 3H, OCH$_3$); 3.76, (t, J=2.8, CH$_2$OH); 3.54 (m, 1H, OC$_q$CHC$_q$O, diketo); 2.04 (q, J=2.8, 2H CH$_2$CH$_2$OH); 1.46 (m, 2H, CHCH$_2$); 1.27-1.22 (m, C$_q$(CH$_3$)$_3$ and (CH$_2$)$_9$). $^{13}$C-NMR (FIG. 4-6) (100 MHz, CDCl$_3$ $\delta_{ppm}$): 185.8 (COCH); 184.2 (COCH); 163.7 (CHOC, diketo); 155.9 (C(CH$_3$)$_3$C); 130.9 (ArC$_q$); 129.2 (ArC$_q$); 128.5 (ArC); 126.9 (ArC); 125.7 (ArC); 113.9 (ArC); 63.0 (CH$_2$OH); 55.4 (OC$_q$CHC$_q$O); 35.0 (C(CH$_3$)$_3$); 32.8 (CH$_2$CH$_2$OH); 31.1 (CH$_3$O); 29.6-28.3 (CH$_2$)$_9$; 25.7 (CHCH$_2$). MS-ESI (M+Na)$^+$ m/z calcd for C$_{31}$H$_{44}$O$_4$: 481.2 found 481.3.

Example 3—Synthesis of Zero Generation Newkome-Type Dendrimer Avobenzone Conjugate Avobenzone with linker (0.130 g, 0.270 mmol) was added to a flask containing succinic anhydride (0.100 g, 1 mmol). The mixture was dissolved in acetone (10 mL) and DIPEA (0.2 mL) was added. This was reacted for 12 hours. The condensation yielded a white solid that was dissolved in ether and washed with water. Condensation yielded a yellow solid (0.200 g, 0.344 mmol) of avobenzone with linker (0.150 g, 0.312 mmol). 1-Ethyl-3-(3-dimethylaminopropyl) carbodiimide (0.500 g, 3.22 mmol) (EDC) was added to the recovered product. This mixture was dissolved in DMF (12 mL) and DIPEA (1 mL) was added. The reaction mixture yielded a yellow oil that was taken up in ethyl acetate and rinsed three times with water and dried. The compound was purified with silica gel preparation thin chromatography (1:1 hexanes:ethyl acetate) yielding a yellow oil (0.075 g, 22.4%). $^1$H-NMR (FIG. 4-7) (400 MHz, Acetone, $\delta_{ppm}$): 7.24 (app d, J=8.8 Hz, 2H, C$_q$C$_q$CHArH, diketo); 7.16 (app d, J=8.8 Hz, 2H, OC$_q$ArH, diketo); 6.69 (app d, J=6.8 Hz, 2H, C$_q$C$_q$HArH, diketo); 6.24 (app d, J=7.2 Hz, 2H, OC$_q$ArH, diketo); 3.16, (t, J=6, CH$_2$OH); 3.00 (s, 3H, OCH$_3$); 3.54 (m, 1H, OC$_q$CHC$_q$O, diketo); 1.68 (s, 4H, OC$_q$OCH$_2$); 1.51 (q, J=2.8, 2H CH$_2$CH$_2$OH); 0.76 (m, 2H, CHCH$_2$), 0.46-0.41 (m, C$_q$(CH$_3$)$_3$ and (CH$_2$)$_9$). $^{13}$C-NMR (FIG. 4-8) (100 MHz, CDCl$_3$ $\delta_{ppm}$): 186.1 (COCH); 172.7 (C$_q$OO); 163.5 (CH$_3$OC, Diketo); 155.9 (C(CH$_3$)$_3$C); 132.6 (ArC$_q$); 128.3 (ArC$_q$); 127.9 (ArC); 127.0 (ArC); 125.4 (ArC); 114.0 (ArC); 64.0 (CH$_2$OH); 55.0 (OC$_q$CHC$_q$O); 34.7 (C(CH$_3$)$_3$); 32.8 (CH$_2$CH$_2$OH); 31.1 (CH$_3$O); 25.1 (CHCH$_2$). MS-ESI (M+Na)$^+$ m/z calcd for C$_{67}$H$_{92}$O$_{10}$: 1066.67 found 1065.8.

Figure 11:
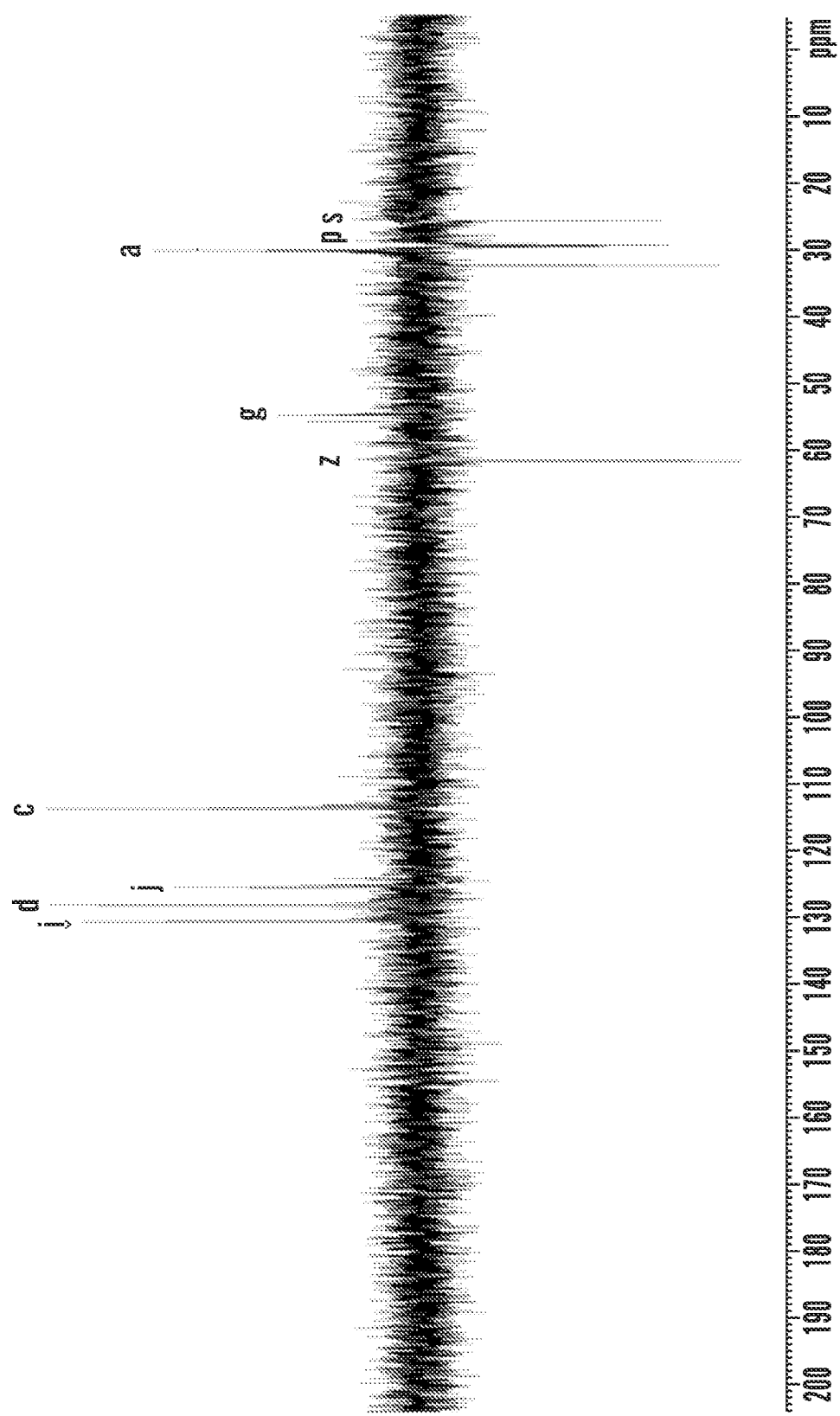
FIG. 11 is the $^{13}$C Dept-135 spectrum of G1 Newkome-type avobenzone conjugate.
Figure 11:
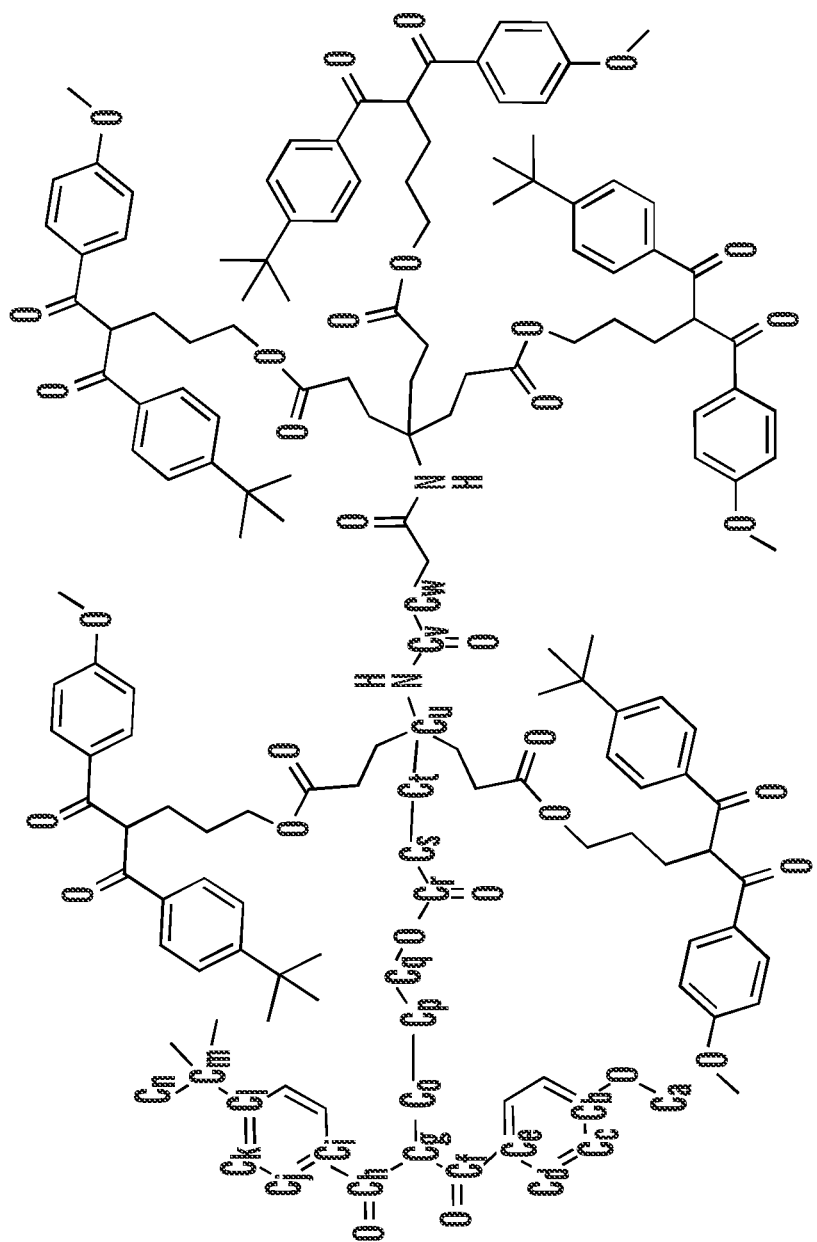

Example 4—Synthesis of First Generation Newkome-Type Dendrimer Avobenzone Conjugate Avobenzone with linker (0.900 g, 1.87 mmol) was added to a flask containing first generation Newkome-type acid dendrimer (0.184 g, 0.319 mmol) and EDC (0.600 g 3.84 mmol). The mixture was dissolved in DMF (15 mL) and DIPEA (2 mL). Condensation of the reaction mixture yielded a yellow oil which was taken up in ethyl acetate and rinsed three times with water and dried. The compound was purified with silica gel preparation thin chromatography 1:1 hexanes:ethyl acetate to yield a yellow oil (0.150 g, 13.6%). $^1$H-NMR (FIG. 4-9) (400 MHz, MeOD, $\delta_{ppm}$): 7.92 (app d, J=8.8 Hz, 12H, C$_q$C$_q$CHArH, diketo); 7.87 (app d, J=8.8 Hz, 12H, OC$_q$Ar, diketo); 7.42 (app d, J=6.8 Hz, 12H, C$_q$C$_q$HArH, diketo); 6.91 (app d, J=7.2 Hz, 12H, OC$_q$ArH, diketo); 5.37 (br, OC$_q$NH); 3.77 (s, 18H, OCH$_3$); 3.22 (m, 1H, OC$_q$CHC$_q$O, diketo); 2.06 (br, 6H, OC$_q$OCH$_2$CH$_2$); 1.92 (s, 4H, OC$_q$OCH$_2$); 1.74 (br, 6H, OC$_q$OCH$_2$CH$_2$); 1.41 (m, 2H CH$_2$CH$_2$OH and (CH$_2$)$_9$); 1.25-1.17 (m, C$_q$(CH$_3$)$_3$ and (CH$_2$)$_9$). $^{13}$C-NMR (FIG. 4-10) (100 MHz, MeoD $\delta_{ppm}$): 196.7 (COCH); 195.7 (COCH); 164.2 (CH$_3$OC, Diketo); 156.2 (C(CH$_3$)$_3$C), 133.6 (ArC$_q$); 130.7 (ArC$_q$); 130.3 (ArC); 128.9 (ArC); 125.6 (ArC); 113.8 (ArC); 61.6 (CH$_2$OH); 55.6 (CH$_2$C$_q$); 54.7 (OC$_q$CHC$_q$O); 32.2 (C(CH$_3$)$_3$); 32.8 (CH$_2$CH$_2$OH); 30.2 (CH$_3$O); 30.9-29.0 (CH$_2$)$_9$; 27.6 (CHCH$_2$); 25.4 (CH$_2$CH$_2$) MS-ESI (M+2Na$^+$/ 2)$^+$ m/z calcd for C$_{210}$H$_{294}$N$_2$O$_{38}$Na: 1751.96 found 1751.0. (See FIG. 11 for the $^{13}$C Dept-135 spectrum.)

Figure 2:
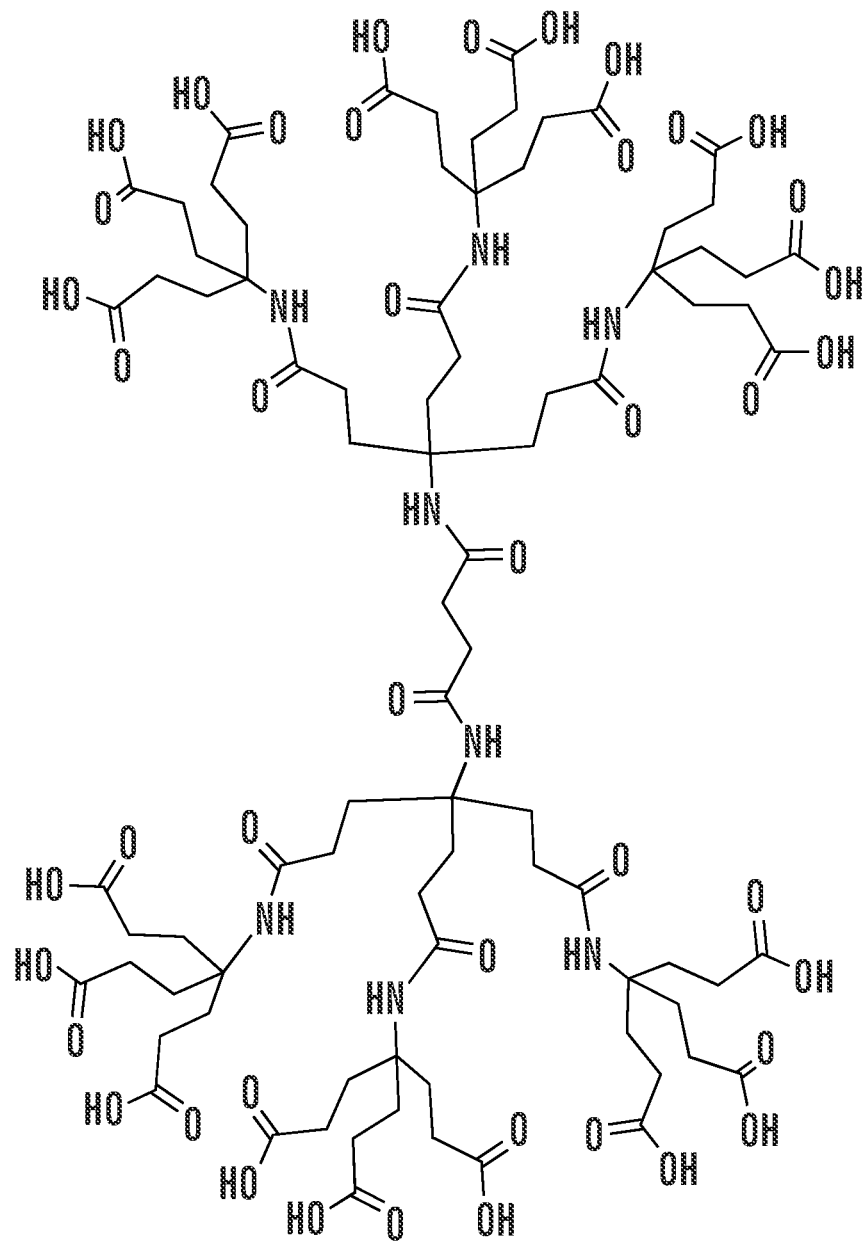
FIG. 2 shows second generation (G2) Newkome type dendrimer (left) and G2 succinated PAMAM dendrimer (right).
Figure 2:
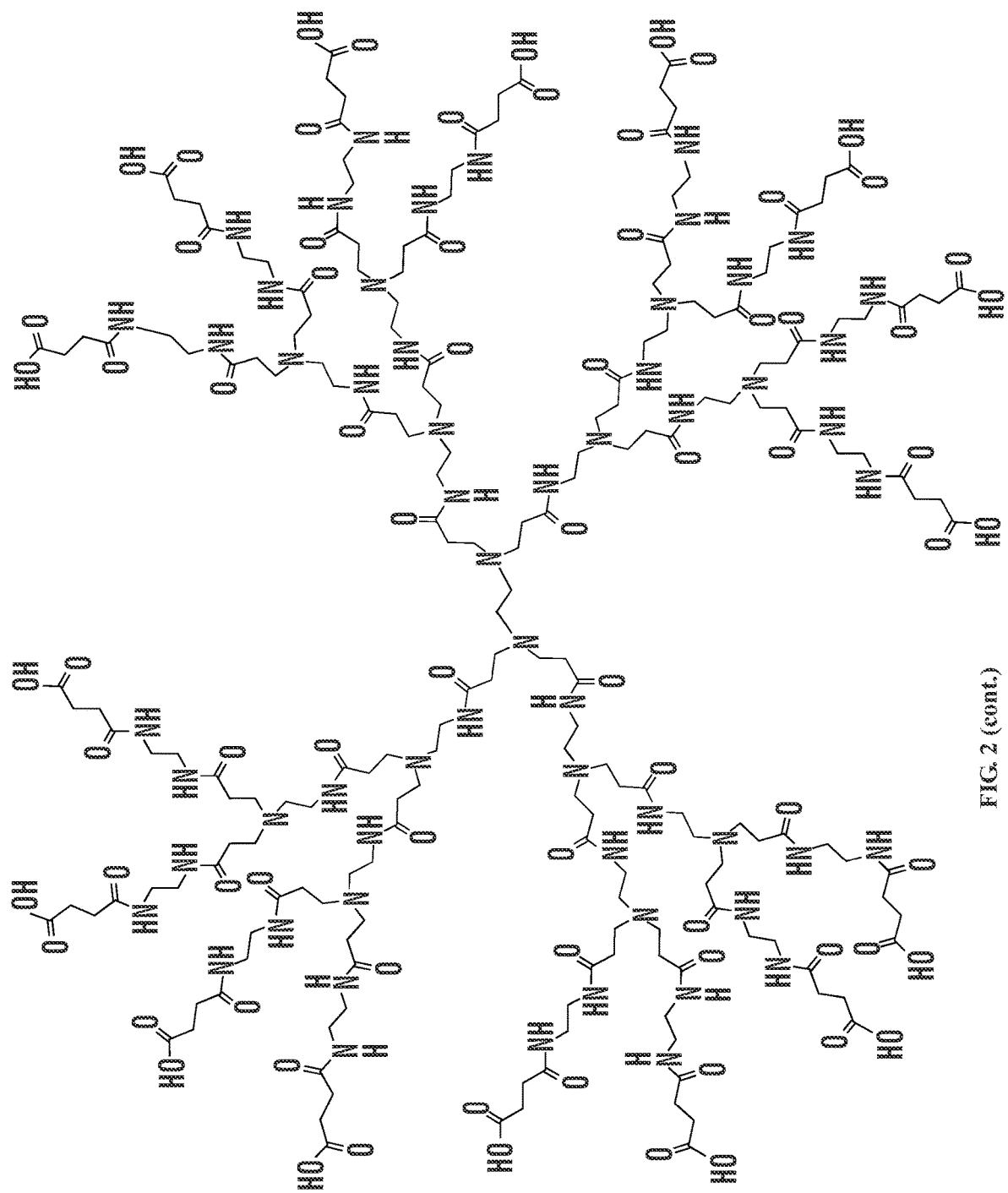
Figure 12:
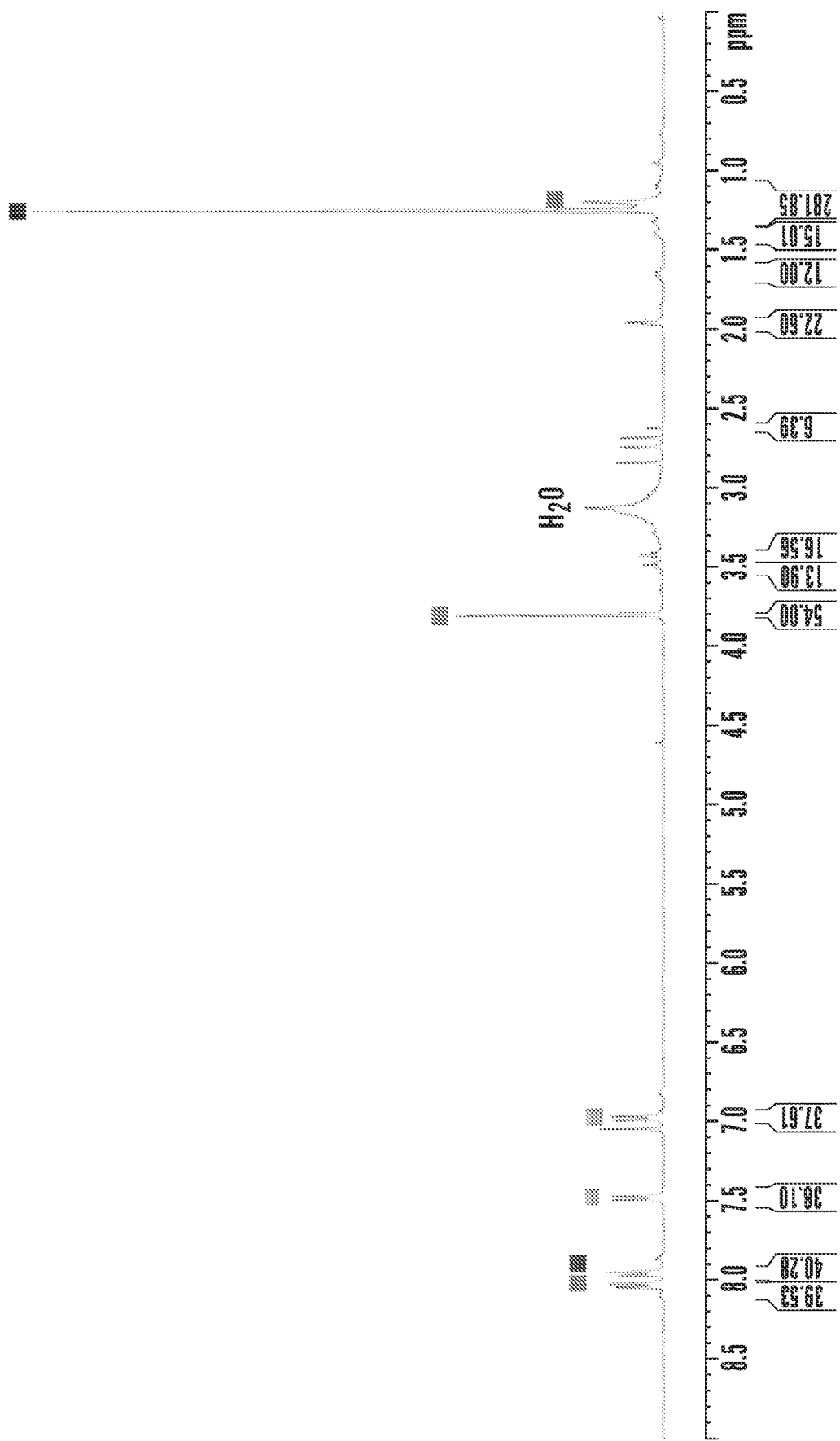
FIG. 12 is the $^1$H NMR spectrum of G2 Newkome-type avobenzone conjugate.
Figure 12:
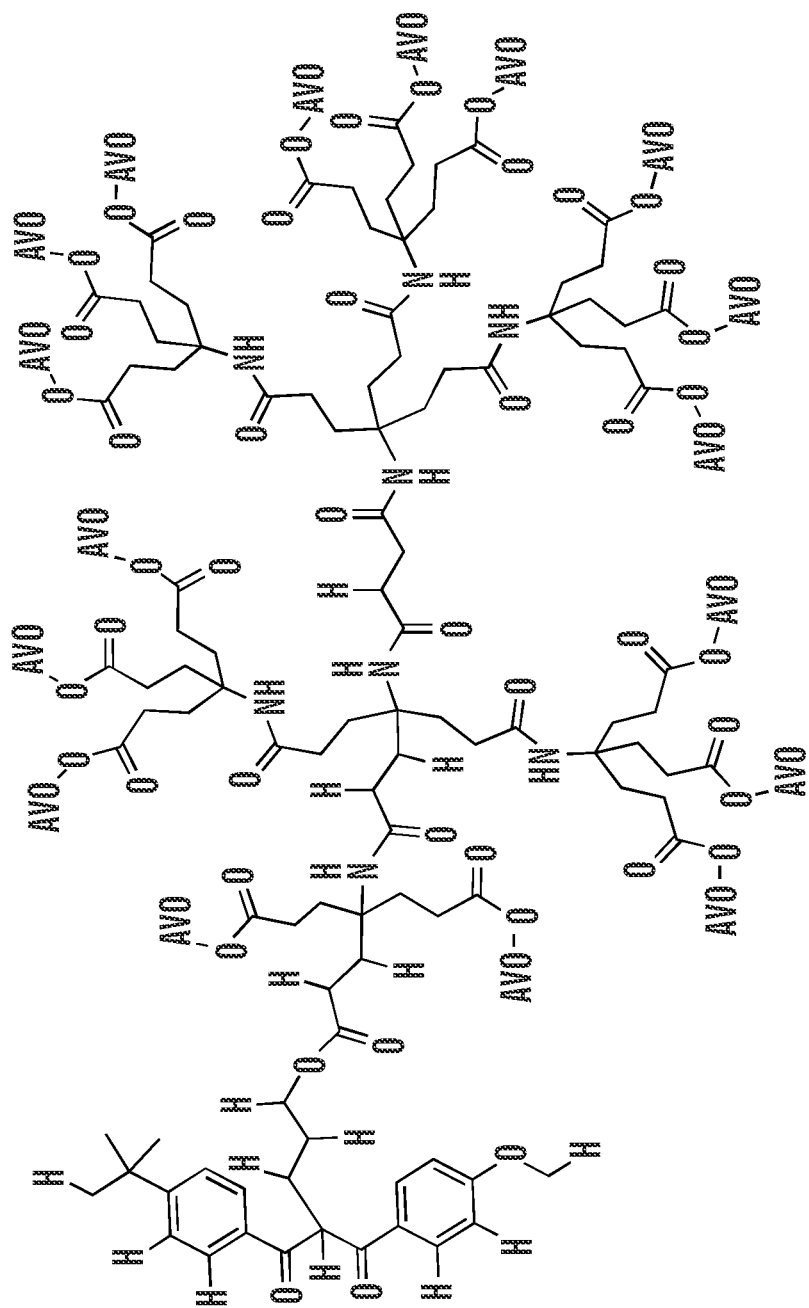
Figure 13:
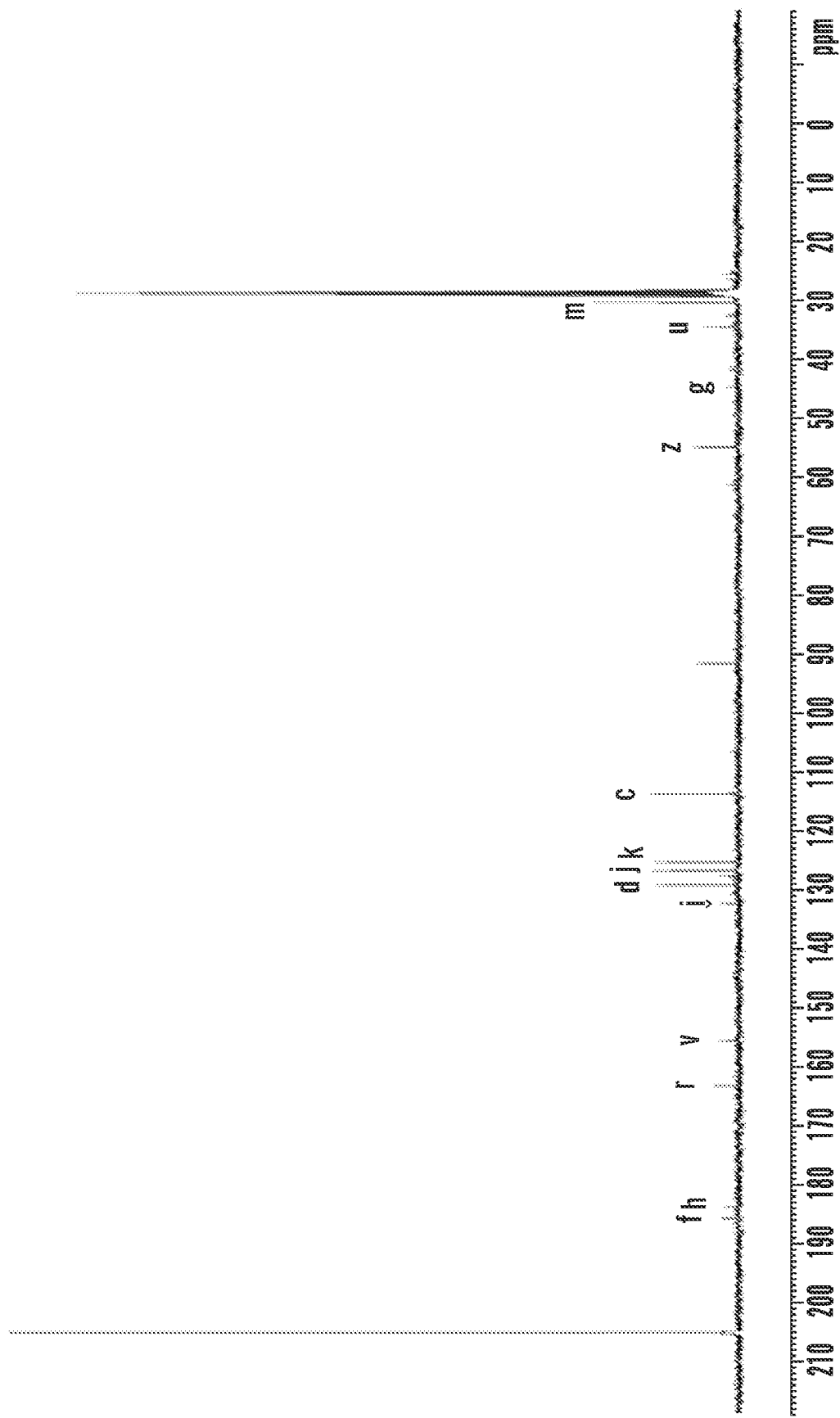
FIG. 13 is the $^{13}$C NMR spectrum of G2 Newkome-type avobenzone conjugate.
Figure 13:
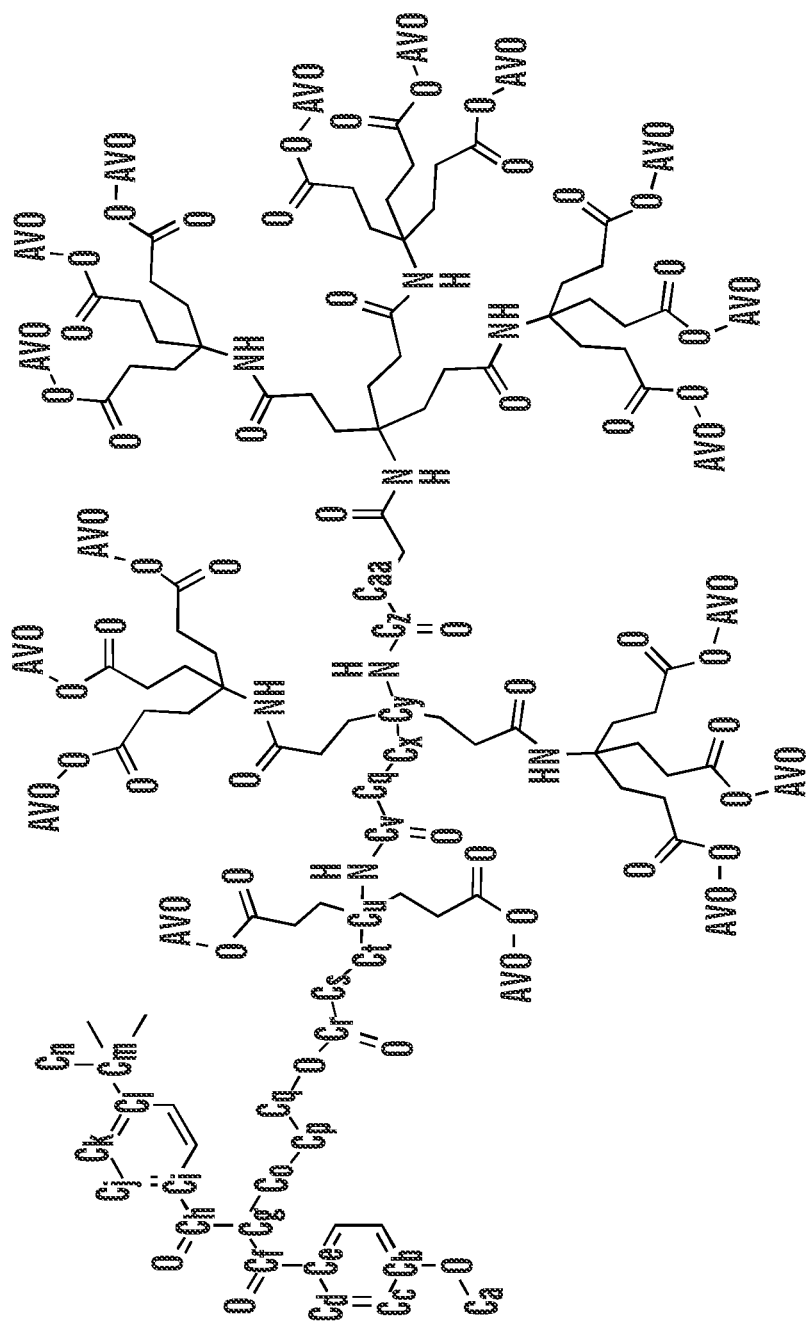

Example 5—Synthesis of Second Generation Newkome-Type Dendrimer Avobenzone Conjugate Avobenzone with linker (0.400 g 0.833 mmol) was added to a flask containing second generation Newkome-type acid dendrimer (see FIG. 2) (0.055 g 0.028 mmol) and EDC (0.600 g, 3.84 mmol). The mixture was dissolved in DMF (15 mL) and DIPEA (2 mL). Condensation of the reaction mixture yielded a yellow oil that was taken up in ethyl acetate and rinsed three times with water and dried. The compound was purified with silica gel preparation thin chromatography 1:1 hexanes:ethyl acetate. The final compound was obtained as a yellow oil (0.040 g, 13.5%). $^1$H-NMR (FIG. 12) (400 MHz, Acetone, $\delta_{ppm}$): 8.05 (app d, J=8.8 Hz, 12H, C$_q$C$_q$CHArH, diketo); 7.97 (app d, J=8.8 Hz, 12H, OC$_q$ArH, diketo); 7.49 (app d, J=6.8 Hz, 12H, C$_q$C$_q$HArH, diketo); 6.97 (app d, J=7.2 Hz, 12H, OC$_q$ArH, diketo); 3.80 (s, 18H, OCH$_3$); 3.22 (m, 1H, OC$_q$CHC$_q$O, diketo); 2.06 (br, 6H, OC$_q$OCH$_2$CH$_2$); 1.92 (s, 4H, OC$_q$OCH$_2$); 1.74 (br, 6H, OC$_q$OCH$_2$CH$_2$); 1.41 (m, 2H CH$_2$CH$_2$OH and (CH$_2$)$_9$); 1.25-1.17 (m, C$_q$(CH$_3$)$_3$ and (CH$_2$)$_9$). $^{13}$C-NMR (FIG. 13) (100 MHz, Acetone $\delta_{ppm}$): 186.1 (COCH); 184.1 (COCH); 163.5 (CH$_3$OC, Diketo); 155.9 (C(CH$_3$)$_3$C); 132.6 (ArC$_q$); 129.4 (ArC); 127.1 (ArC); 127.0 (ArC); 125.6 (ArC); 114.0 (ArC); 61.5 (CH$_2$OH); 55.1 (CH$_2$C$_q$); 44.9 (OC$_q$CHC$_q$O); 34.7 (C(CH$_3$)$_3$). MS-ESI (M)$^+$ m/z calcd for C$_{642}$H$_{900}$N$_8$O$_{16}$: 10596.55.

Figure 14:
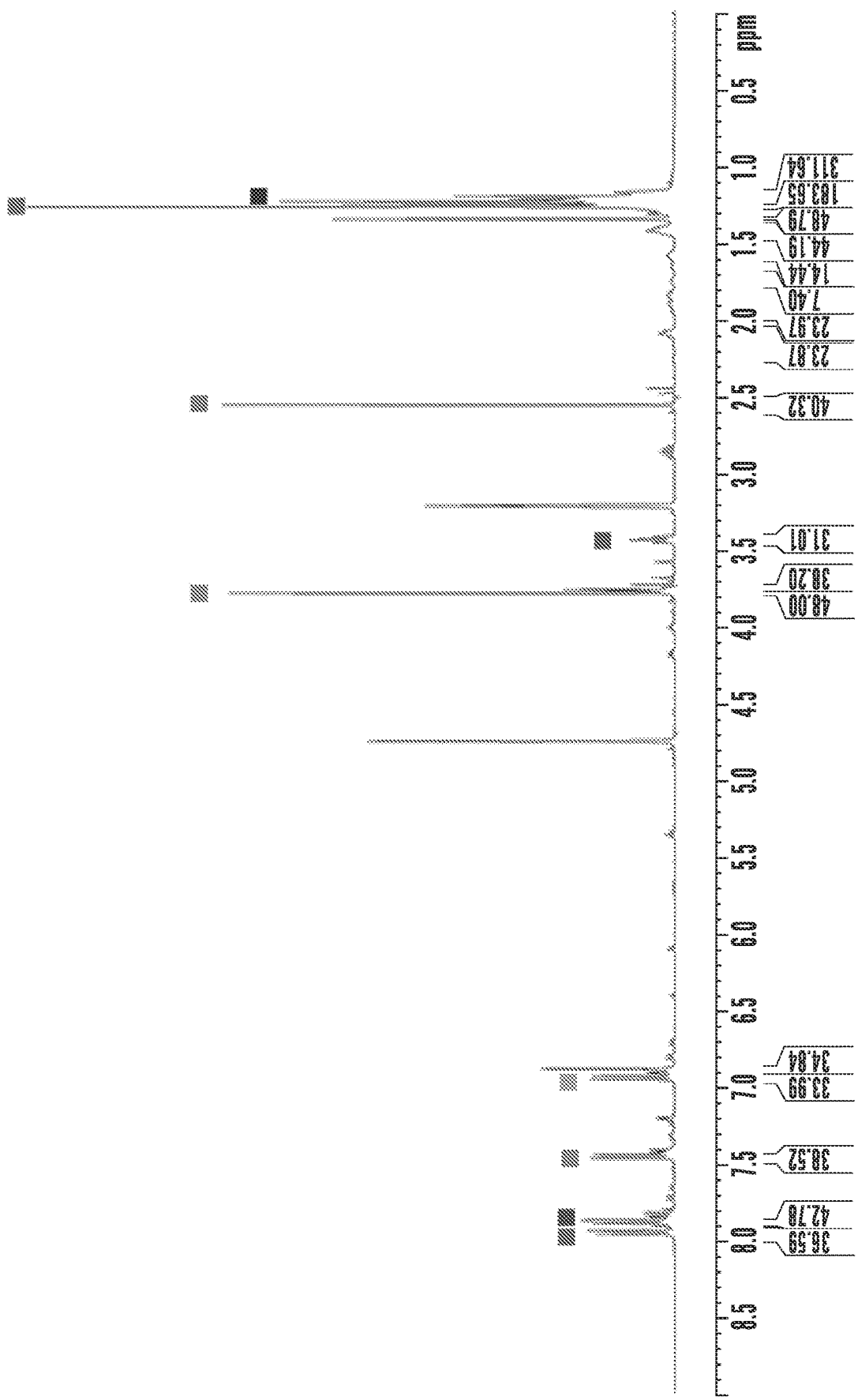
FIG. 14 is the $^1$H NMR spectrum of G2 PAMAM avobenzone conjugate.
Figure 14:
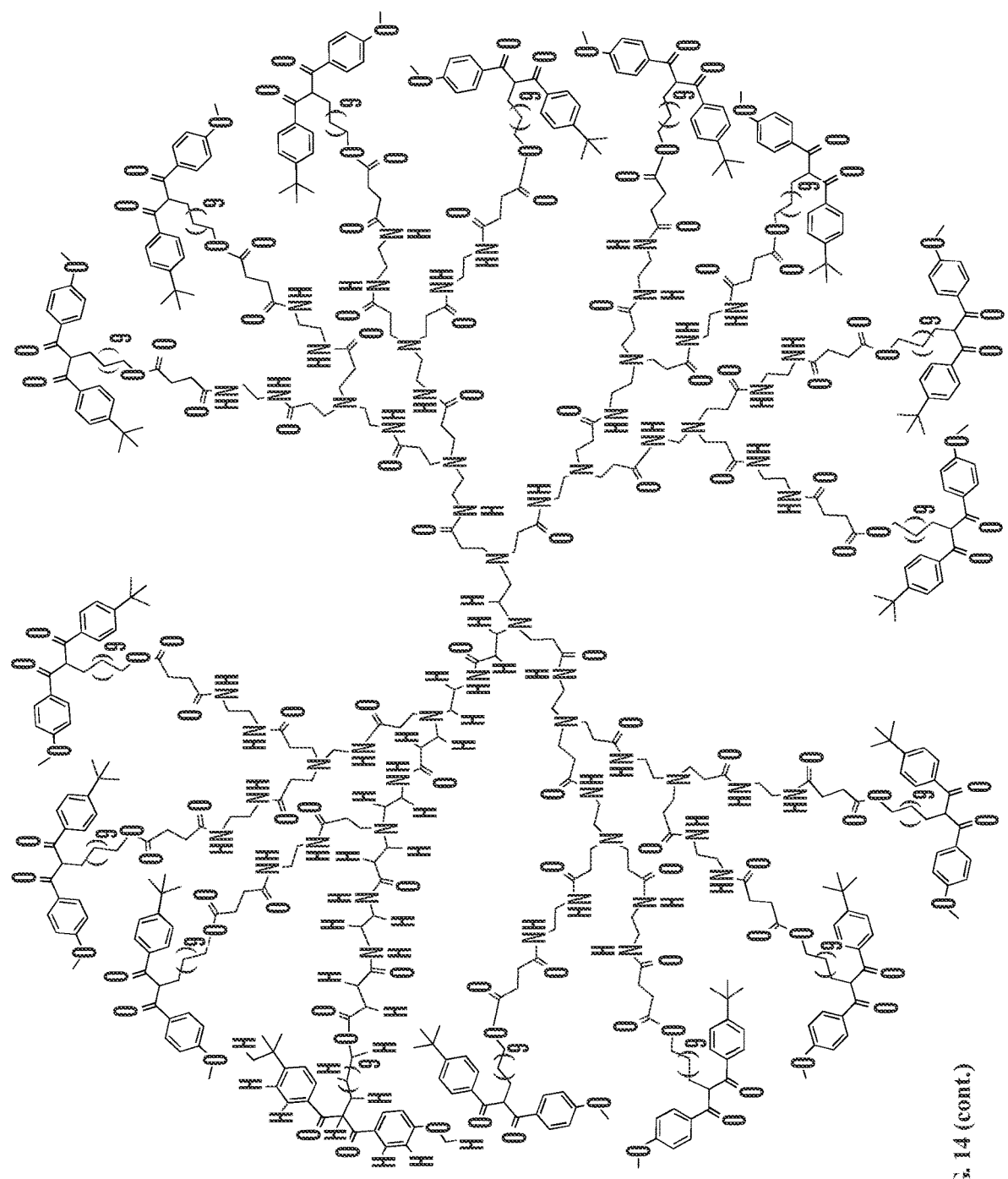
Figure 15:
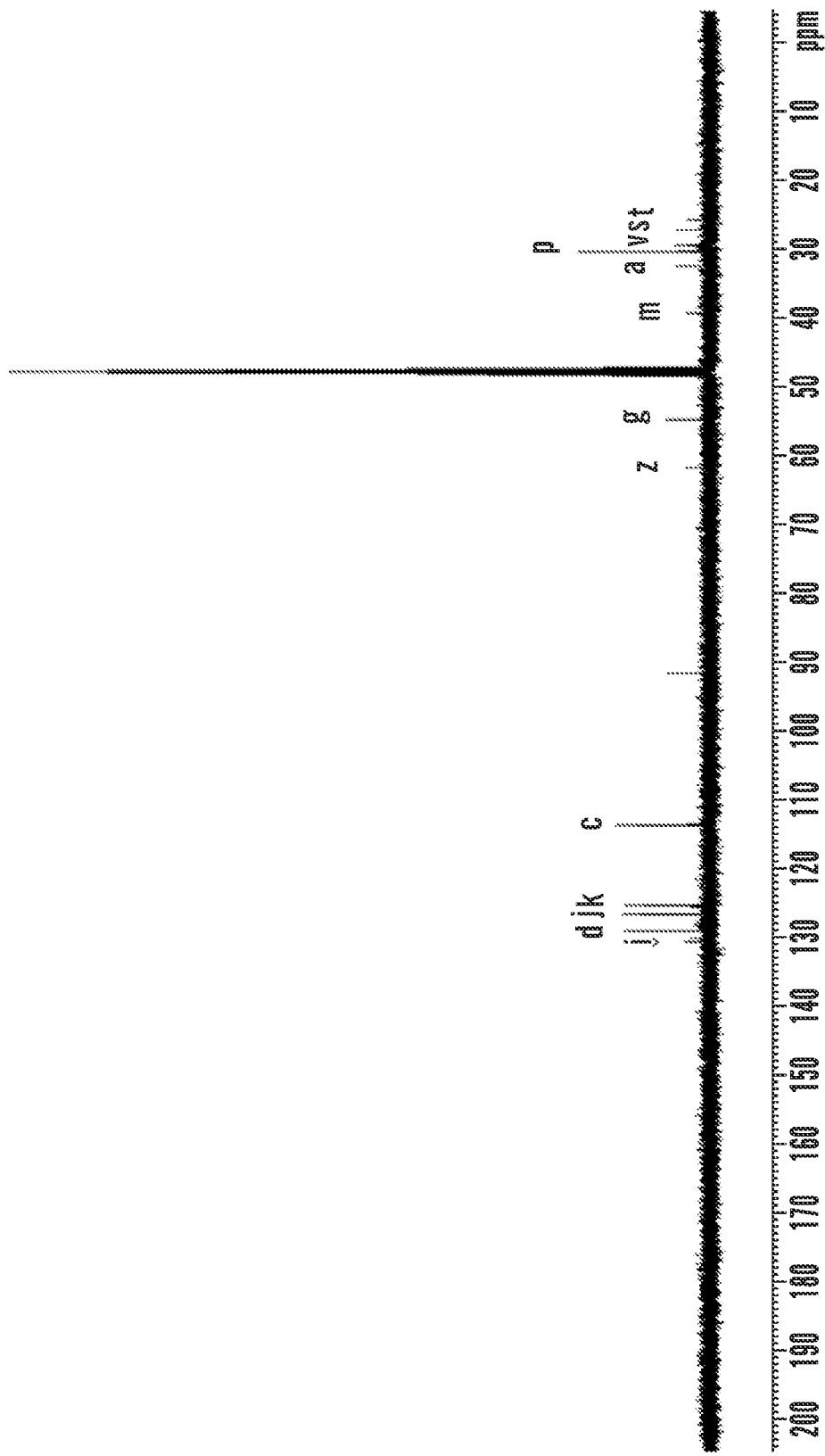
FIG. 15 is the $^{13}$C NMR spectrum of G2 PAMAM avobenzone conjugate.
Figure 15:
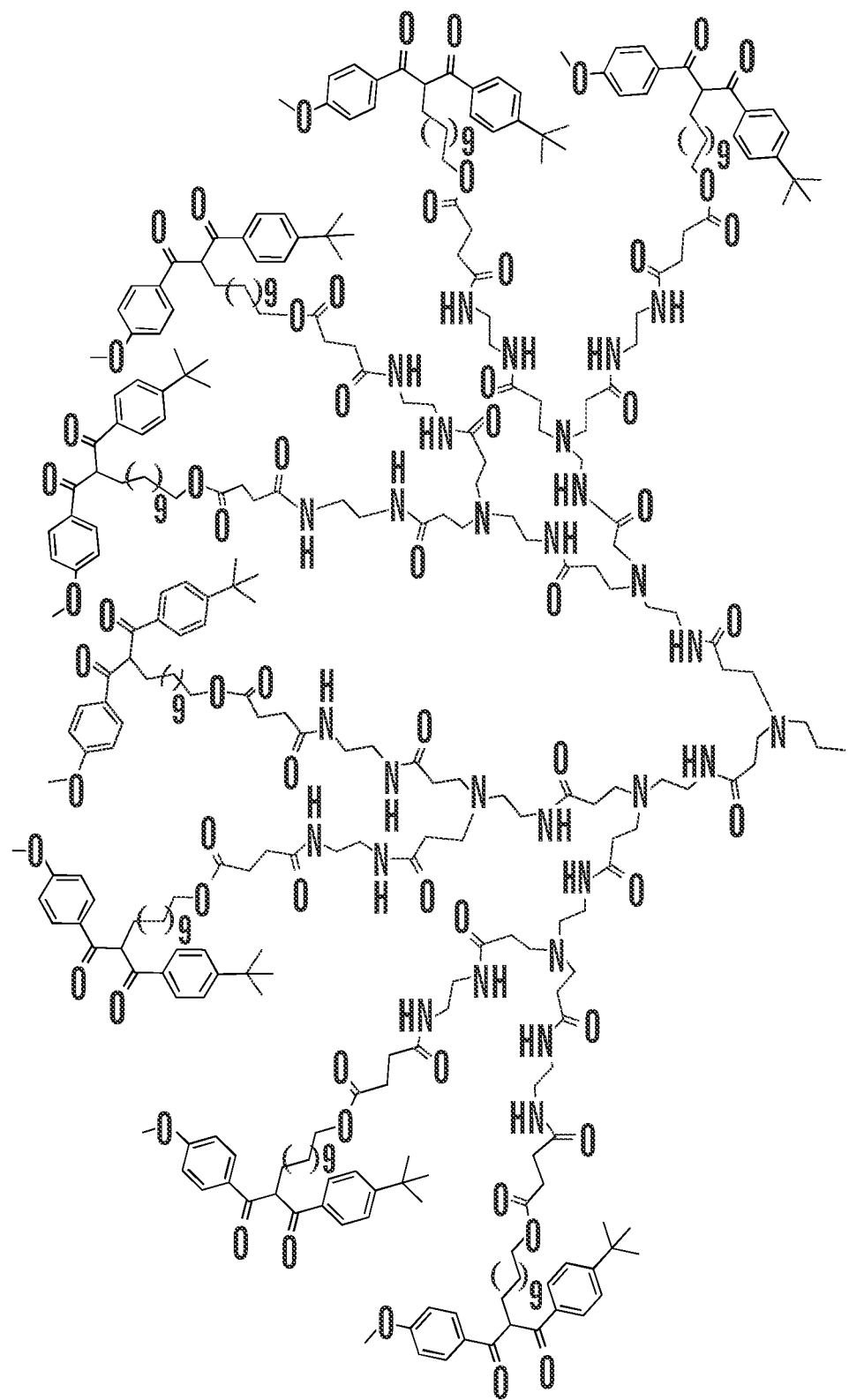
Figure 15:
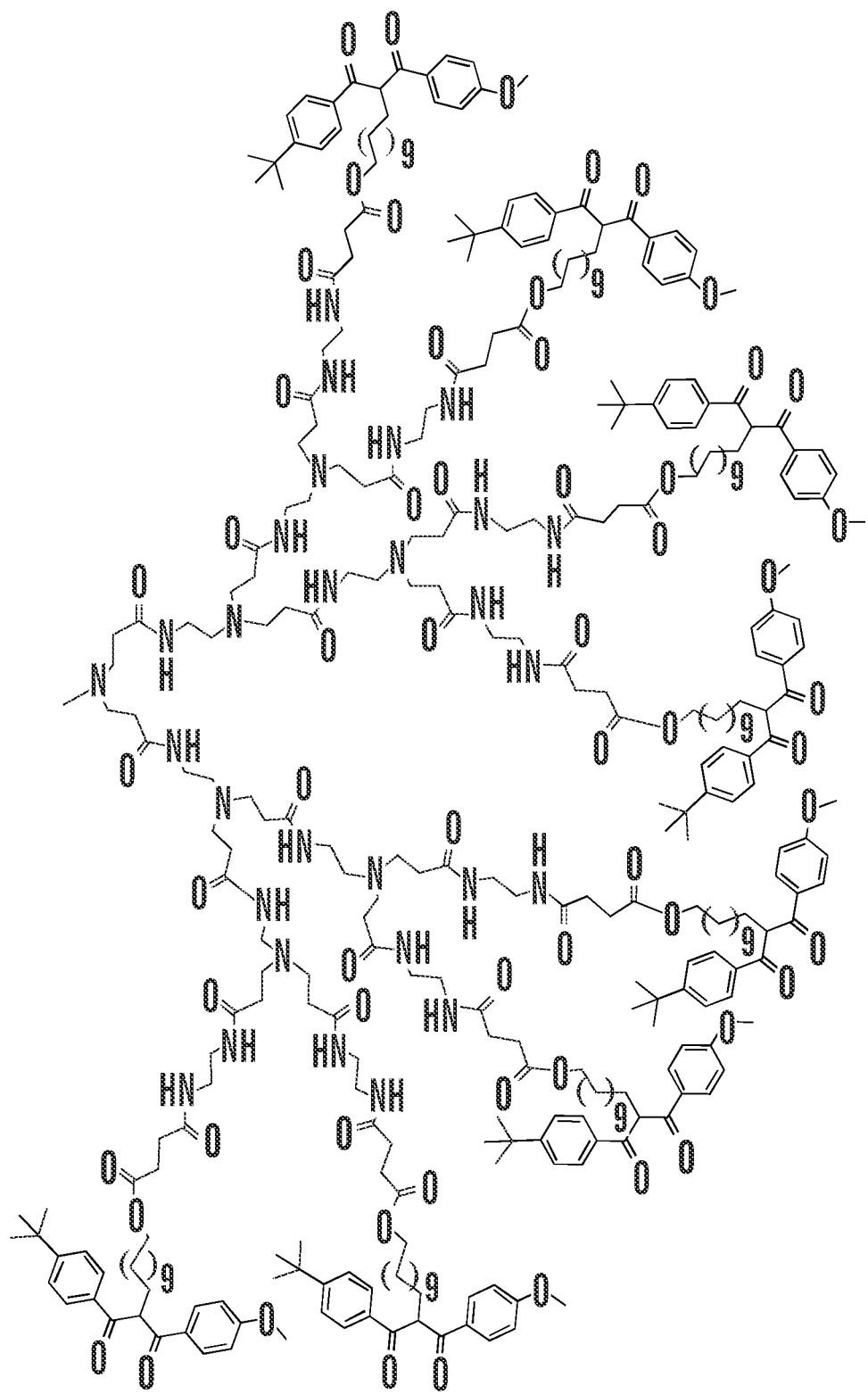

Example 6—Synthesis of Second Generation PAMAM-Type Dendrimer Avobenzone Conjugate Avobenzone with linker (0.500 g, 1.04 mmol) was added to a flask containing a second generation PAMAM succinic dendrimer (see FIG. 2) (0.28 g 0.057 mmol) and EDC (0.600 g, 3.84 mmol). The mixture was dissolved in DMF (15 mL) and DIPEA (2 mL). Condensation of the reaction mixture yielded a yellow oil that was taken up in ethyl acetate and rinsed three times with water and dried. The compound was purified with silica gel preparation thin chromatography 1:1 hexanes:ethyl acetate to a yellow oil (0.270 g, 37.8%). $^1$H-NMR (FIG. 14) (400 MHz, CDCl$_3$, $\delta_{ppm}$): 7.97 (app d, J=8.8 Hz, 32H, C$_q$C$_q$CHArH, diketo); 7.90 (app d, J=8.8 Hz, 32H, OC$_q$ArH, diketo); 7.47 (app d, J=6.8 Hz, 36H, C$_q$C$_q$HArH, diketo); 6.96 (app d, J=7.2 Hz, 32H, OC$_q$ArH, diketo); 3.79 (s, 48H, OCH$_3$); 2.09 (t, J=3.64, 32H, NHCOCH$_2$); 1.86 (m, 32H, CH$_2$NCH$_2$); 1.35-1.23 (m, C$_q$(CH$_3$)$_3$ and (CH$_2$)$_9$). $^{13}$C-NMR (FIG. 15) (100 MHz, MeOD, $\delta_{ppm}$): 133.6 (ArC$_q$); 130.7 (ArC); 129.0 (ArC); 126.6 (ArC); 125.5 (ArC); 113.6 (ArC); 61.6 (CH$_2$OH); 54.6 (CH$_2$C$_q$); 48.2 (OC$_q$CHC$_q$O); 39.0 (C(CH$_3$)$_3$); 32.2 (CH$_2$CH$_2$OH); 30.0 (CH$_3$O); 29.2-29.0 (CH$_2$)$_9$; 26.9

(CHCH$_2$); 25.5 (CH$_2$CH$_2$). MS-ESI (M)$^+$ m/z calcd for C$_{908}$H$_{1392}$N$_{58}$O$_{204}$: 16,384.98.

Figure 16:
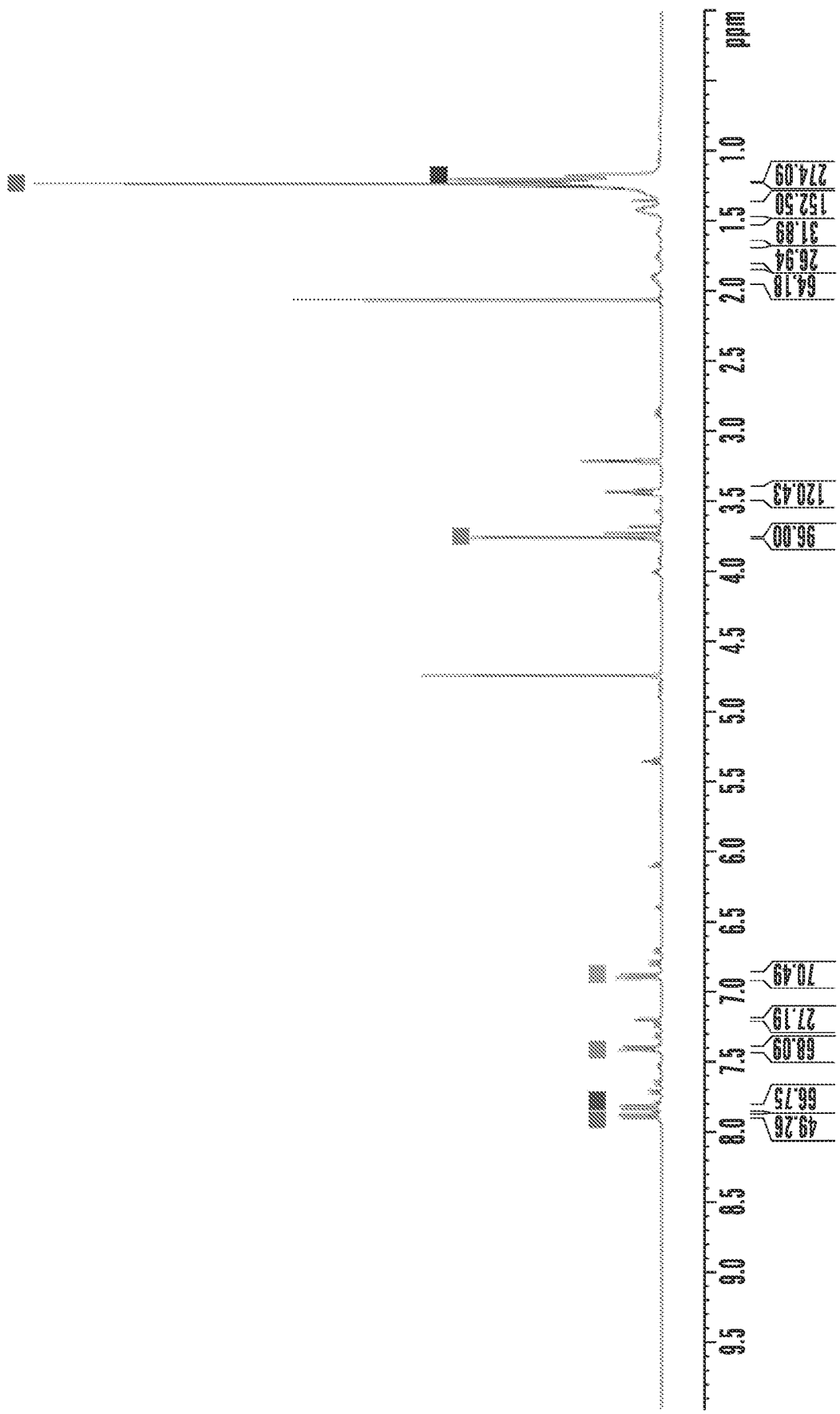
FIG. 16 is the $^1$H NMR spectrum of G3 PAMAM avobenzone conjugate.
Figure 16:
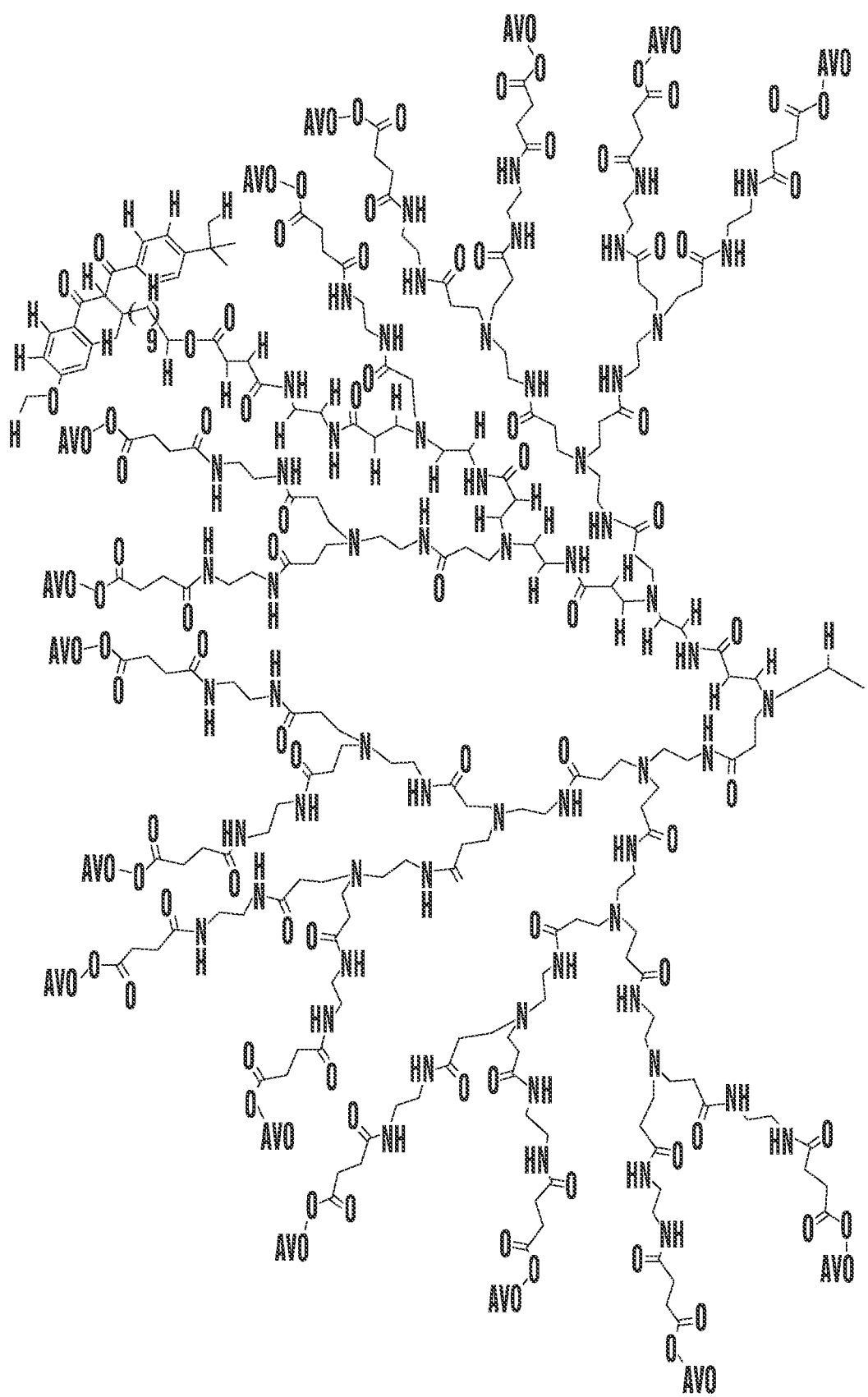
Figure 16:
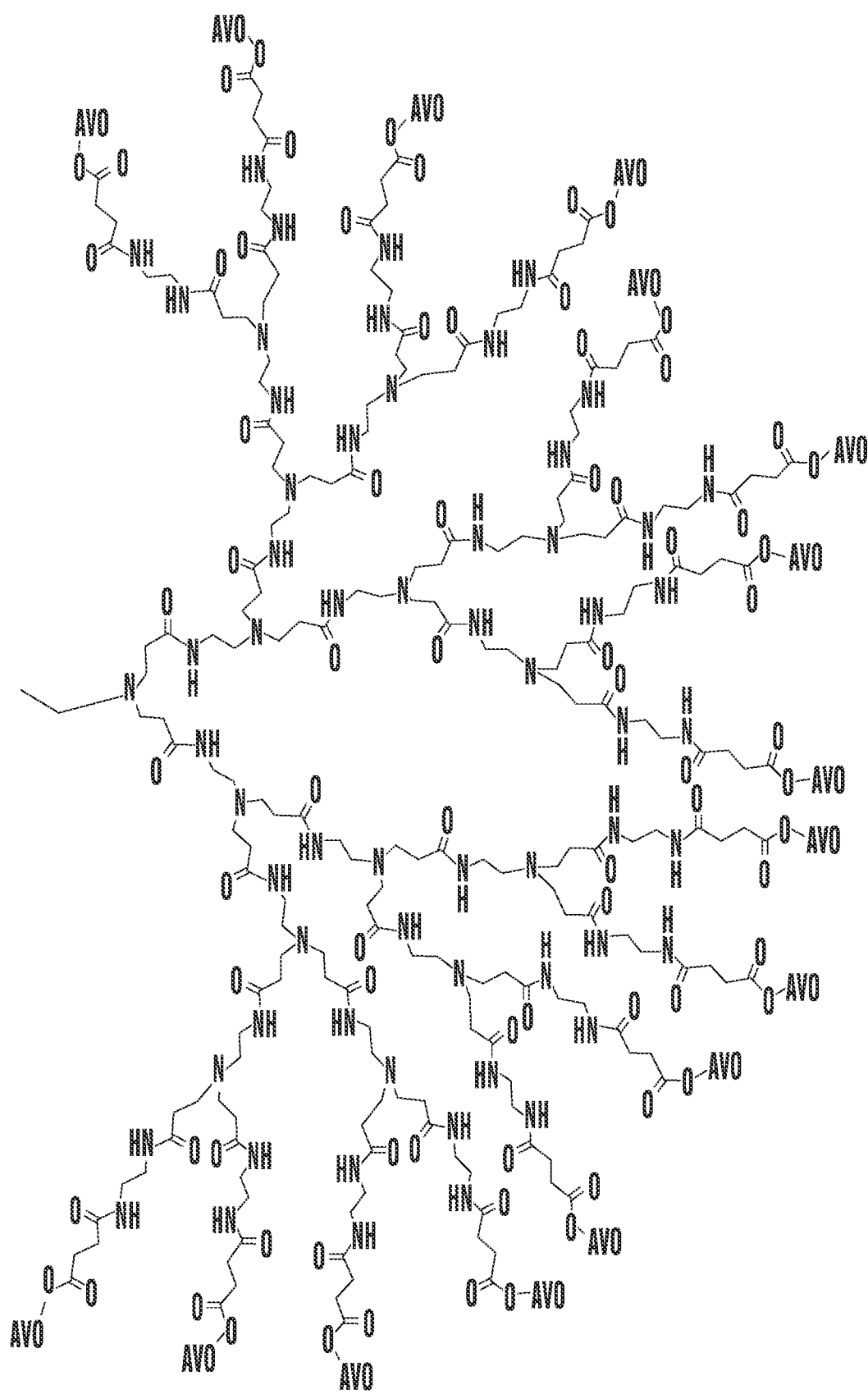
Figure 17:
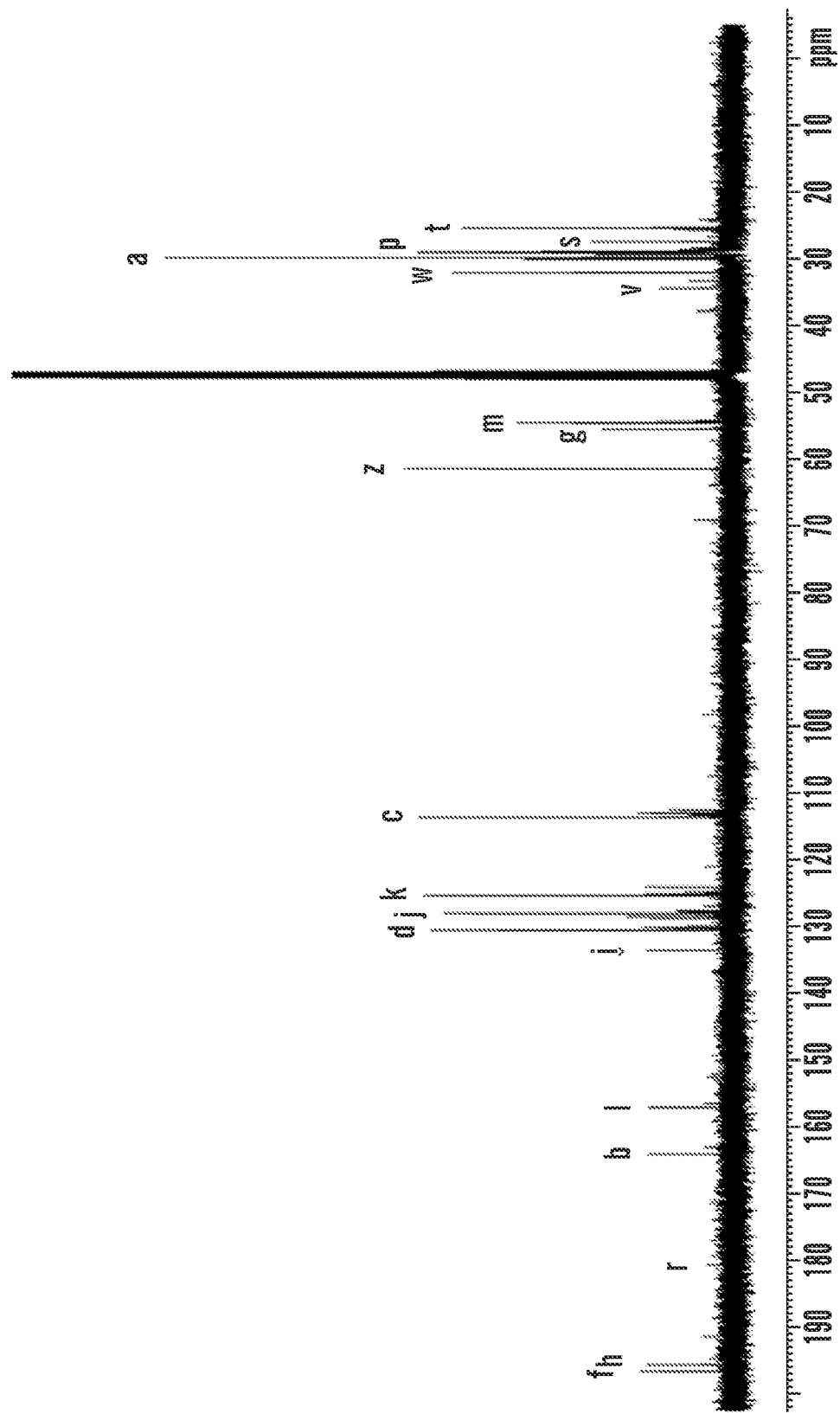
FIG. 17 is the $^{13}$C NMR spectrum of G3 PAMAM avobenzone conjugate.
Figure 17:
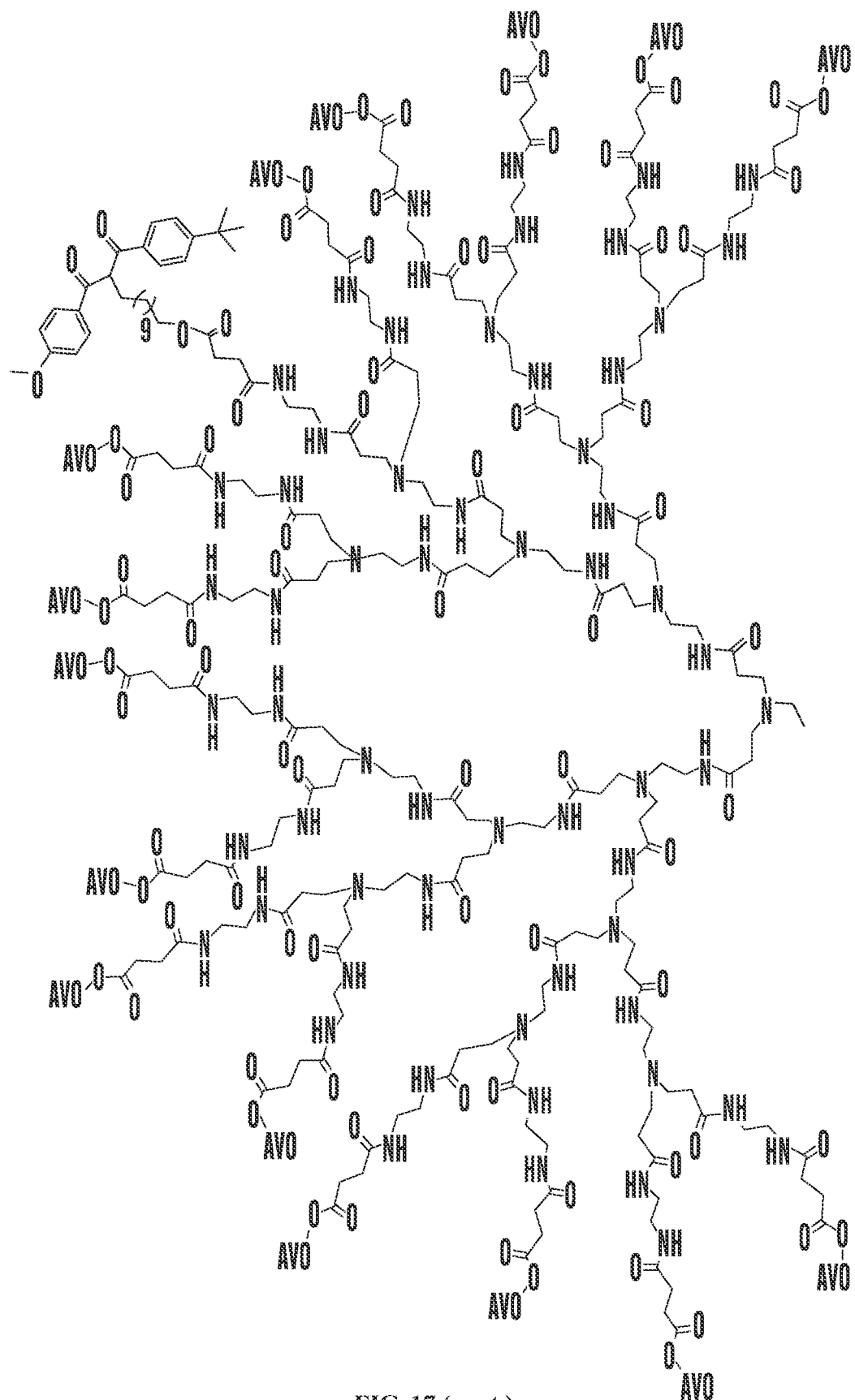
Figure 17:
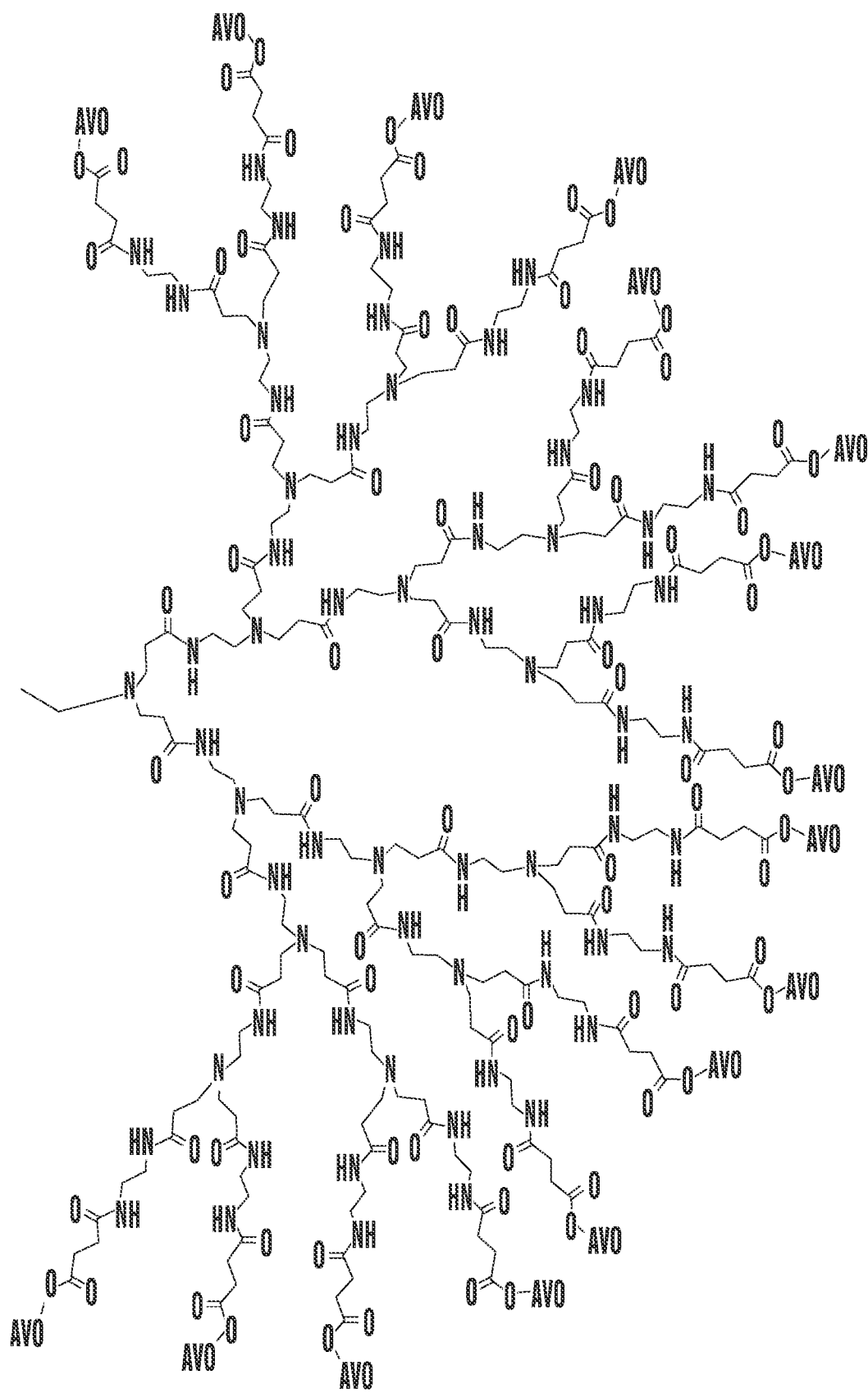
Figure 18:
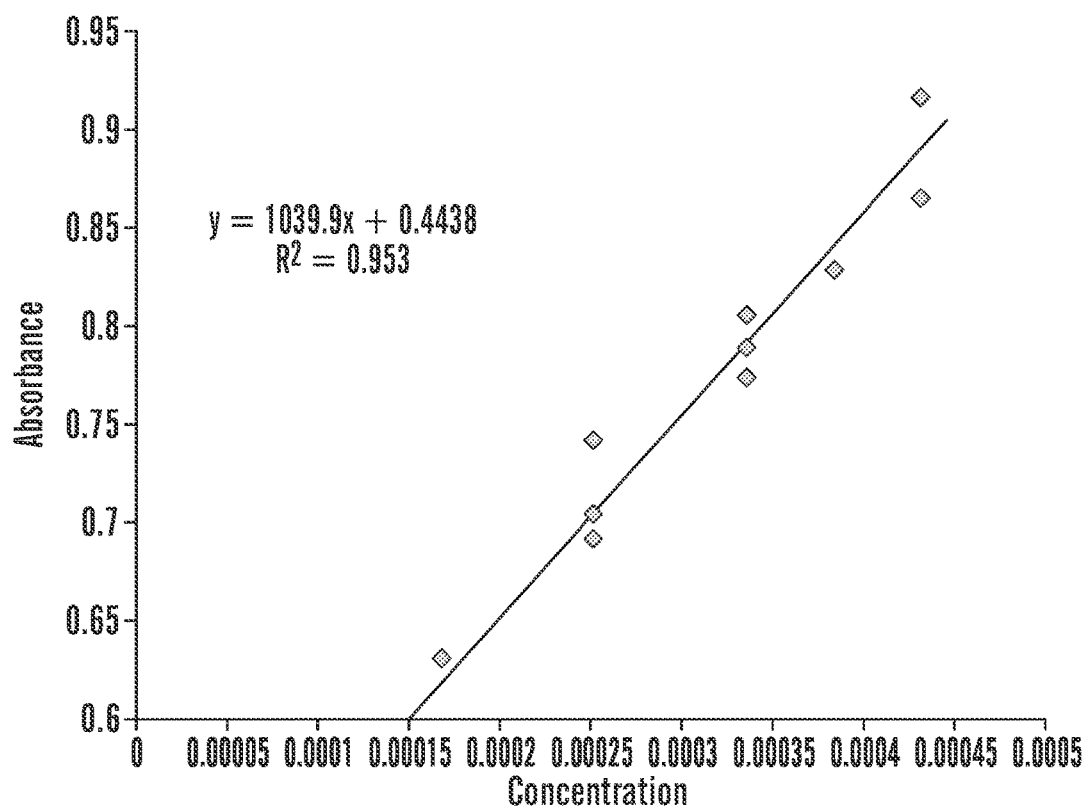
FIG. 18 is the UV calibration of avobenzone at 357 nM in isopropanol.
Figure 19:
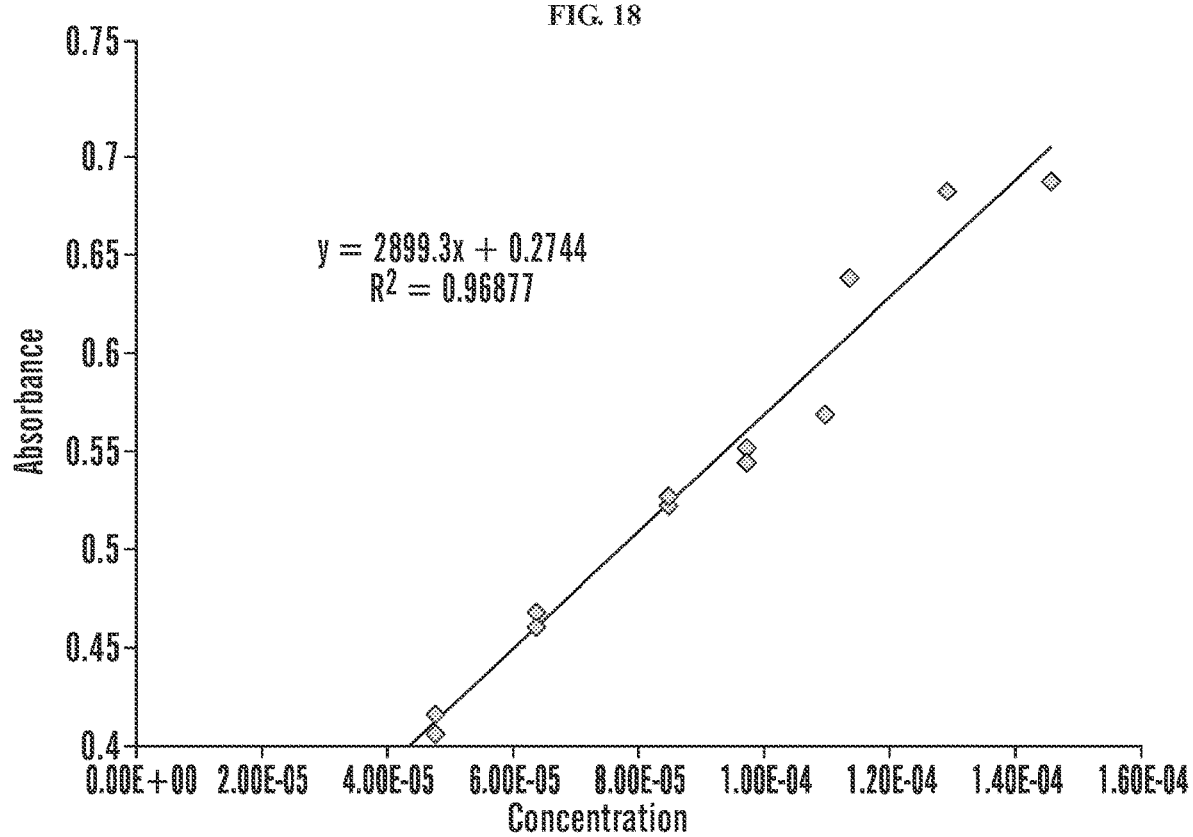
FIG. 19 is the UV calibration of avobenzone with linker at 357 nM in isopropanol.
Figure 20:
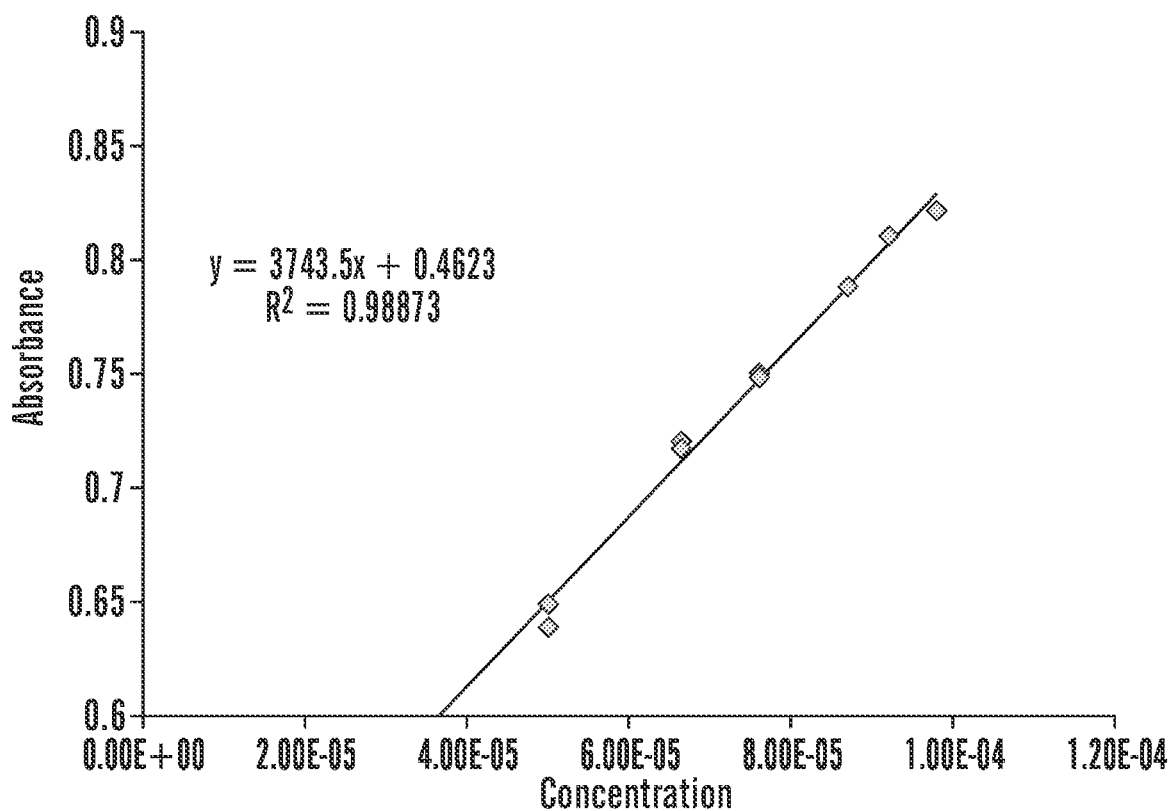
FIG. 20 is the UV calibration of G0 avobenzone conjugate at 357 nM in isopropanol.
Figure 21:
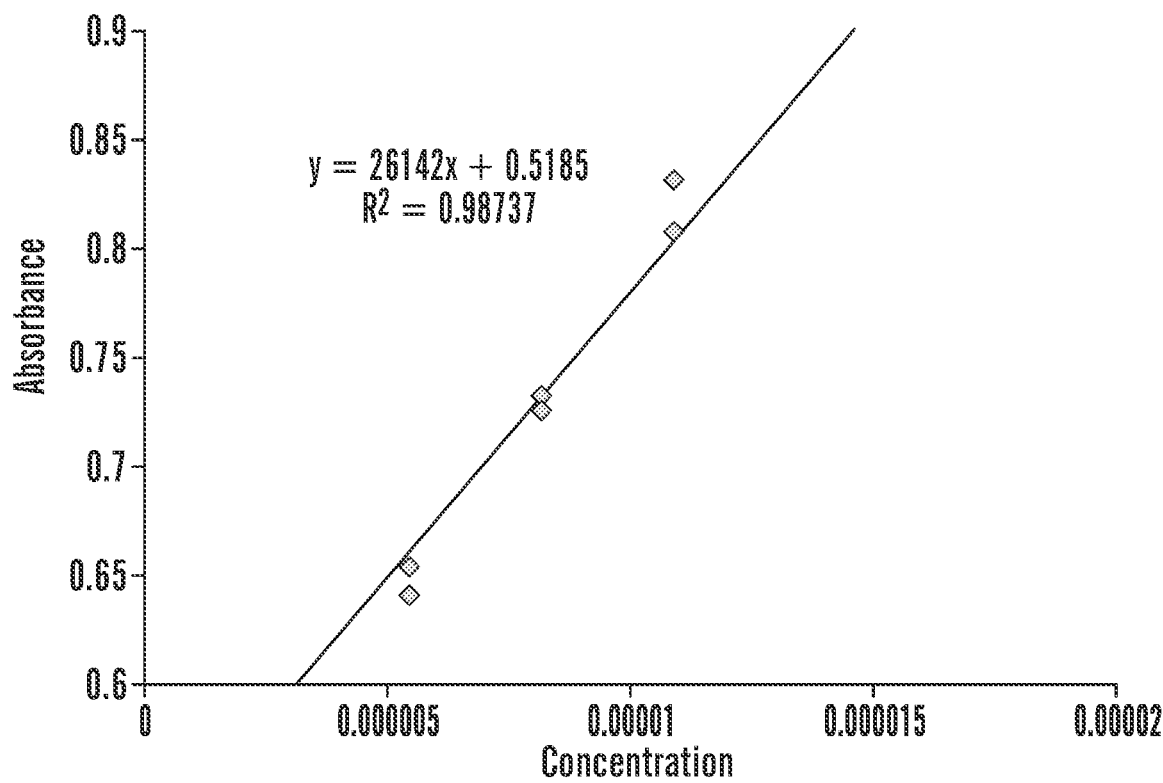
FIG. 21 is the UV calibration of G1 Newkome-type avobenzone conjugate at 357 nM in isopropanol.
Figure 22:
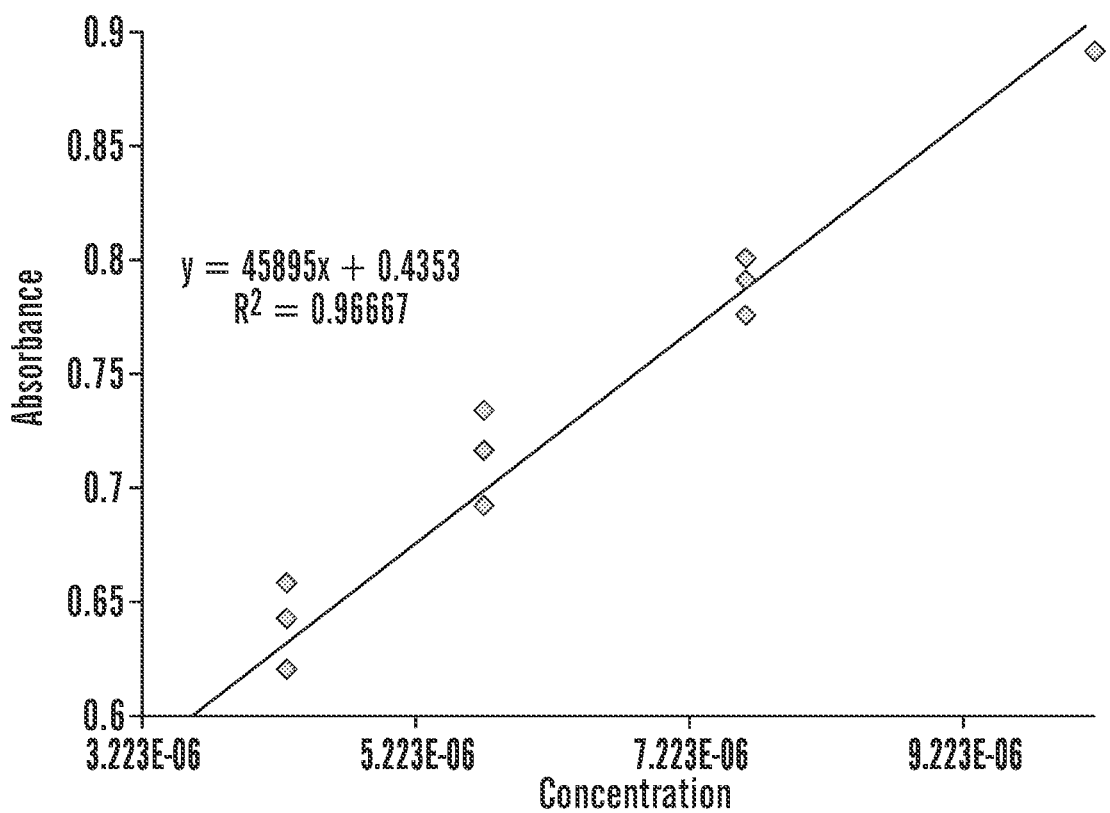
FIG. 22 is the UV calibration of G2 Newkome-type avobenzone conjugate at 357 nM in isopropanol.
Figure 23:
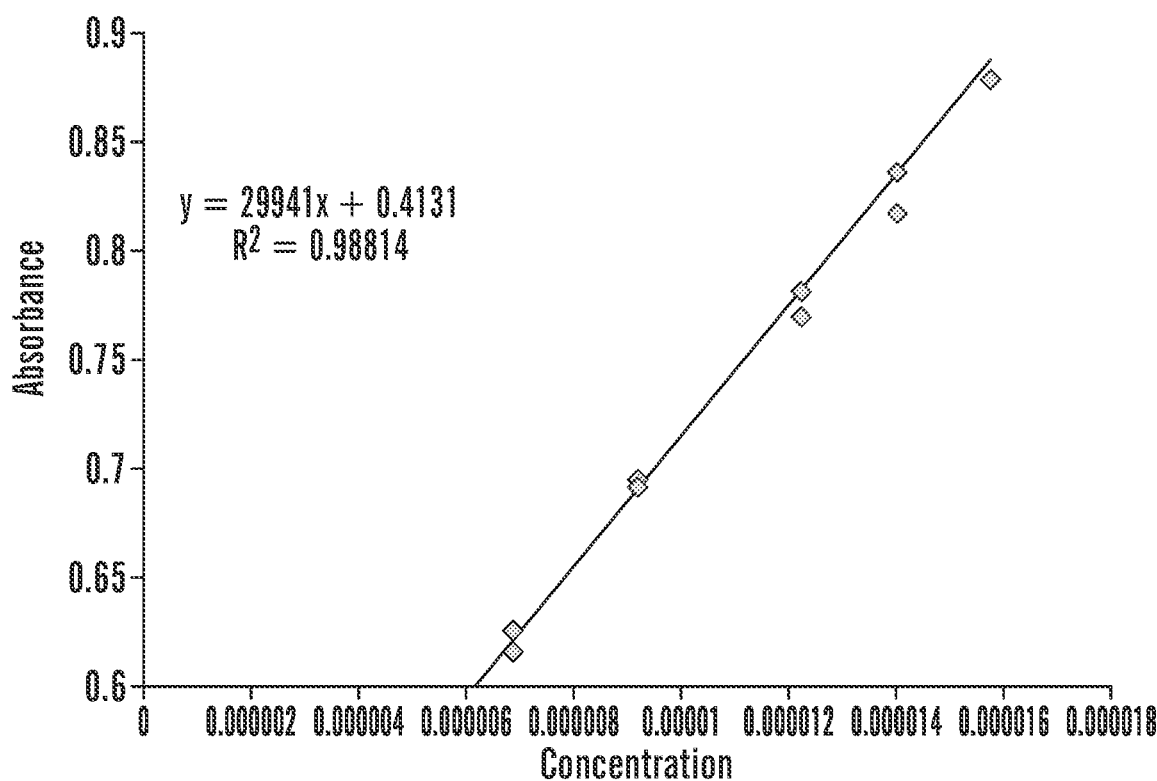
FIG. 23 is the UV calibration of G2 PAMAM avobenzone conjugate at 357 nM in isopropanol.

Example 7—Synthesis of Third Generation PAMAM-Type Dendrimer Avobenzone Conjugate Avobenzone with linker (0.400 g 0.833 mmol) was added to a flask containing a third generation PAMAM succinic dendrimer (0.100 g 0.0098 mmol) and EDC (0.600 g, 3.84 mmol). The mixture was dissolved in DMF (15 mL) and DIPEA (2 mL). Condensation of the reaction mixture yielded a yellow oil that was taken up in ethyl acetate and rinsed three times with water and dried. The compound was purified with silica gel preparation thin chromatography 1:1 hexanes:ethyl acetate to yield a yellow oil (0.080 g, 31.6%). $^1$H-NMR (FIG. 16) (400 MHz, MeOD, $\delta_{ppm}$): 7.92 (app d, J=8.8 Hz, 64H, C$_q$C$_q$CHArH, diketo); 7.85 (app d, J=8.8 Hz, 64H, OC$_q$ArH, diketo); 7.43 (app d, J=6.8 Hz, 64H, C$_q$C$_q$HArH, diketo); 6.91 (app d, J=7.2 Hz, 64H, OC$_q$ArH, diketo); 3.75 (s, 96H, OCH$_3$), 3.45 (m, 1H, OC$_q$CHC$_q$O, diketo); 1.91 (t, J=3.64, 32H, NHCOCH$_2$); 1.75 (m, 32H, CH$_2$NCH$_2$); 1.42-1.23 (m, C$_q$(CH$_3$)$_3$ and (CH$_2$)$_9$). $^{13}$C-NMR (FIG. 17) (100 MHz, MeOD, $\delta_{ppm}$): 196.7 (COCH); 195.7 (COCH); 164.2 (CH$_3$OC, Diketo); 157.2 (C(CH$_3$)$_3$C); 133.6 (ArC$_q$); 130.7 (ArC$_q$); 130.3 (ArC); 128.9 (ArC); 128.2 (ArC); 113.2 (ArC); 61.6 (CH$_2$OH); 55.6 (CH$_2$C$_q$); 54.5 (OC$_q$CHC$_q$O); 34.6 (C(CH$_3$)$_3$); 30.2 (CH$_2$CH$_2$OH); 29.5 (CH$_3$O); 29.3-29.1 (CH$_2$)$_9$; 29.0 (CHCH$_2$); 27.6 (CH$_2$CH$_2$) MALDI (M-1 avolinker+TFA+isopropanol)$^+$ m/z calcd for C$_{1396}$H$_{2079}$N$_{122}$O$_{283}$F$_3$: 25156.00 found 25156.32. MALDI (M-3 avolinker+2 TFA)$^+$ m/z calcd for C$_{1396}$H$_{2079}$N$_{122}$O$_{283}$F$_3$: 24242.58 found 24239.46.

Example 8—UV-Vis Calibration of Avobenzone and Avobenzone Conjugates

Avobenzone and the avobenzone conjugates were each dissolved in isopropanol and the titrations were run in triplicate to calculate extinction coefficients for each conjugate. The results are shown in FIG. 18 through FIG. 24.

Example 9—UV Decay of Avobenzone and Avobenzone Conjugates

Figure 24:
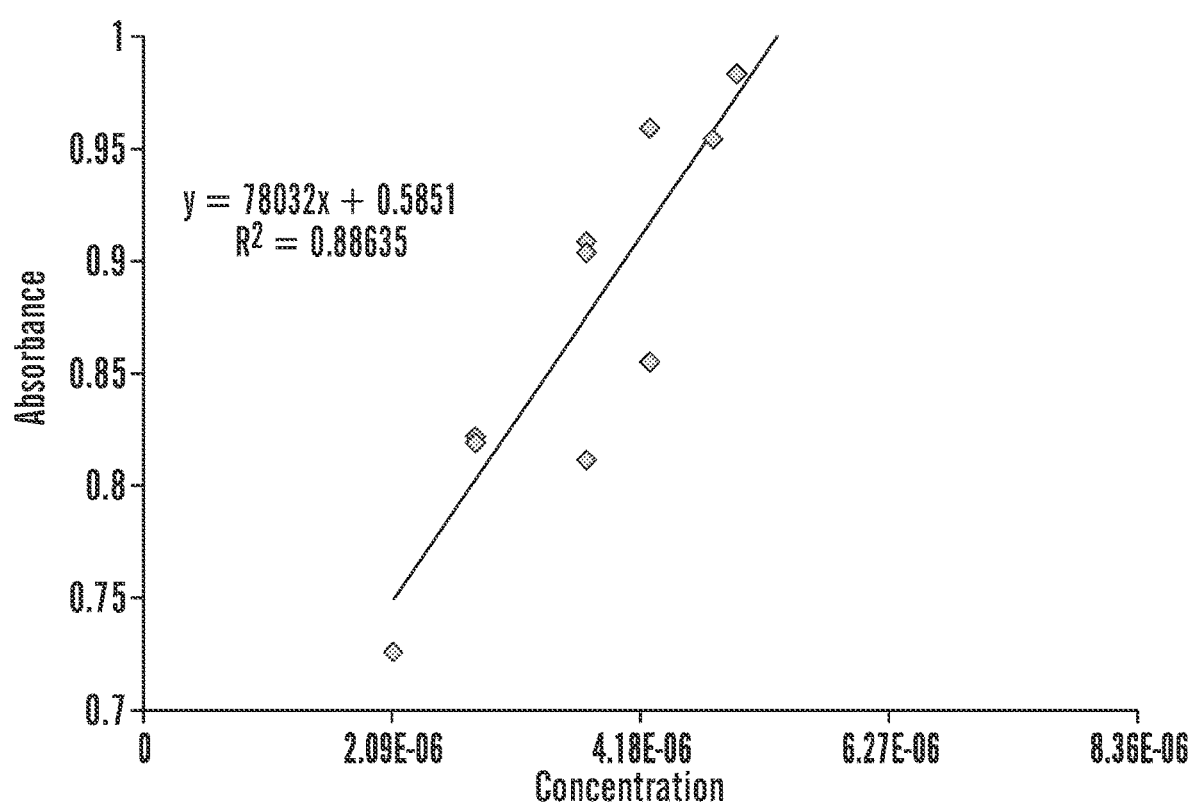
FIG. 24 is the UV calibration of G3 PAMAM avobenzone conjugate at 357 nM in isopropanol.
Figure 25:
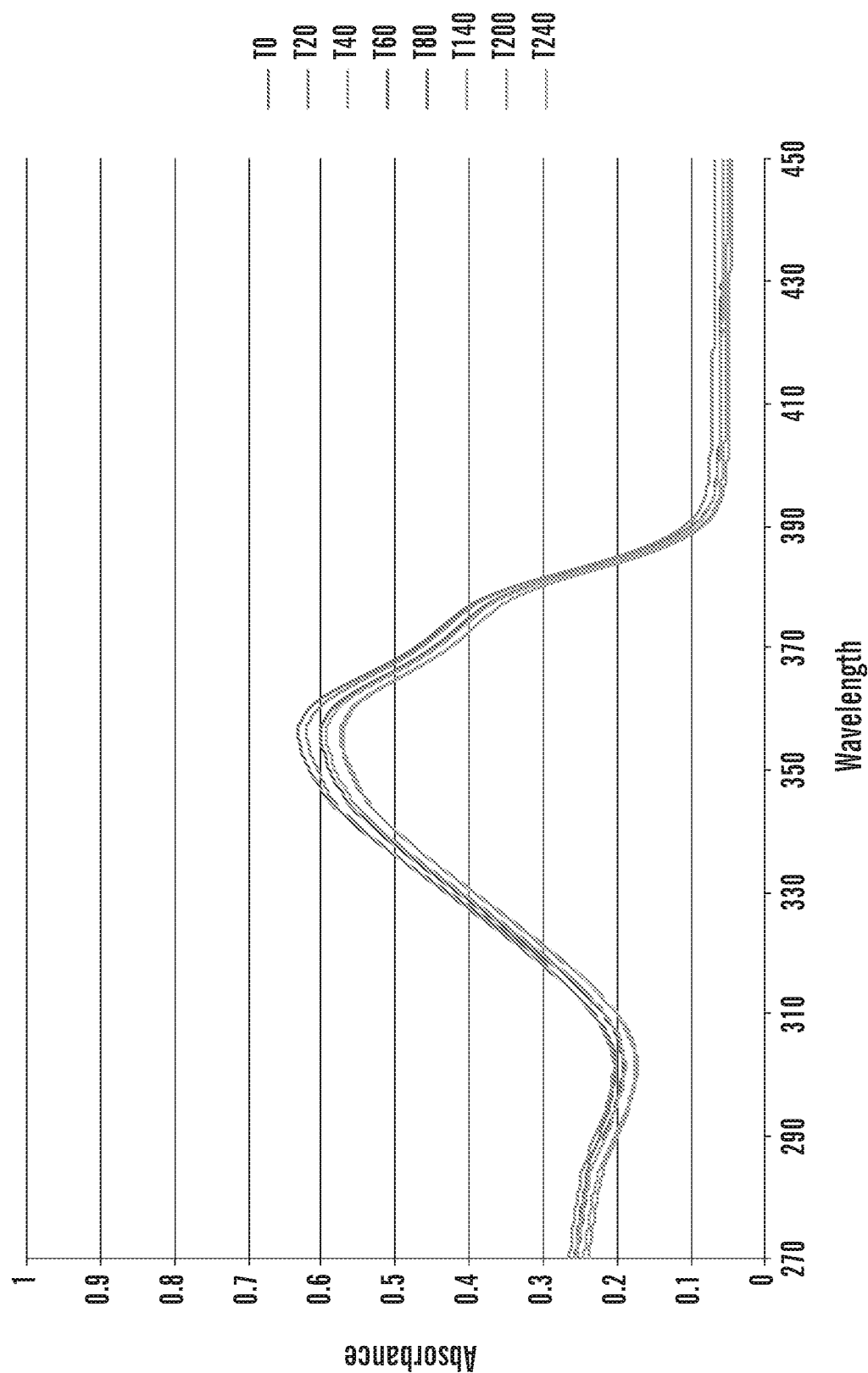
FIG. 25 is the UV degradation (run in triplicate) of avobenzone at 357 nM in ethyl acetate. (Top graph: visible lines at ~357 nm are, from top to bottom: T20, T40, T60, T140, T200, T240. Center graph: visible lines at ~357 nm are, from top to bottom: T0, T20, T80, T140, T240. Bottom graph: visible lines at ~357 nm are, from top to bottom: T0, T80, T40, T60, T200, T240.)
Figure 25:
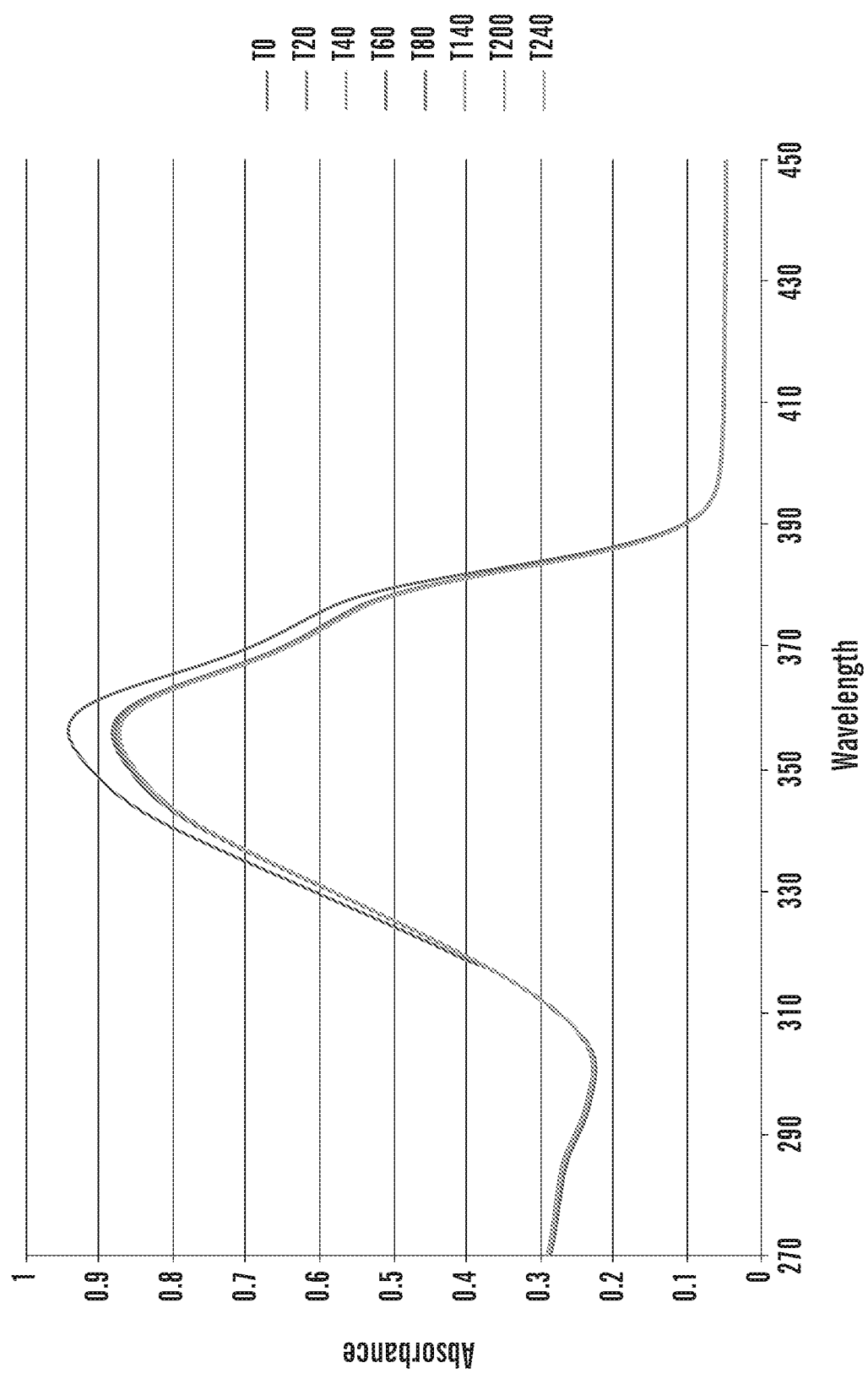
Figure 25:
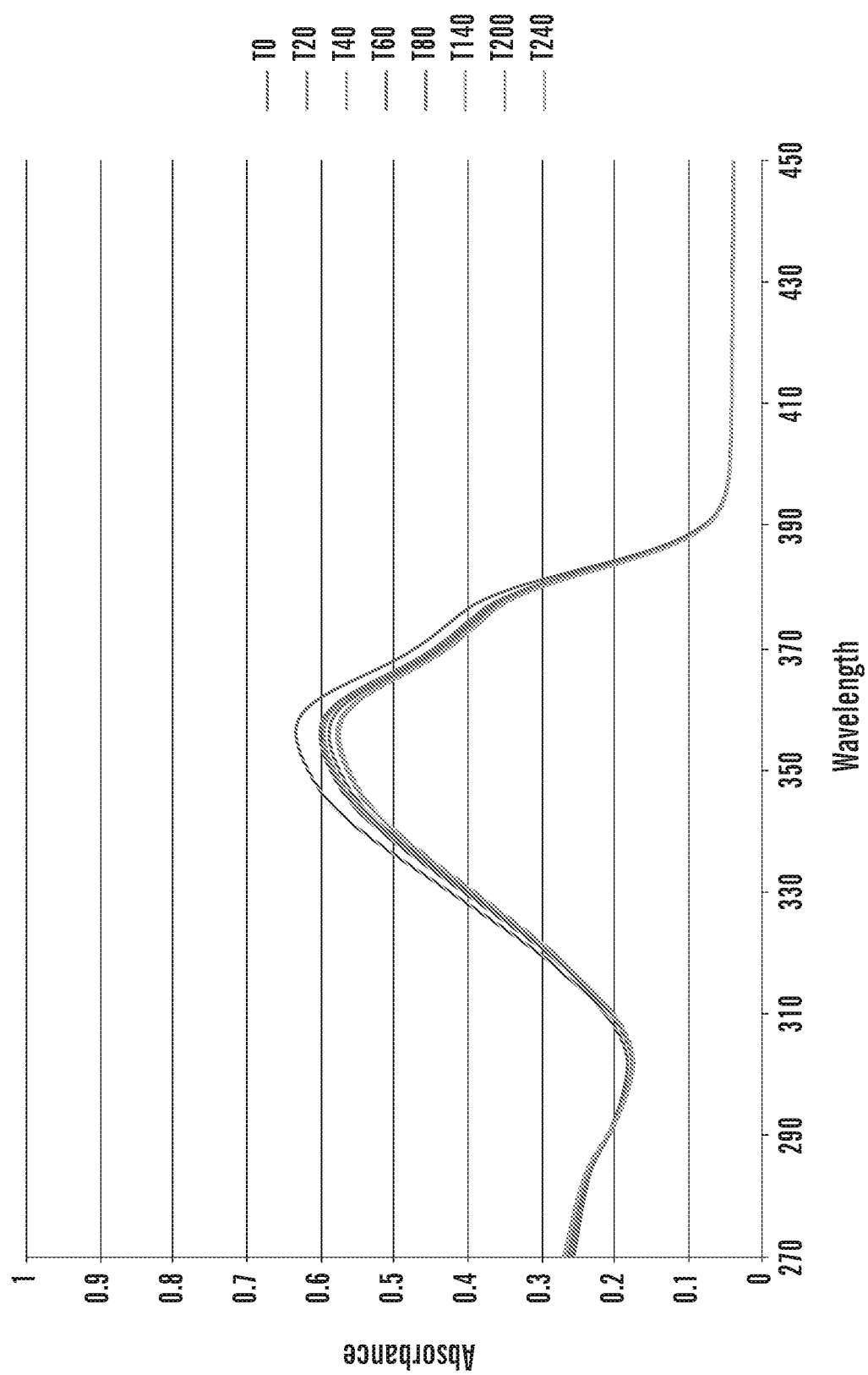
Figure 26:
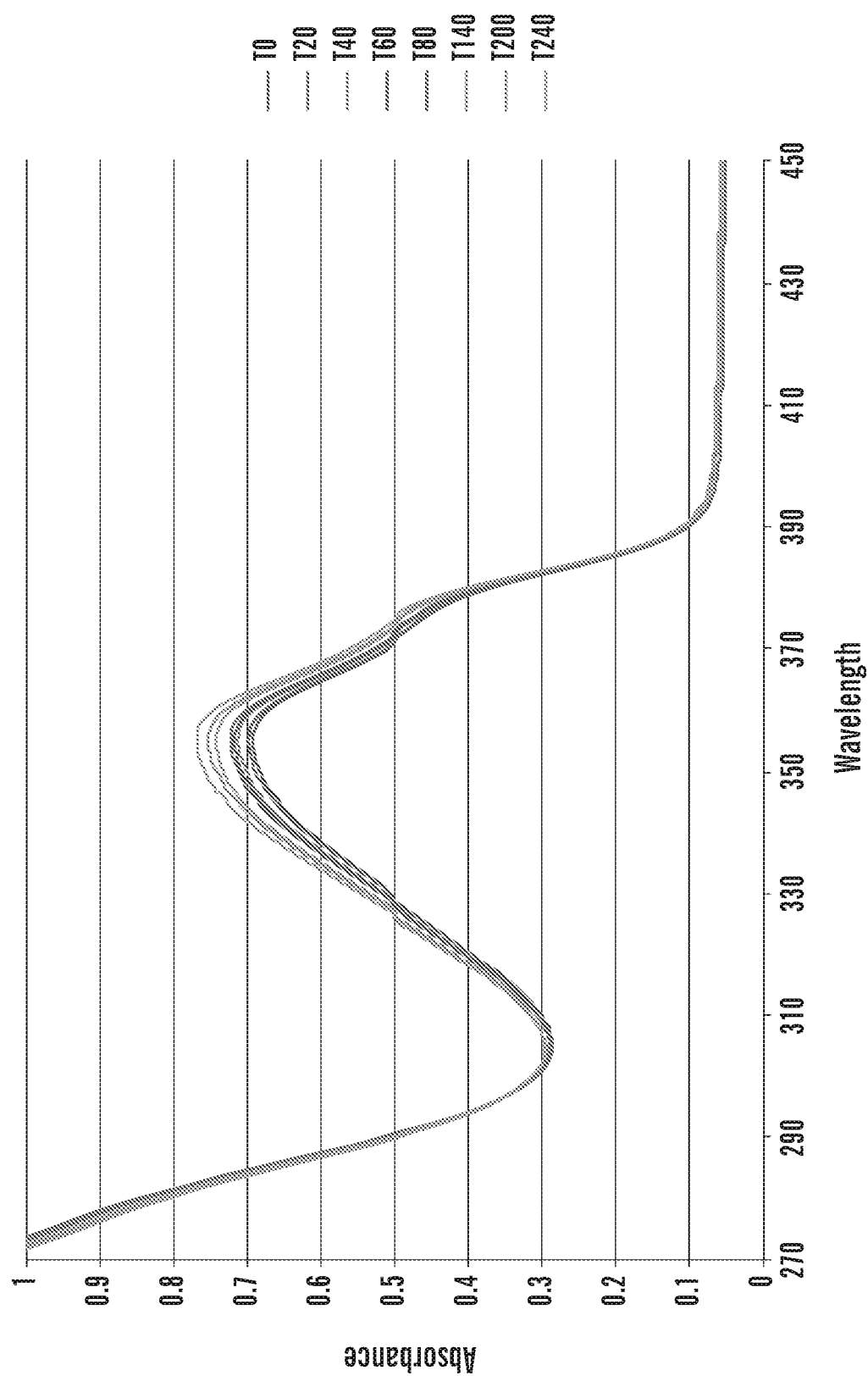
FIG. 26 is the UV degradation (run in triplicate) of avobenzone with linker at 357 nM in ethyl acetate. (op and bottom graphs: visible lines at ~357 nm are, from top to bottom: T240, T200, T140, T80, T60, T40, T20, T0. Center graph: visible lines at ~357 nm are, from top to bottom: T240, T200, T140, T60, T20, T80.)
Figure 26:
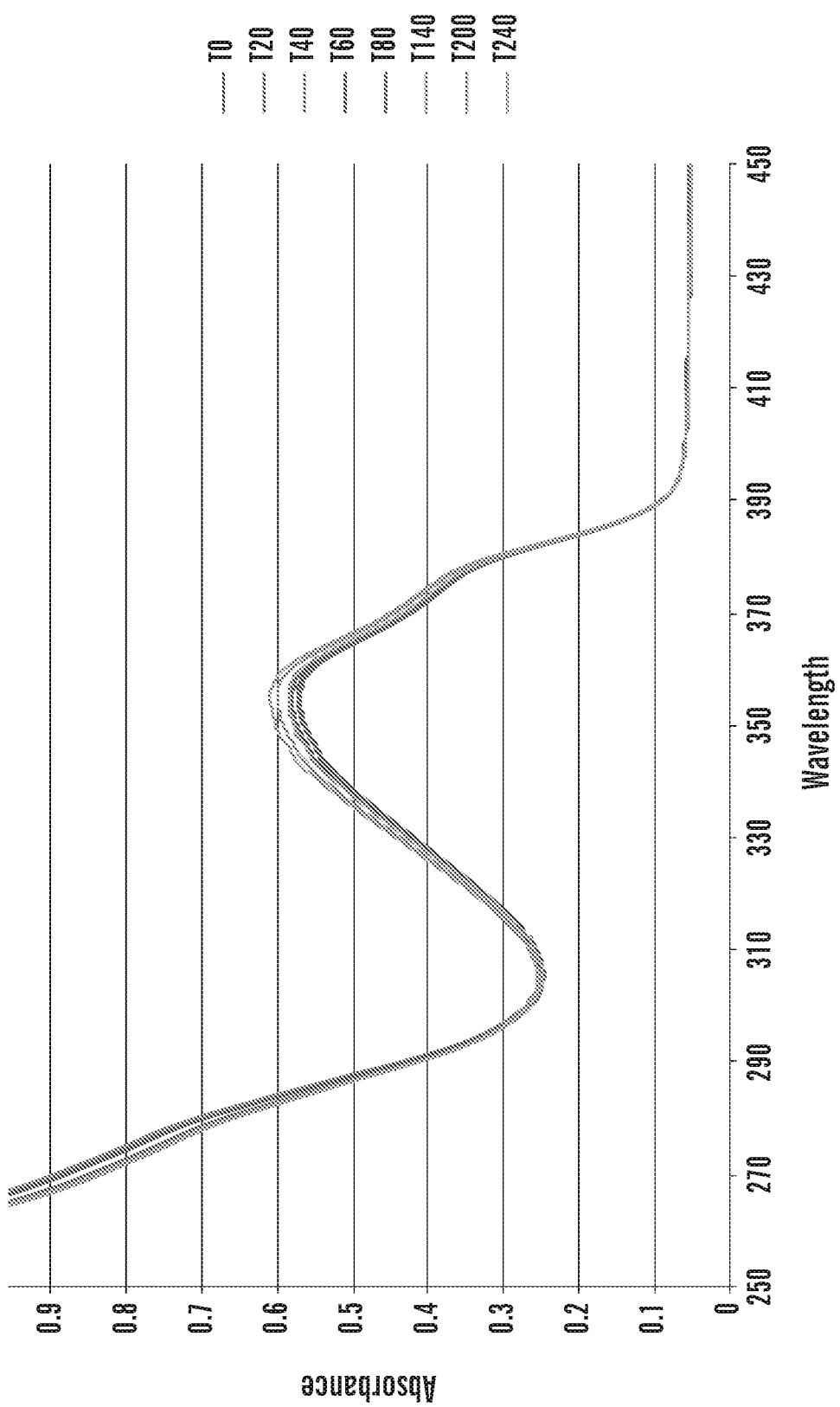
Figure 26:
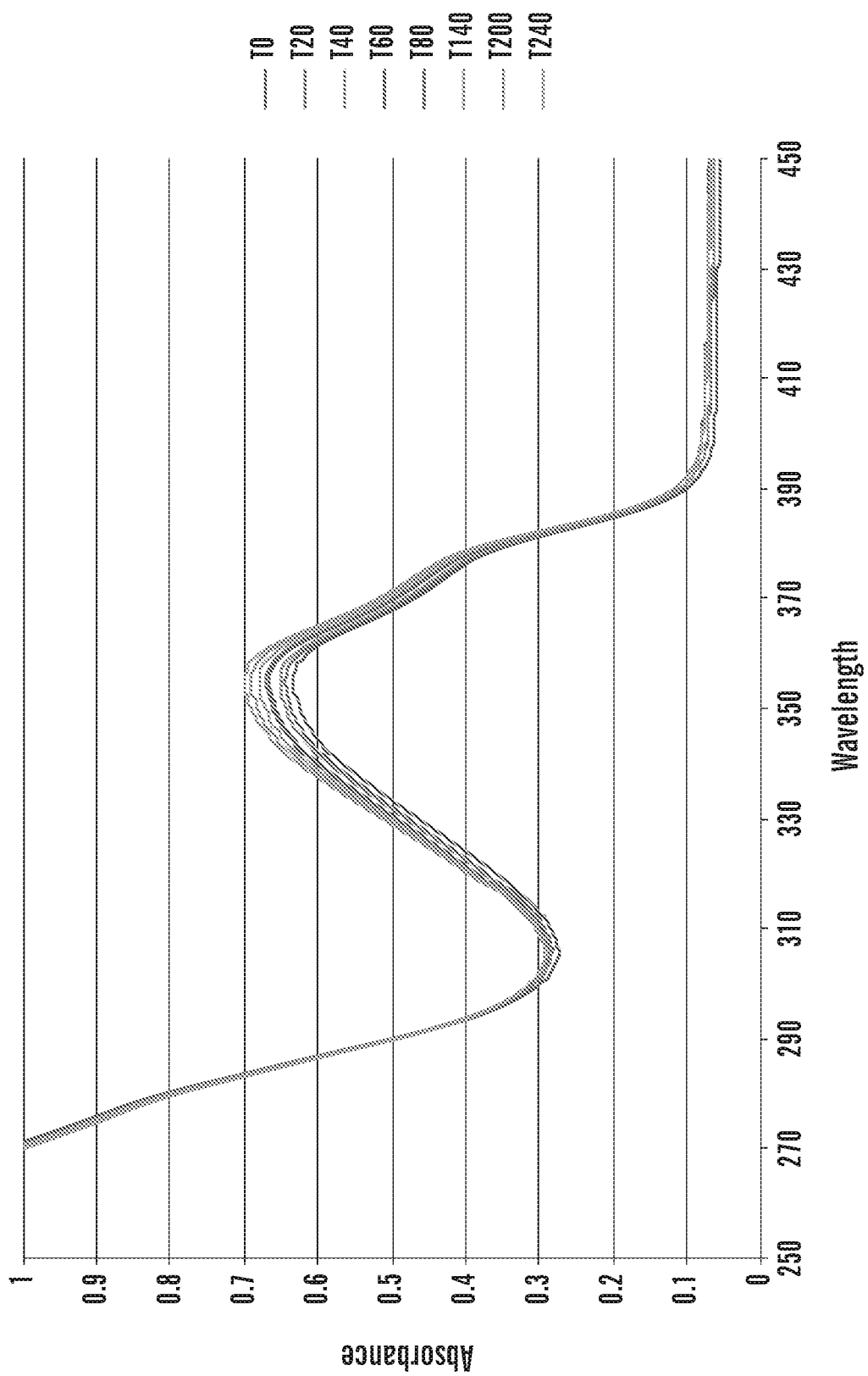
Figure 27:
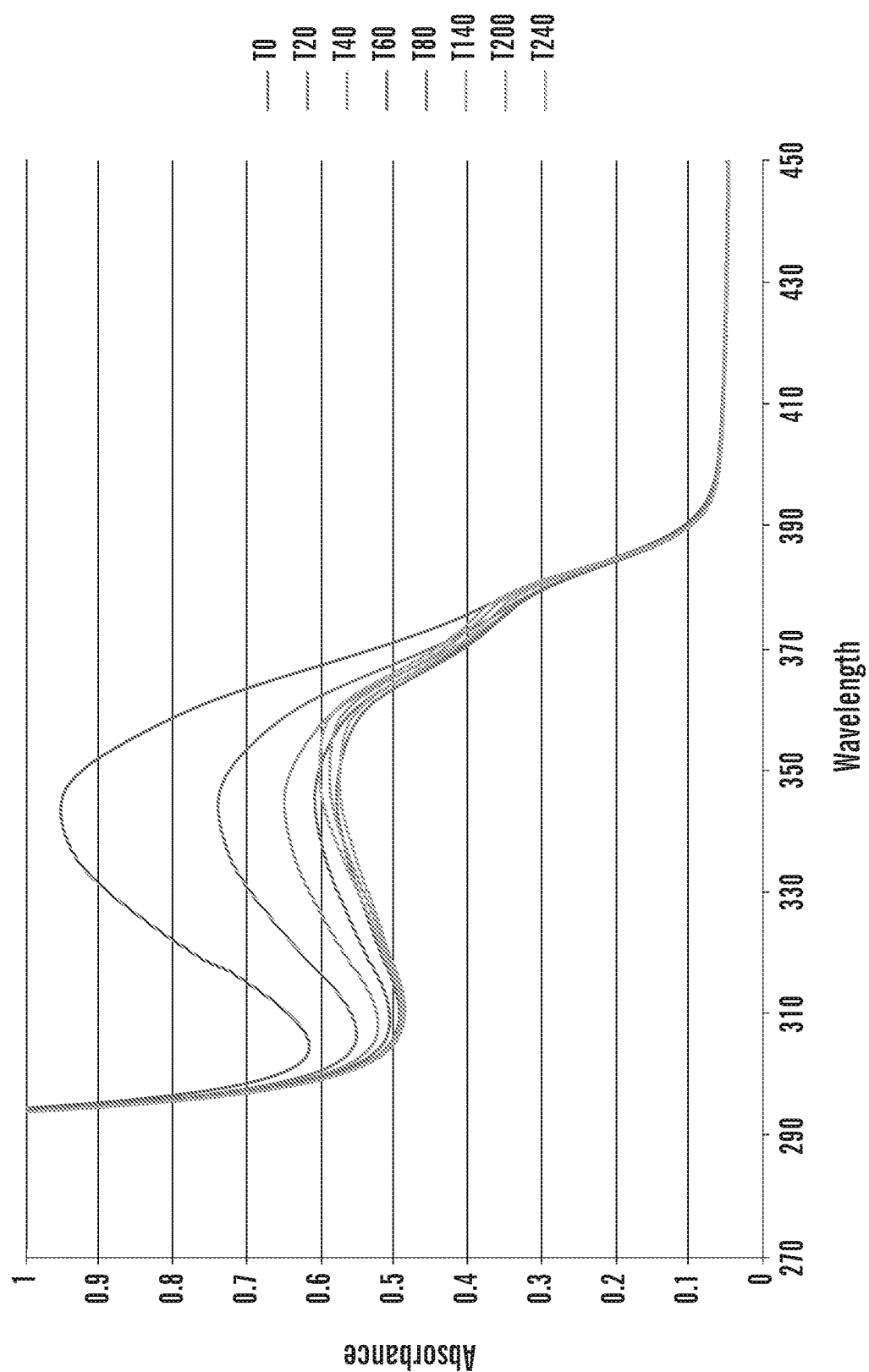
FIG. 27 is the UV degradation (run in triplicate) of G0 avobenzone conjugate with linker at 357 nM in ethylacetate. (Top graph: visible lines at ~347 nm are, from top to bottom: T0, T20, T40, T60, T240, T200, T80, T140. Center graph: visible lines at ~347 nm are, from top to bottom: T0, T20, T40, T60, T240, T80, T200, T140. Bottom graph: visible lines at ~347 nm are, from top to bottom: T0, T20, T40, T60, T80, T240, T200, T140.)
Figure 27:
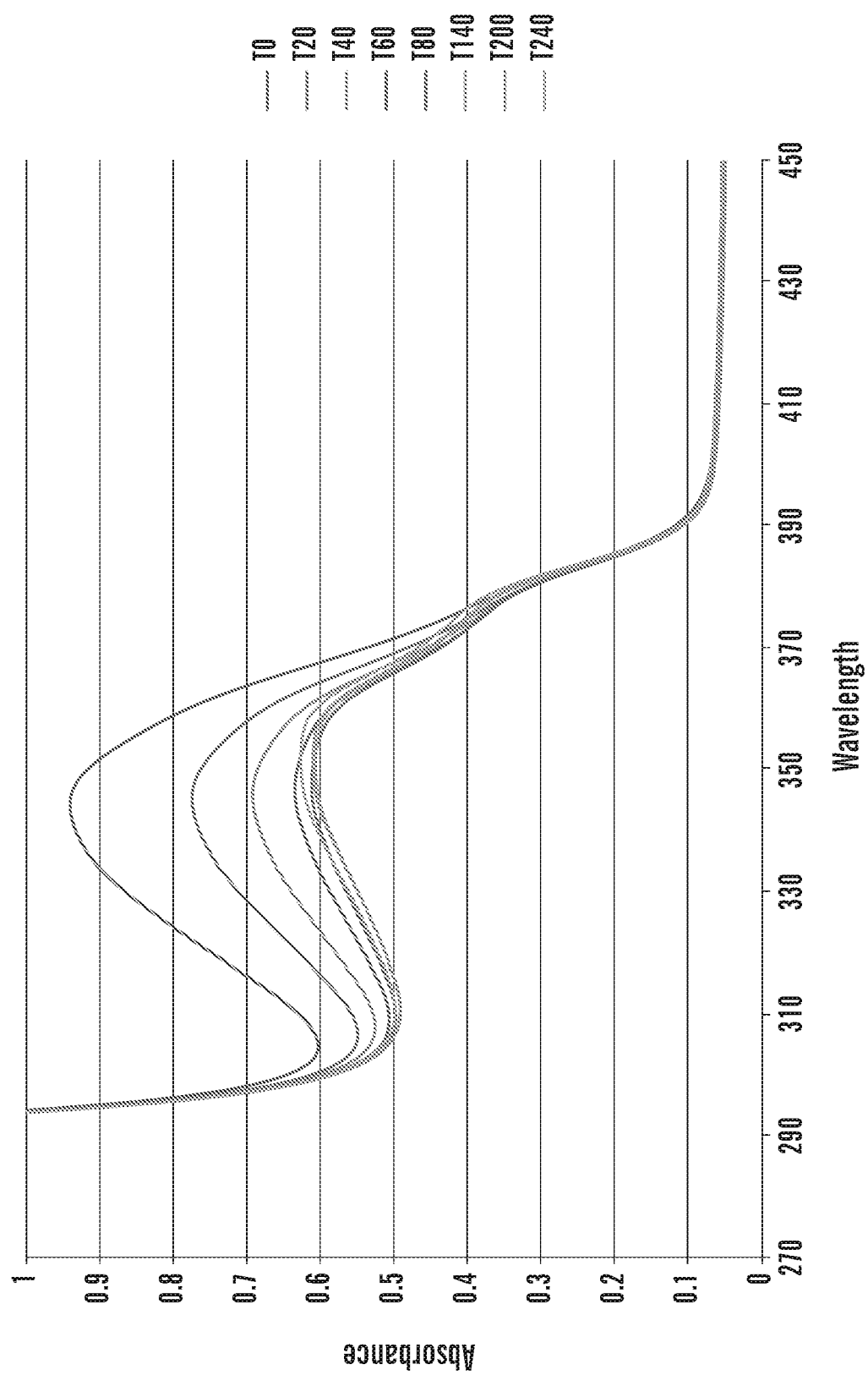
Figure 27:
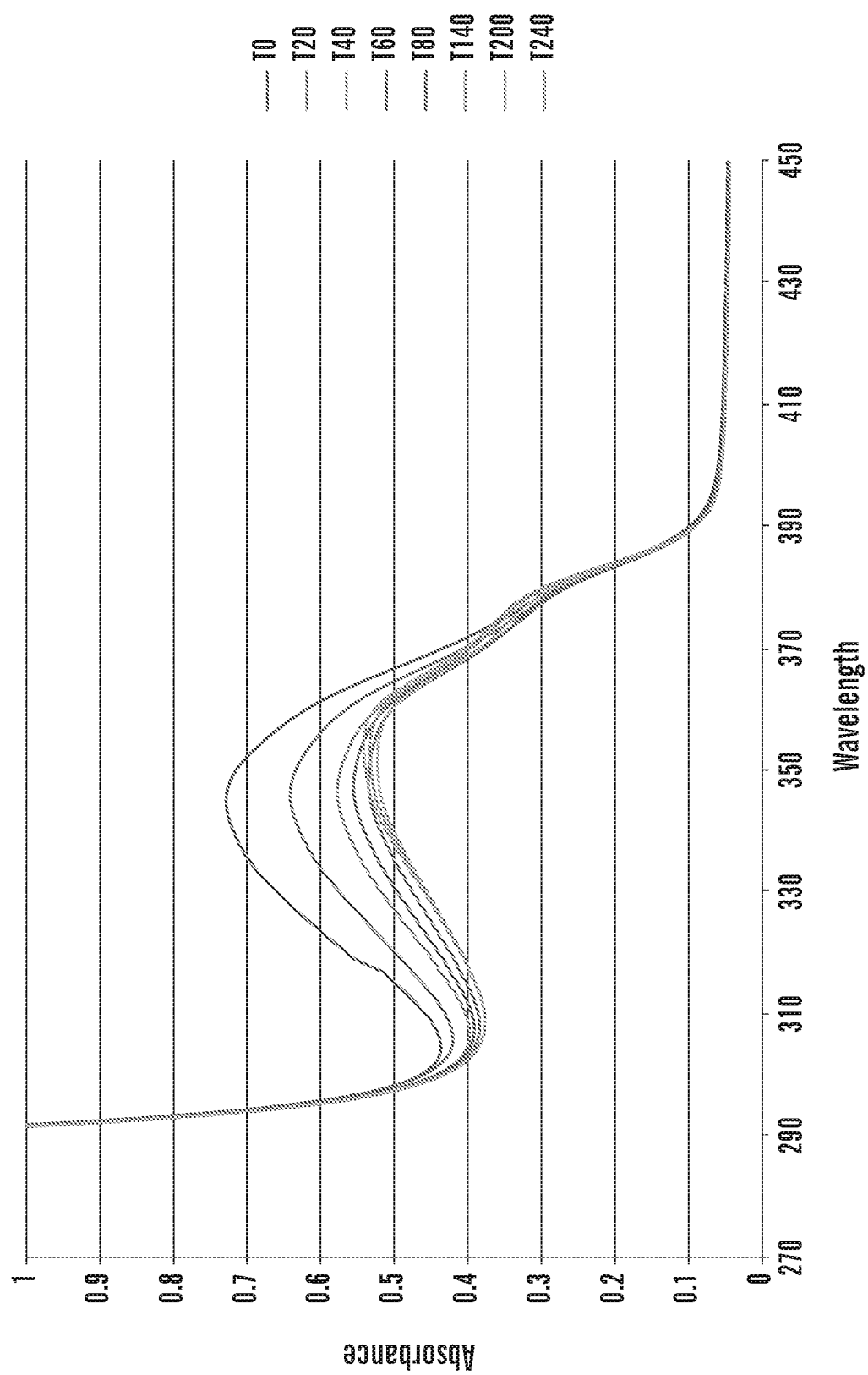
Figure 28:
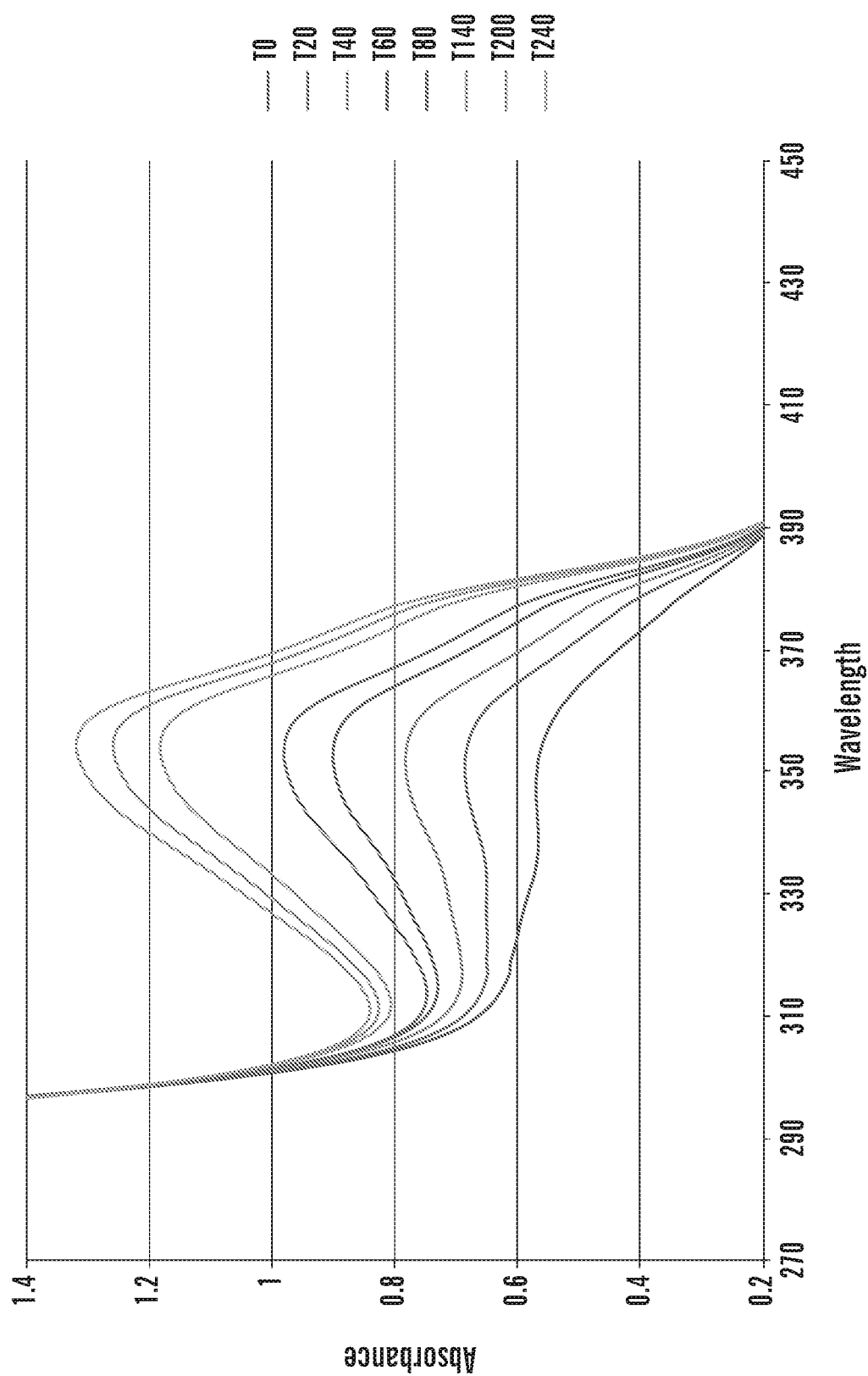
FIG. 28 is the UV degradation (run in triplicate) of G1 Newkome-type avobenzone conjugate at 357 nM in ethyl acetate. (All three graphs: visible lines at ~357 nm are, from top to bottom: T240, T200, T140, T80, T60, T40, T20, T0.)
Figure 28:
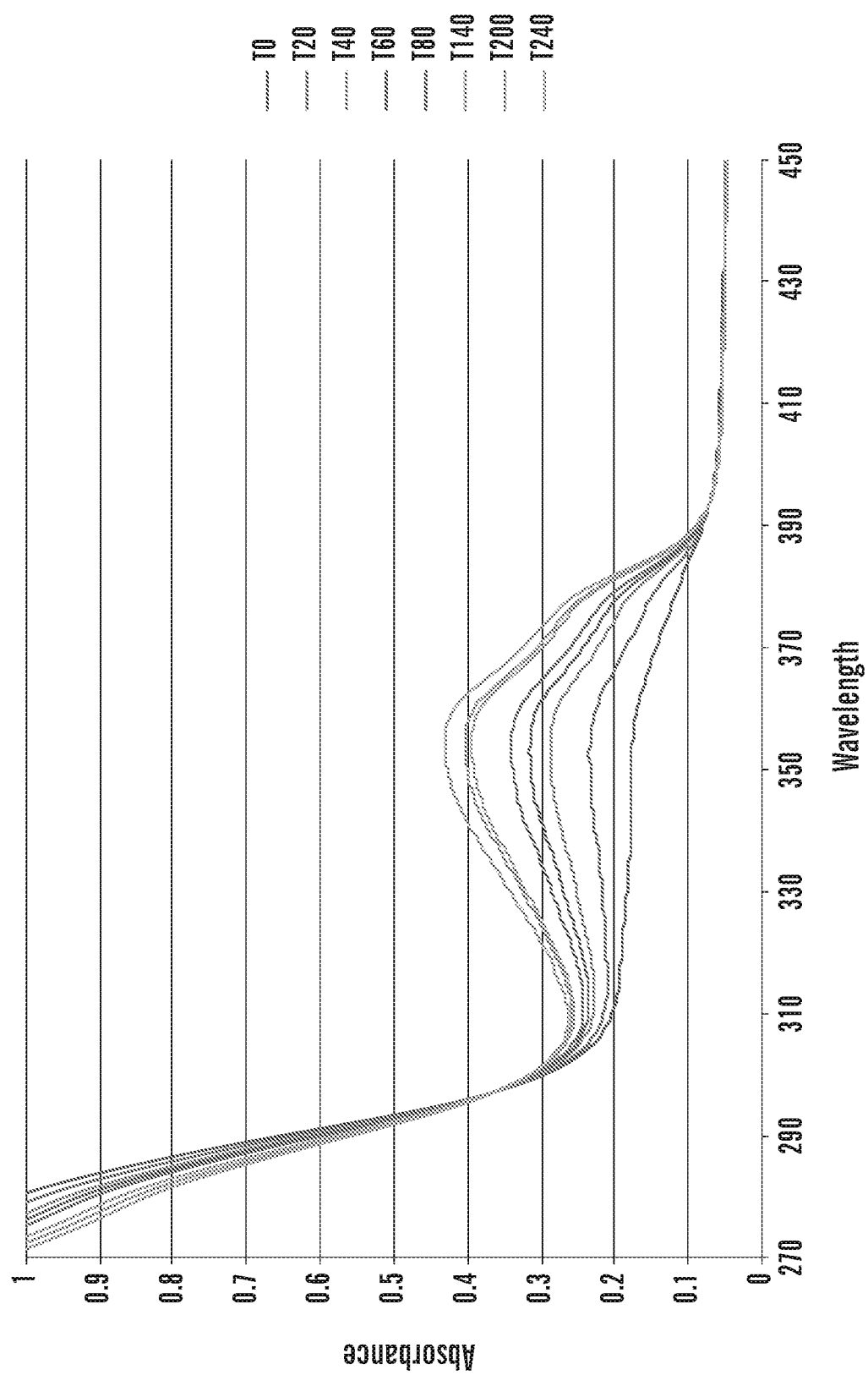
Figure 28:
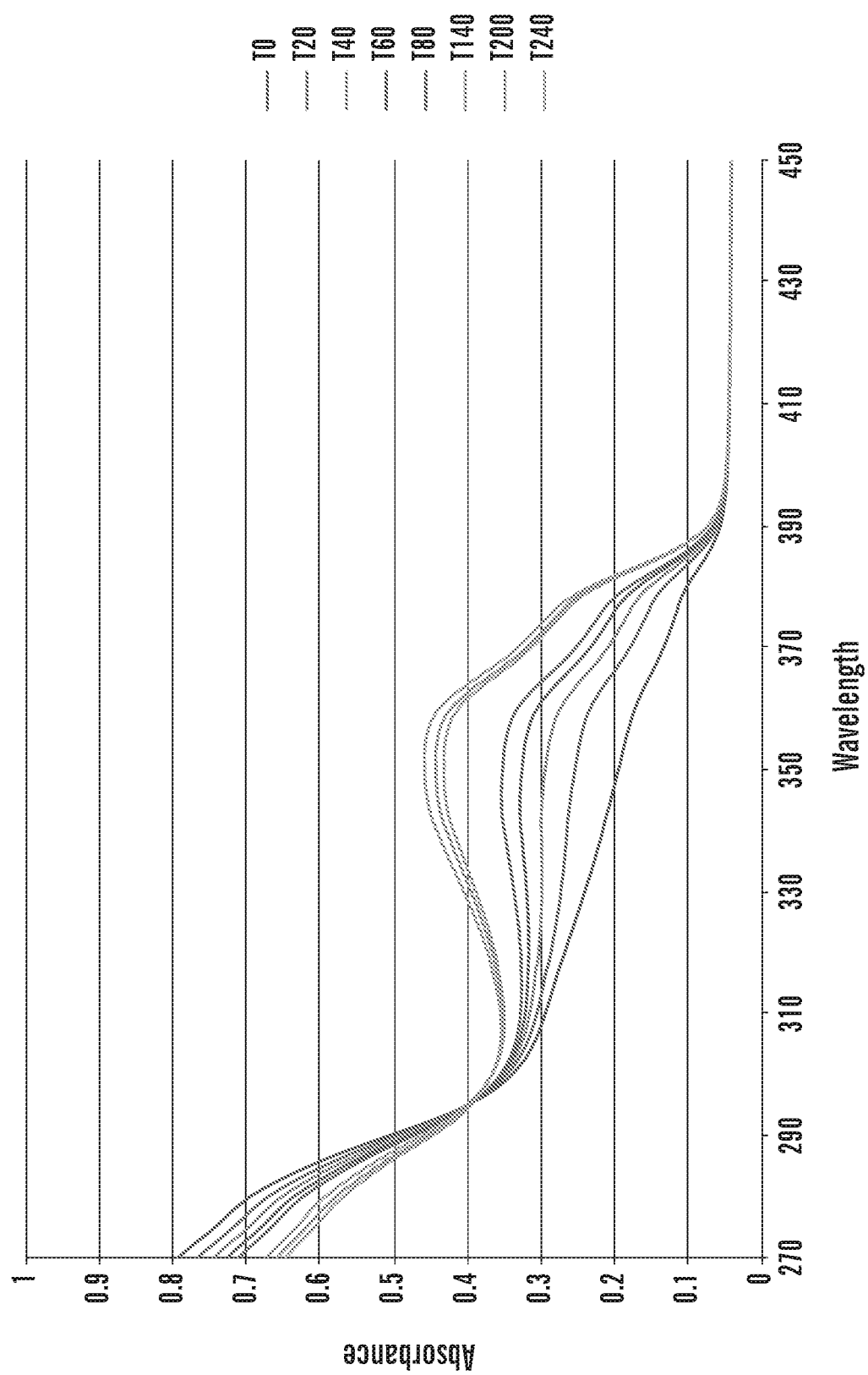
Figure 29:
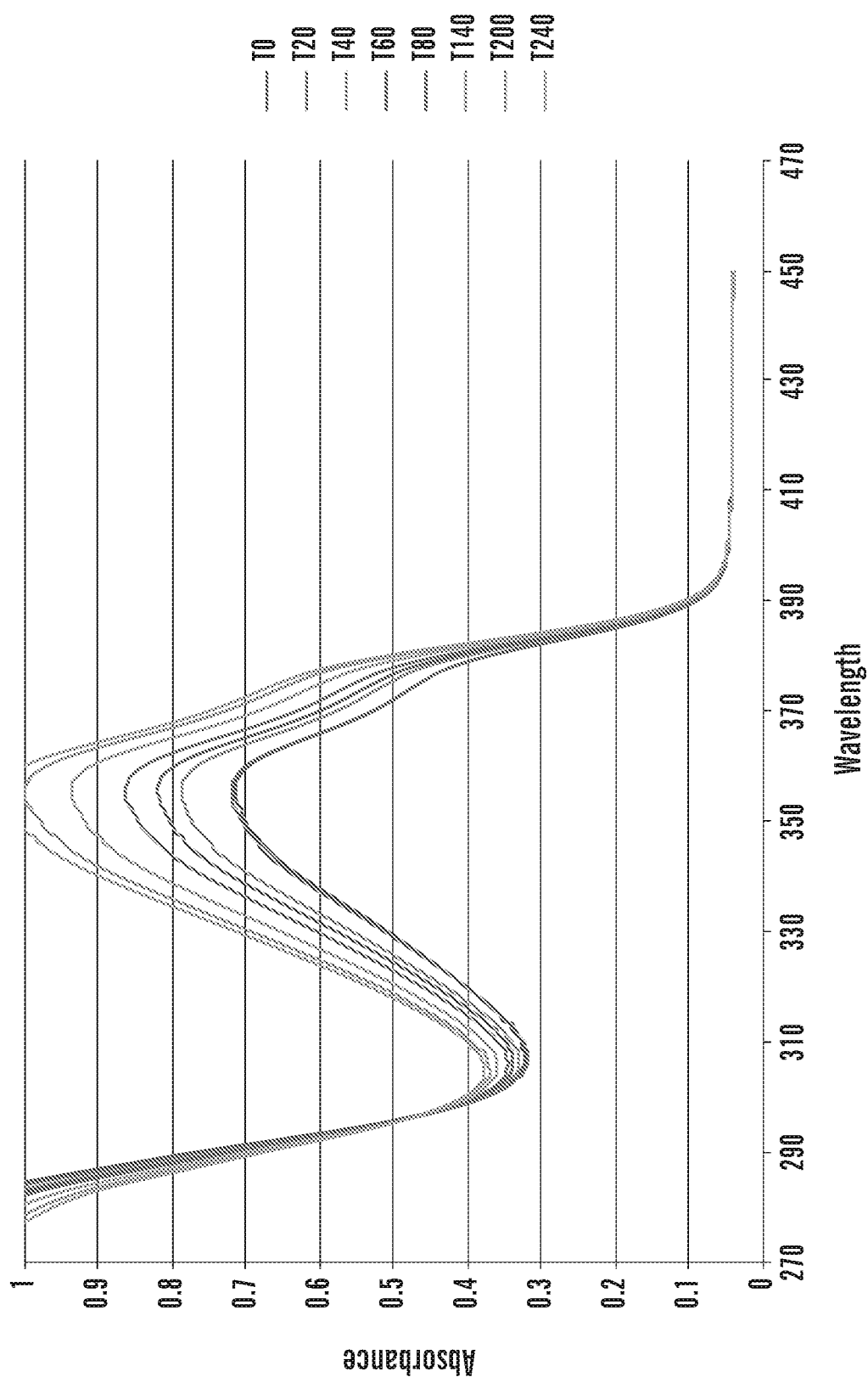
FIG. 29 is the UV degradation (run in duplicate) of G1 Newkome-type avobenzone conjugate at 357 nM in ethyl acetate with 1 weight percent TWEEN®. (Top graph: visible lines at ~357 nm are, from top to bottom: T240 (cut off at peak), T200, T140, T80, T60, T40, T20, T0. Bottom graph: visible lines at ~357 nm are, from top to bottom: Series 8, Series 6, Series 5, Series 4, Series 3, Series 1, Series 2.)
Figure 29:
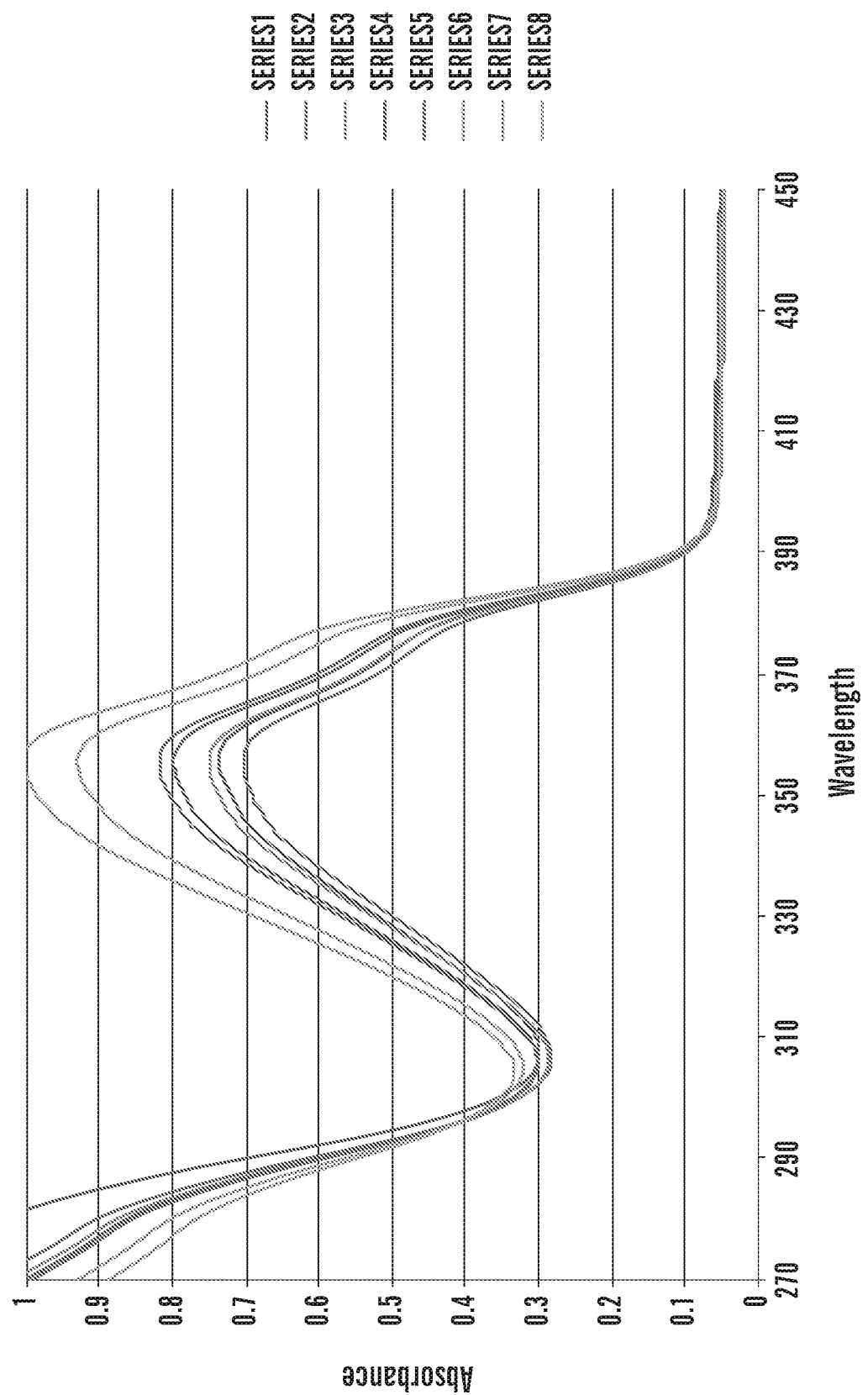
Figure 30:
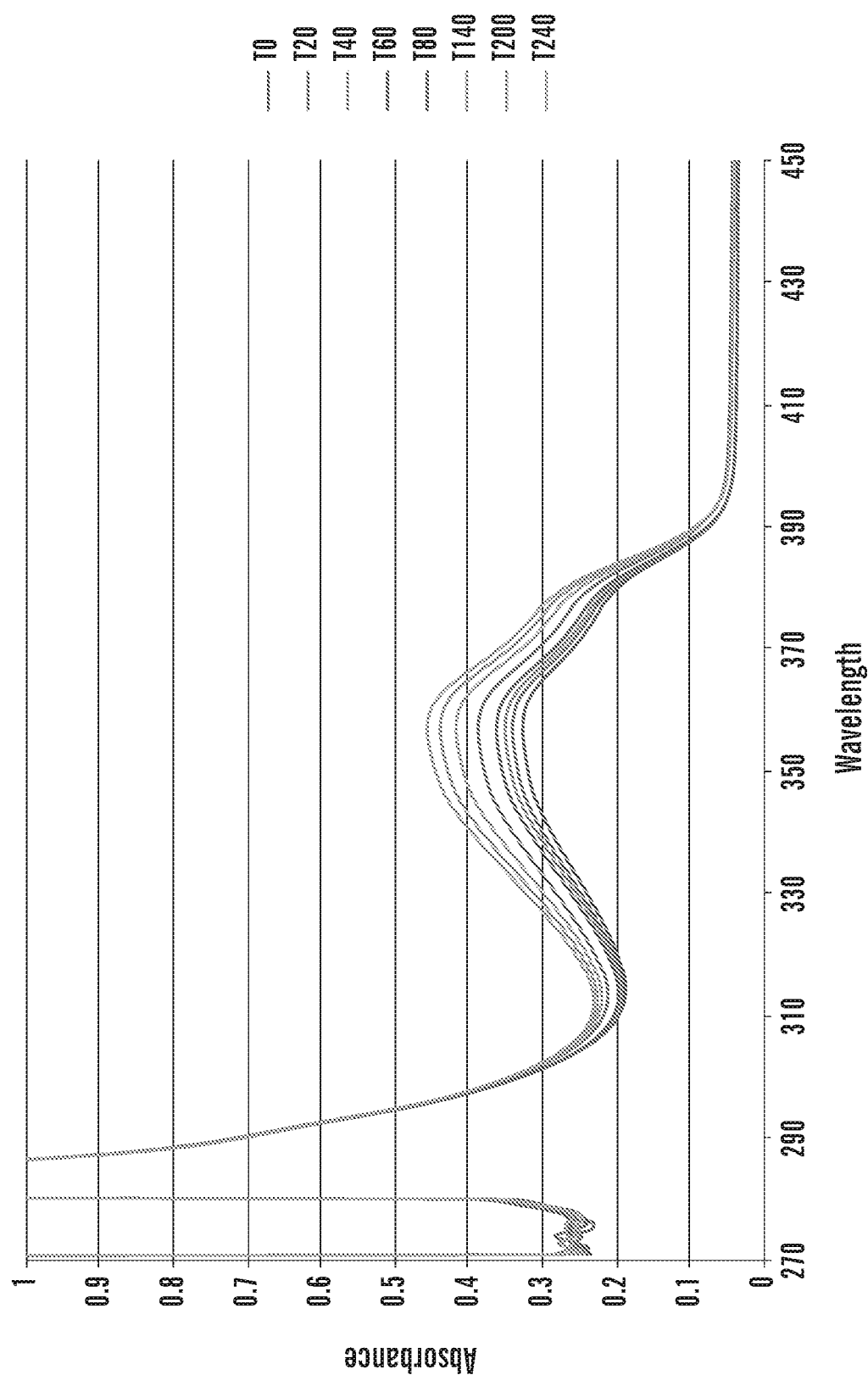
FIG. 30 is the UV degradation (run in duplicate) of G1 Newkome-type avobenzone conjugate at 357 nM in toluene. (Both graphs: visible lines at ~357 nm are, from top to bottom: T240, T200, T140, T80, T60, T40, T20, T0.)
Figure 30:
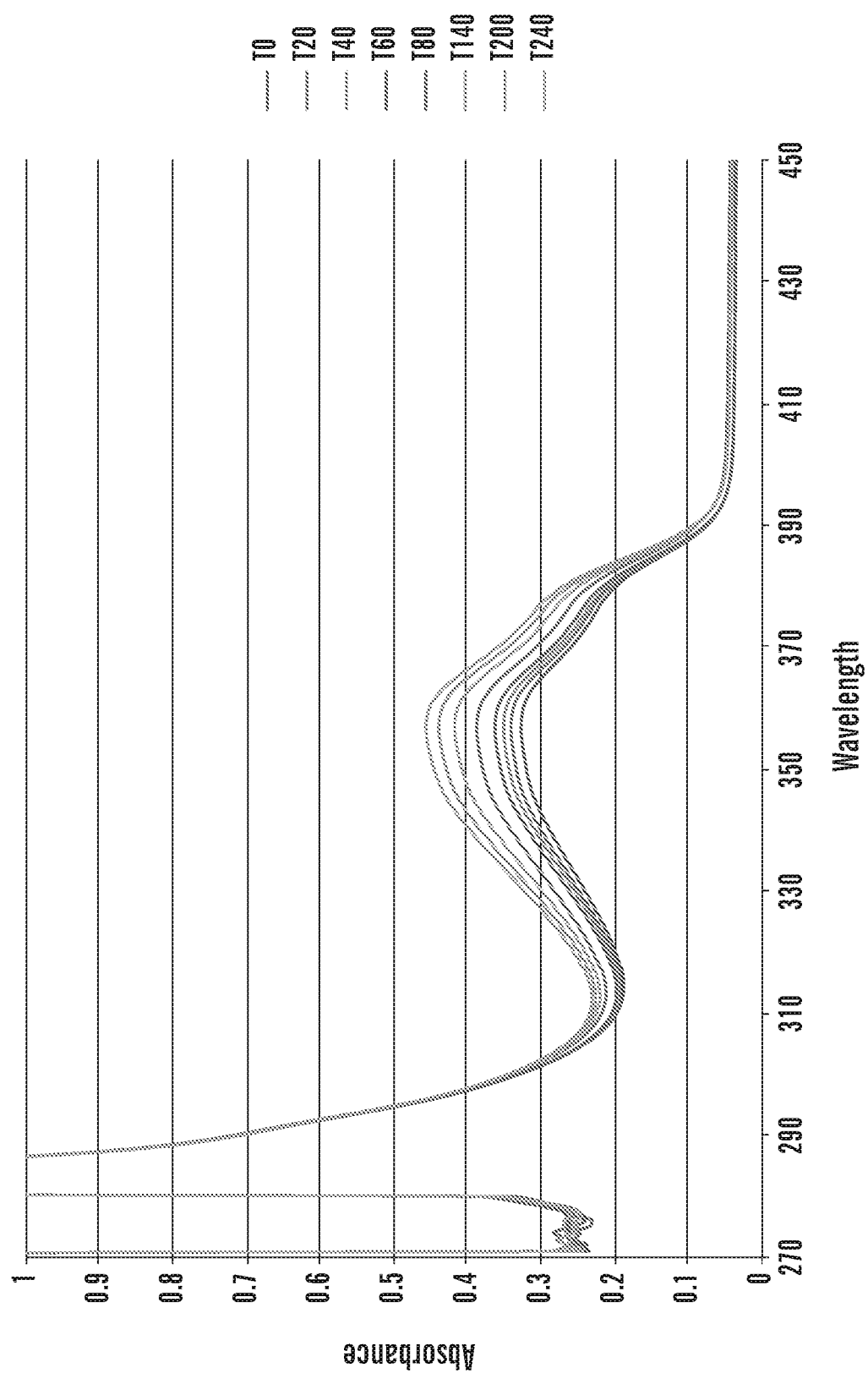
Figure 31:
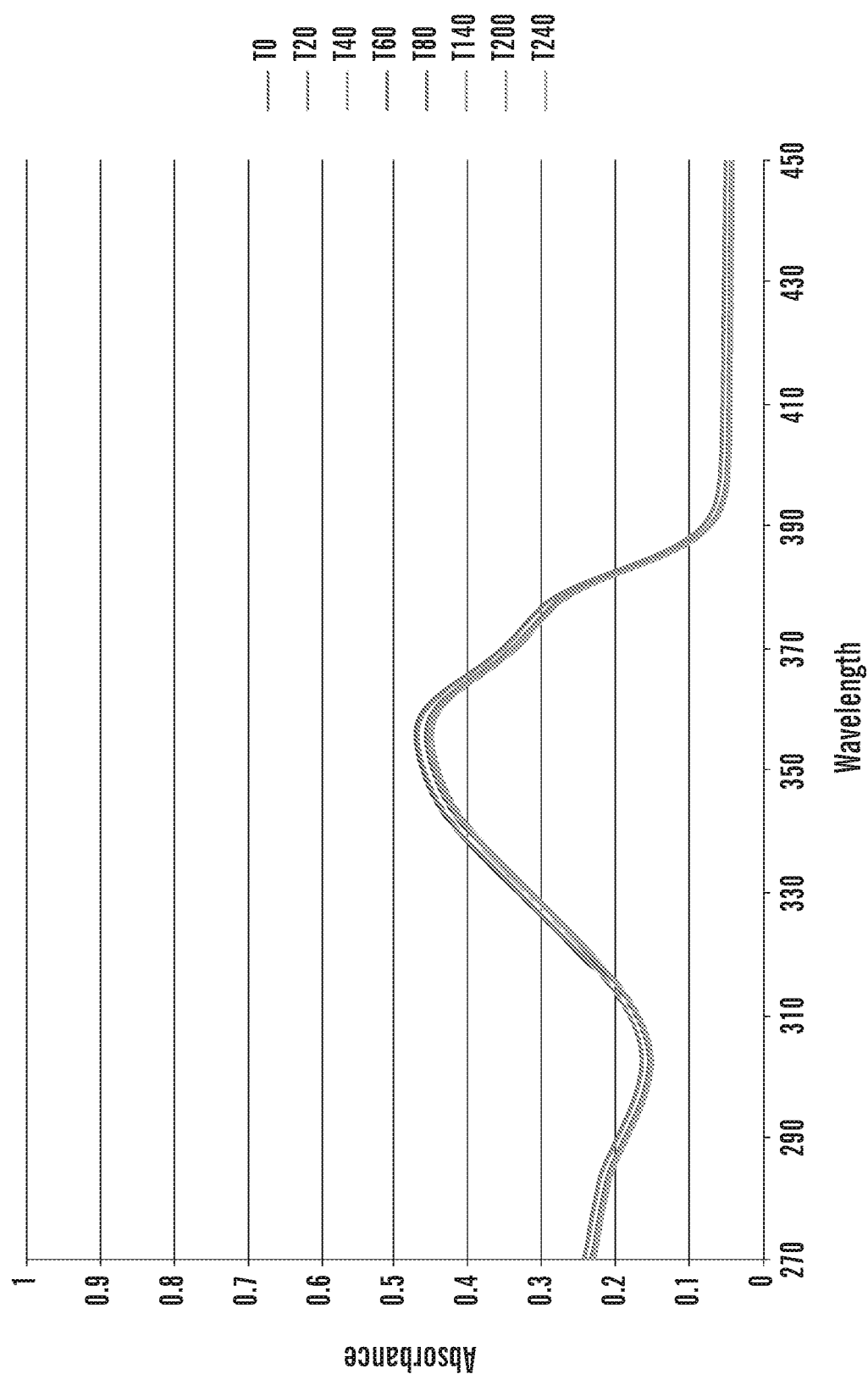
FIG. 31 is the UV degradation (run in triplicate) of G2 Newkome-type avobenzone conjugate at 357 nM in ethyl acetate. (Top graph: visible lines at ~357 nm are, from top to bottom: T0, T40, T80, T140, T200, T240. Center graph: visible lines at 357 nm are, from top to bottom: T0, T20, T40, T60, T80, T140, T200, T240. Bottom graph: visible lines at ~357 nm are, from top to bottom: T0, T20, T140, T240.)
Figure 31:
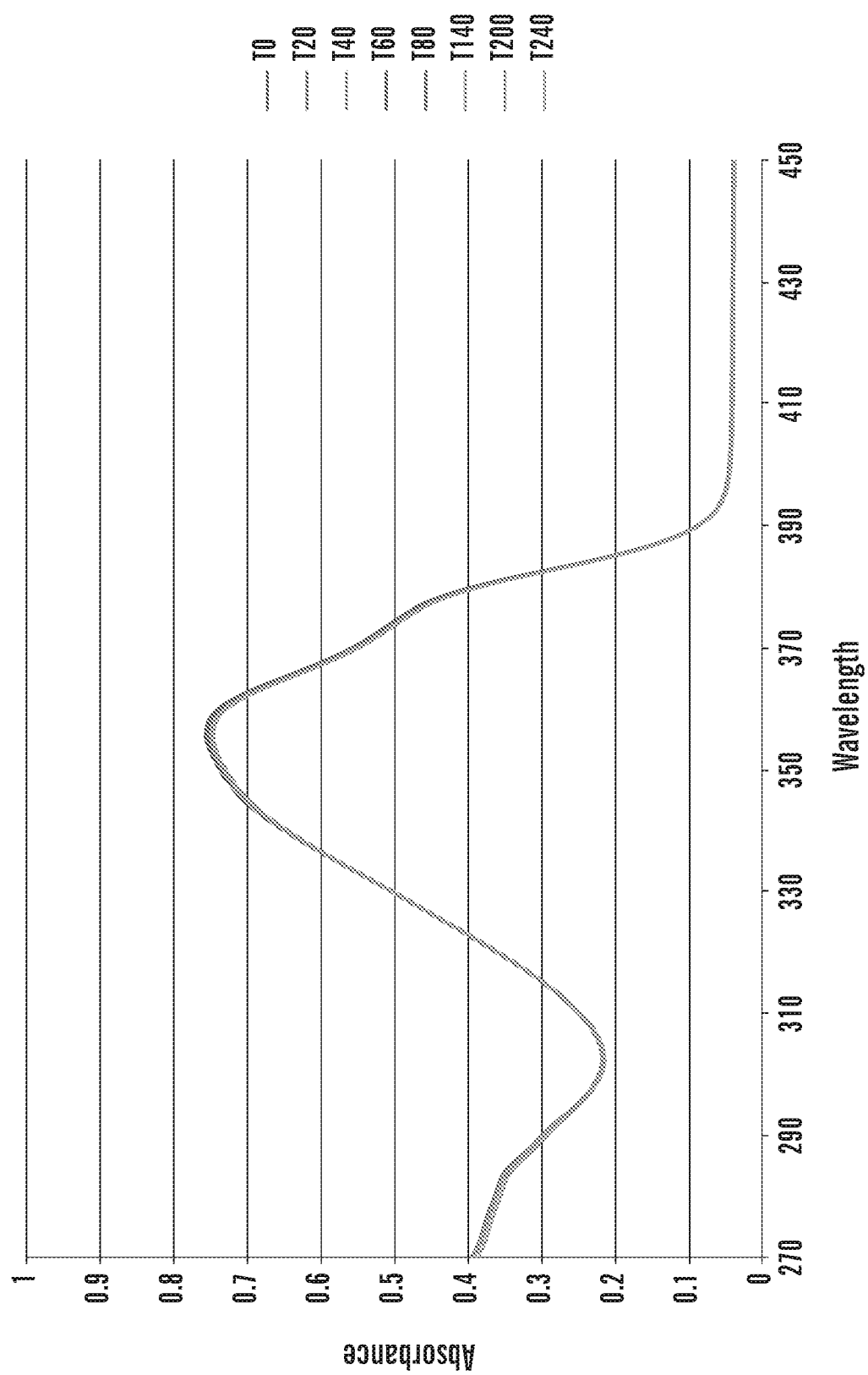
Figure 31:
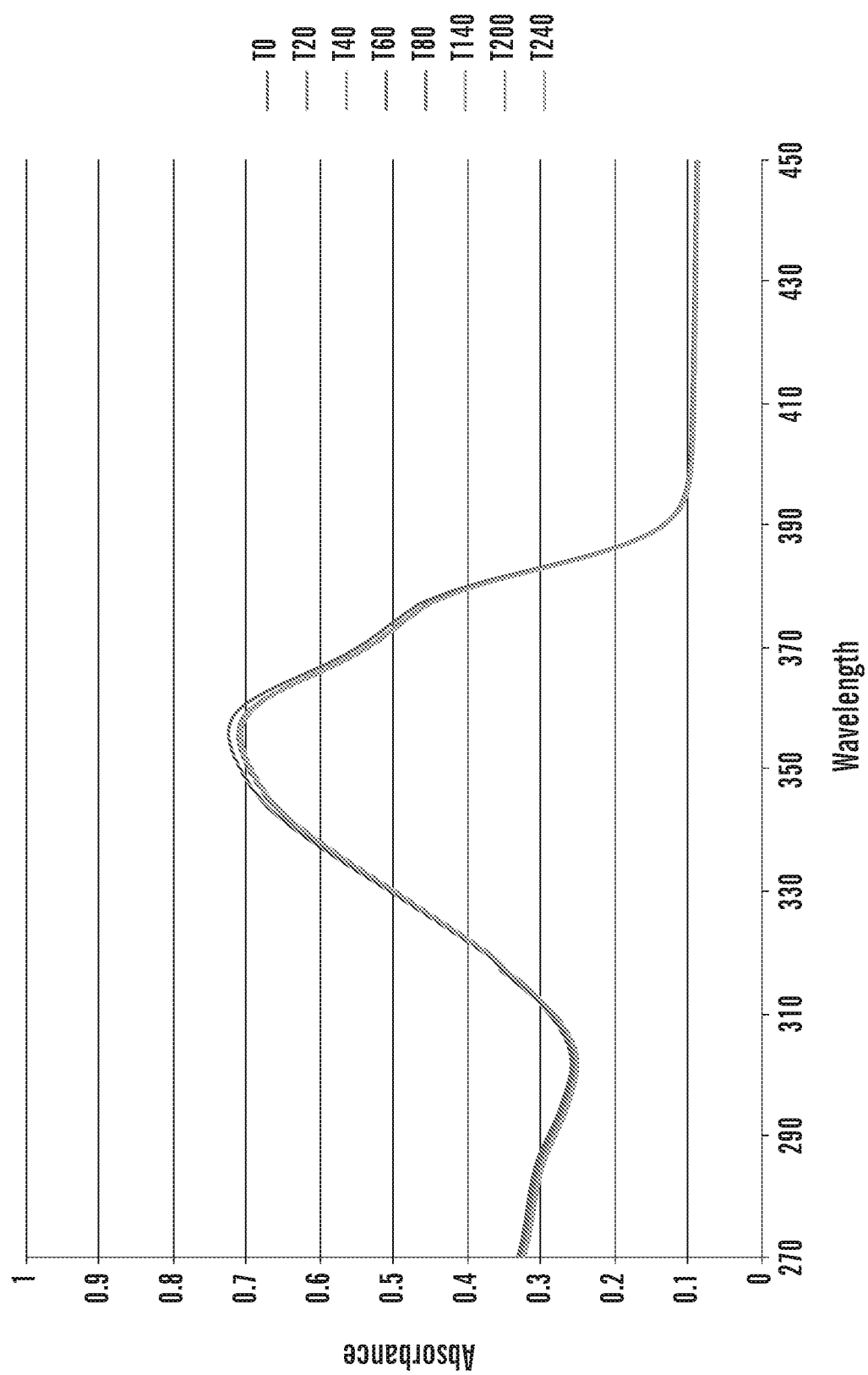
Figure 32:
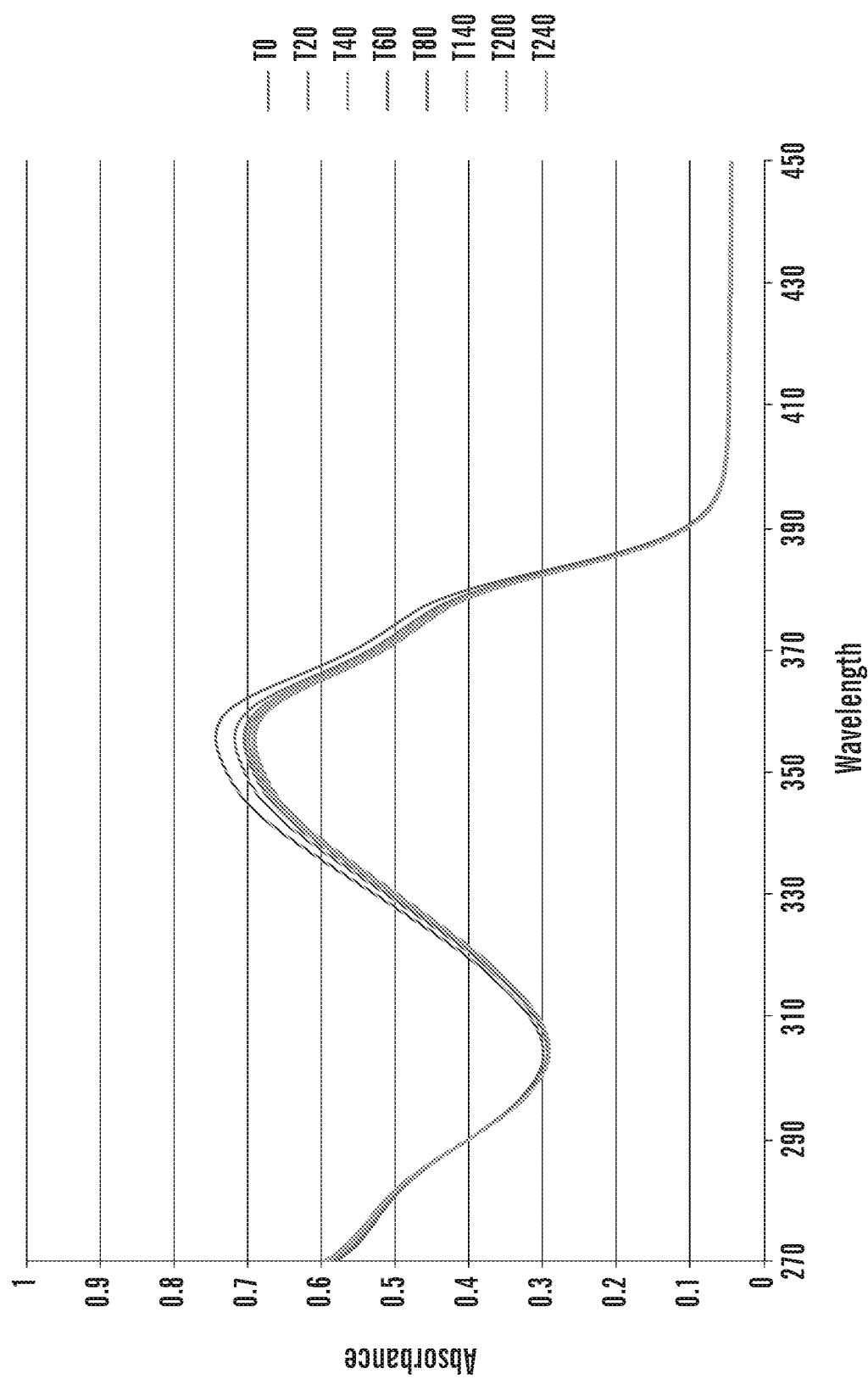
FIG. 32 is the UV degradation (run in triplicate) of G2 PAMAM avobenzone conjugate at 357 nM in ethyl acetate. (Top graph: visible lines at ~357 nm are, from top to bottom: T0, T20, T40, T60, T140, T240, T200. Center graph: visible lines at ~357 nm are, from top to bottom: T0, T20, T40, T60, T240, T140. Bottom graph: visible lines at ~357 nm are, from top to bottom: T0, T240, T140, T80, T200.)
Figure 32:
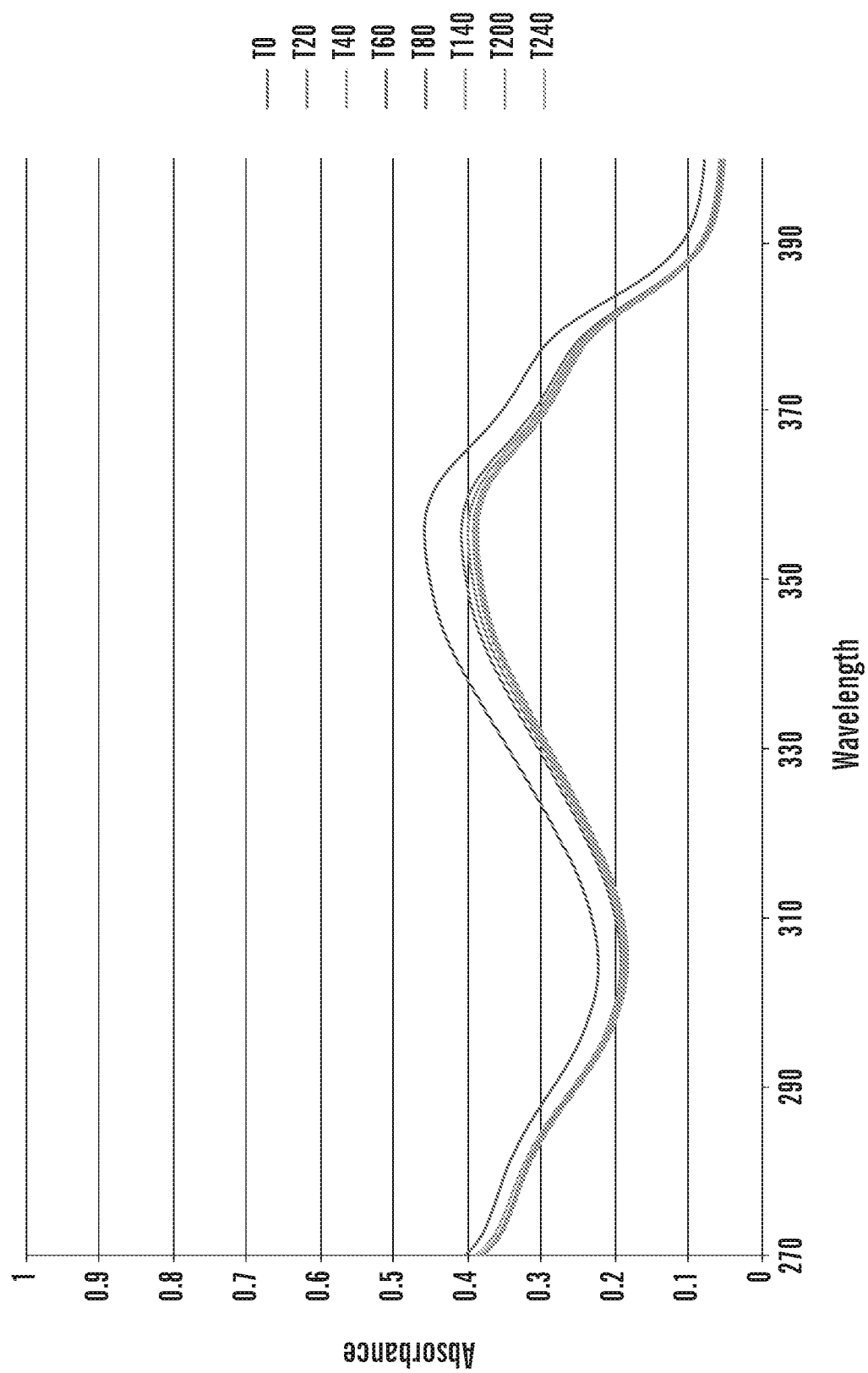
Figure 32:
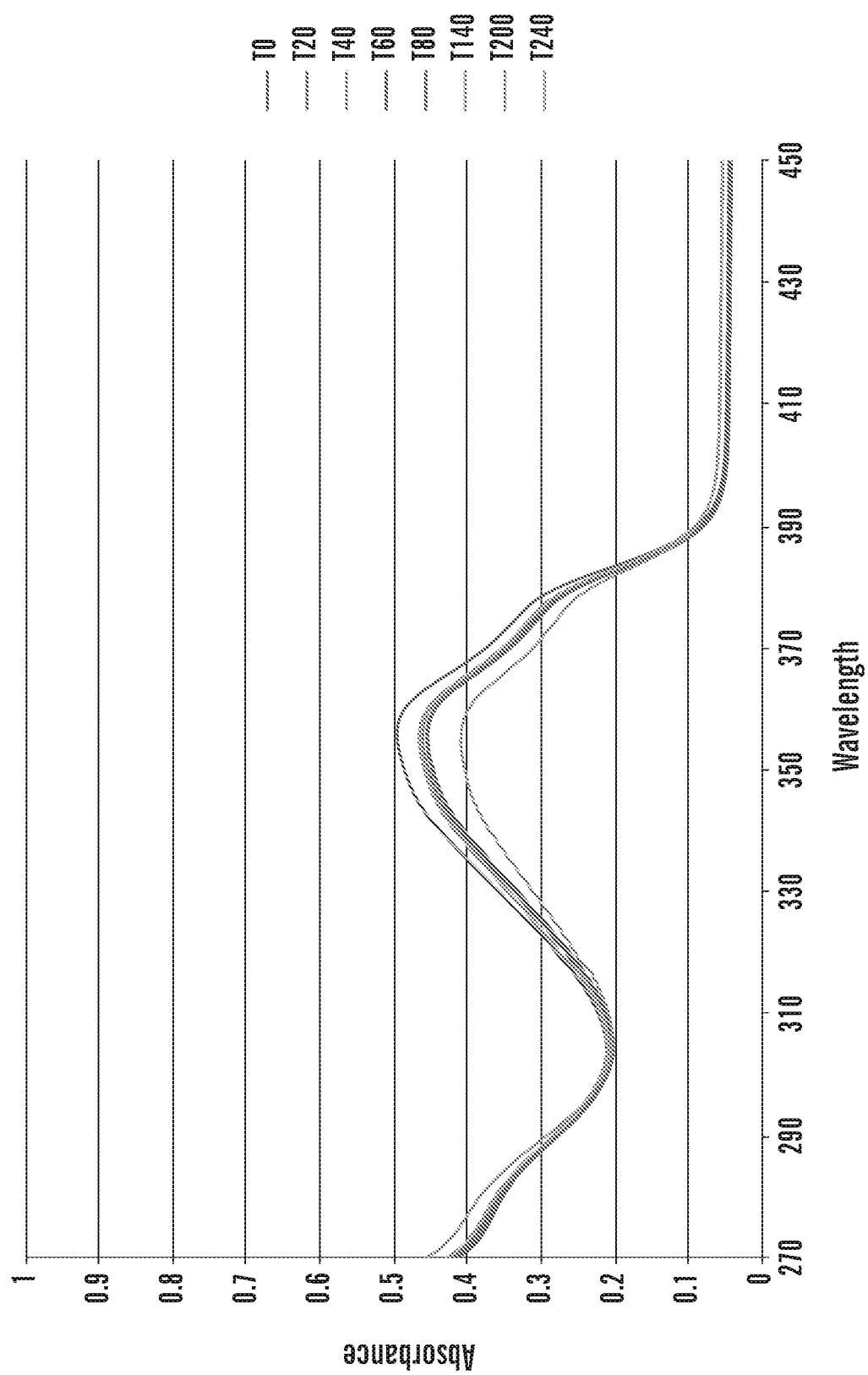
Figure 33:
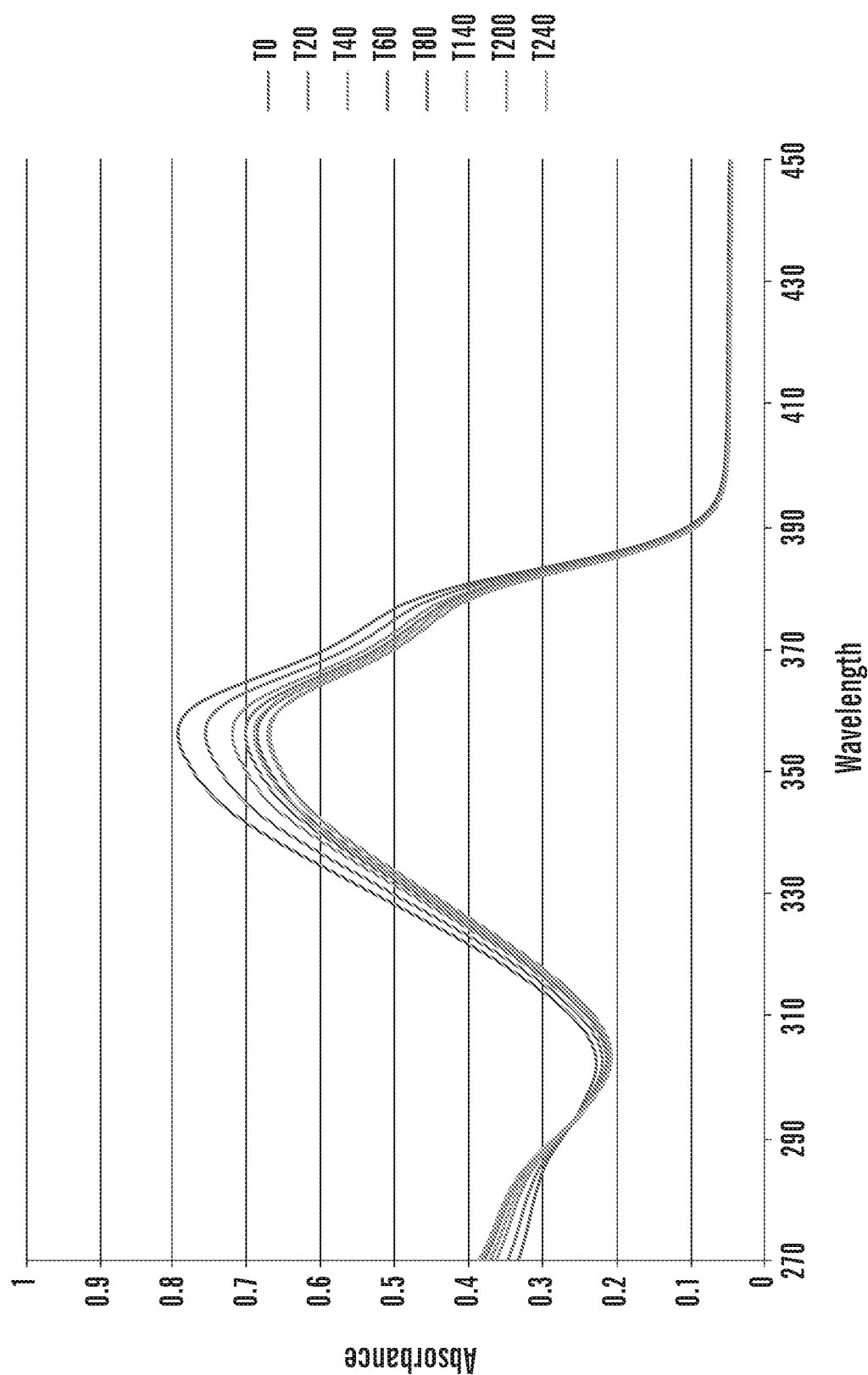
FIG. 33 is the UV degradation (run in triplicate) of G3 PAMAM avobenzone conjugate at 357 nM in ethyl acetate. (Top graph: visible lines at ~357 nm are, from top to bottom: T0, T20, T40, T80, T240, T60, T200, T140. Center graph: visible lines at ~357 nm are, from top to bottom: T0, T240, T20, T60, T80, T140. Bottom graph: visible lines at ~357 nm are, from top to bottom: T0, T20, T40, T60, T80, T140, T240, T200.)
Figure 33:
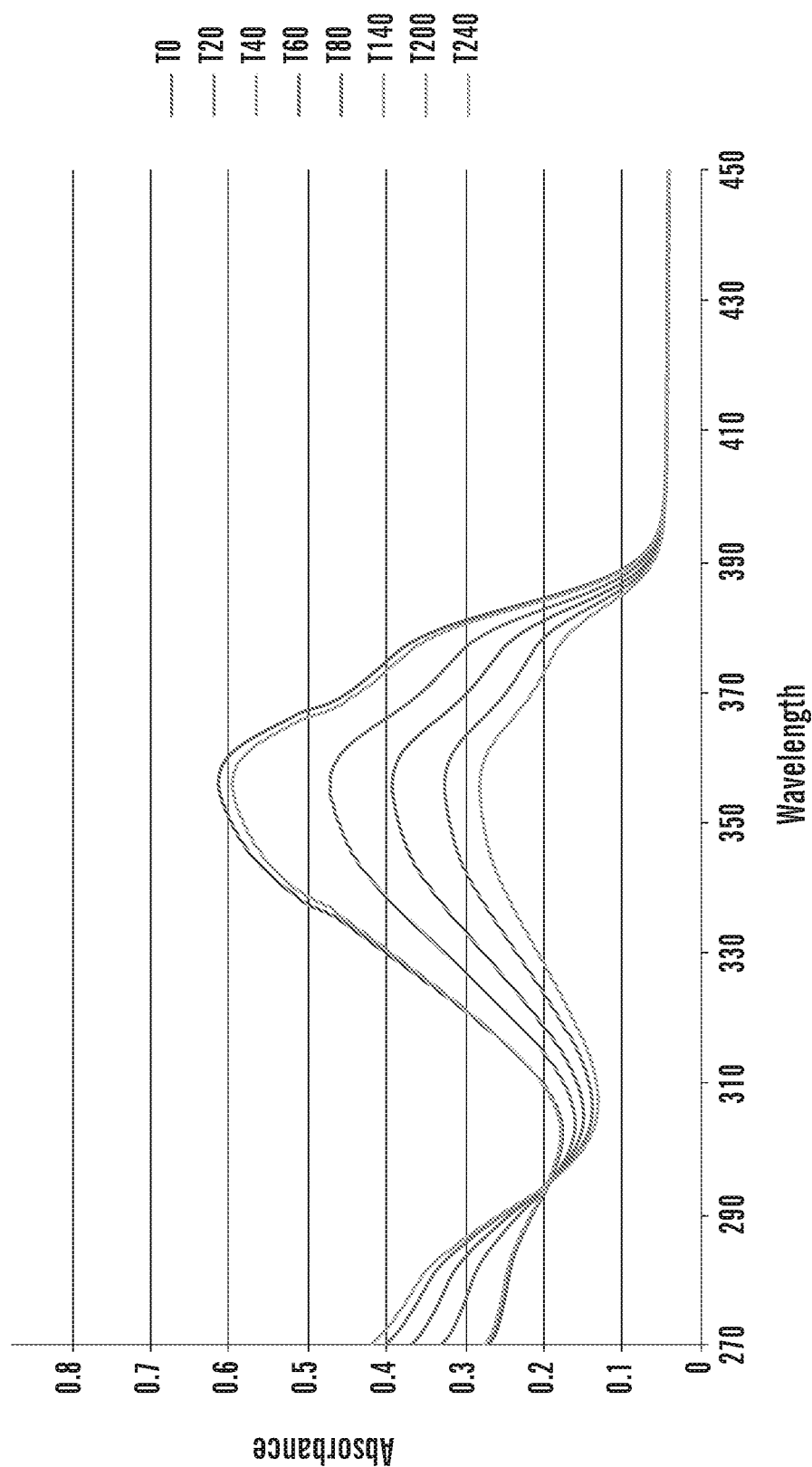
Figure 33:
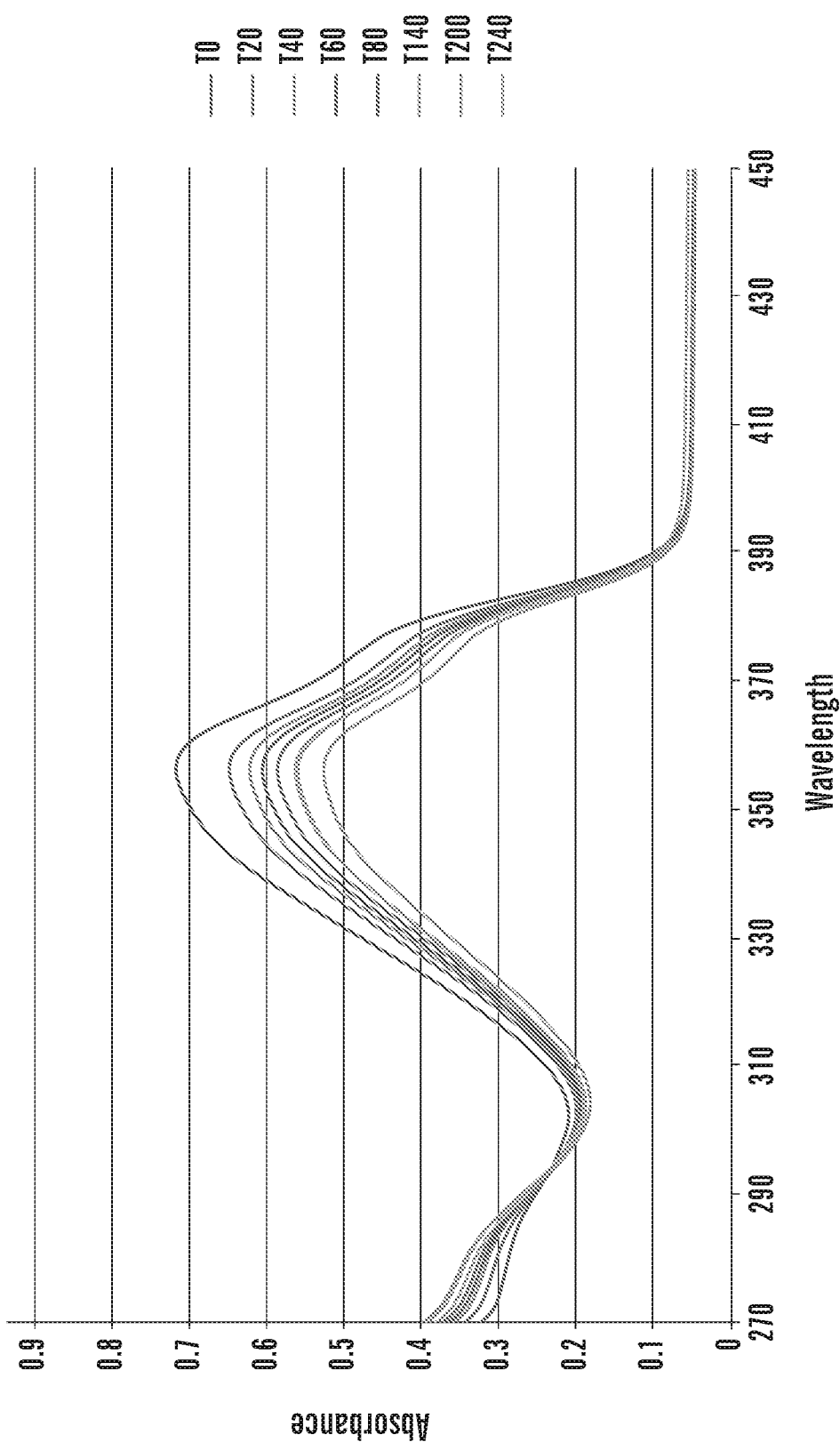

Avobenzone and the avobenzone conjugates were each dissolved in ethyl acetate, unless otherwise noted, and sealed in airtight quartz cuvettes. UV absorbance was measured and the cuvette was left under a UV light at 367 nm for a four hour period with UV absorbance measured at 20 minutes, 40 minutes, 60 minutes, 80 minutes, 140 minutes, 200 minutes, and 240 minutes. The avobenzone decay curves were run in triplicate and extra decay curves run in duplicate. The results are shown in FIG. 25 through FIG. 24.

Discussion of Examples 1-9

Polymers can stabilize photoactive compounds by holding them in arrangements that shield the chromophore from degradation or in arrangements that make it less prone to photobleaching (Furuta et al., *J. Am. Chem. Soc.* 125:13165-72 (2003), which is hereby incorporated by reference in its entirety). Dendrimers present a particularly interesting polymer scaffold for cosmetic actives in several regards. The monodisperse nature of dendrimers allows for exact control over a new ingredient, reducing impurities and easing the process of FDA approval. Dendrimers have been shown to have good thin film formation, an advantage when dispersing an active on skin (Tsukruk et al., *Langmuir* 13:2171-76 (1997); Tanner, *Dermatol. Clin.* 24:53-62 (2006), each of which is hereby incorporated by reference in its entirety). Additionally, the maximum intrinsic viscosity of dendrimers which corresponds to their switch to a globular form in solution allows the use of high generation dendrimers in formulations without the tacky feel associated with high viscosity formulations (Mourey et al., *Macromolecules* 25:2401-06 (1992), which is hereby incorporated by reference in its entirety).

While there have been many efforts to physically and/or to chemically stabilize avobenzone in formulations, they largely steer clear of chemically modifying the structure of avobenzone itself (U.S. Pat. No. 6,899,866 to Bonda; Yang et al., *Eur. J. Pharm.* 69:605-12 (2008), each of which is hereby incorporated by reference in its entirety). This is largely due to the FDA monograph on sunscreen additives, which requires FDA approval of new active sunscreen ingredients (Gaspar et al., *Int. J. Pharm.* 307:123-28 (2006); Gasparro et al., *Photochem. Photobiol.* 68:243-56 (1998); Sunscreen Drug Products for Over-the-Counter Human Use, 64 Fed. Reg. 27666 (May 21, 1999), each of which is hereby incorporated by reference in its entirety). This hurdle has been acknowledged by the United States government, which signed the Sunscreen Innovation Act (Public Law 113-195), allowing the FDA to streamline the procedure for bringing new filters to the market.

The creation of a new avobenzone derivative for use in sun care as well as the addition of a polymer that can act as both a scaffold and rheological modifier can change the way sunscreen is formulated. Additionally, if the polymer improved skin feel it could help improve compliance with sunscreen use and therefore lower the number of cases of skin cancer nationwide.

Avobenzone has a 1,3 diketo motif in the core of the molecule. The motif's acidic hydrogens can be substituted without greatly disturbing the absorbance properties of avobenzone due to the molecule retaining the ability to undergo enol-diketo tautomerizations. Substitution of a single hydrogen with a linker containing a functional handle allows avobenzone to be supported on a larger polymer scaffold. The choice of a hydroxylated linker allows for the formation of esters on an acid terminated dendrimer.

Polymer additives are widely used in cosmetic formulations to fulfill a variety of roles. Polymers can act as emulsifiers, film formers, or rheological modifiers (U.S. Pat. No. 7,175,834 to Aust et al.; U.S. Patent Application No. 2013/0243703 A1 to Barrett et al.; U.S. Pat. No. 7,964,245 to Bonda et al.; Nasu et al., *Colloids Surf A.* 326:92-97 (2008), each of which is hereby incorporated by reference in its entirety). The use of polymers as a scaffold for actives, however, has not been as widely explored. Film formation in cosmetic formulation is essential for several applications (U.S. Pat. No. 6,342,209 to Patil et al.; U.S. Pat. No. 6,482,400 to Collin et al., each of which is hereby incorporated by reference in its entirety). For skin-based application, film formation allows an even distribution of active ingredients across large surface areas (U.S. Pat. No. 6,060,547 to Canter et al.; U.S. Pat. No. 6,060,072 to Konik et al., each of which is hereby incorporated by reference in its entirety). Current film-forming polymers are often simple polymers without actives bound to the polymer itself. Polymers modified with functional handles can be used in their place and modified to have active ingredients loaded onto the polymer. Bare dendrimers of various kinds have been patented for use as film-forming additives in both hair care and sun care applications (U.S. Pat. No. 6,582,685 to Adams et al.; U.S. Pat. No. 6,287,552 to Tournilhac et al.; U.S. Pat. No. 6,001,342 to Forestier et al., each of which is hereby incorporated by reference in its entirety). Hydroxyl terminated dendrimers show low cell toxicity and have been shown to increase the effectiveness of some formulations (U.S. Pat. No. 6,582,685 to Adams et al., which is hereby incorporated by reference in its entirety).

Dendrimers can be modified easily. PAMAM and Newkome-type dendrimers have both been studied in biological systems and, when cationic surface charges are not present, both have shown low cell toxicity (Yiyun et al., *J. Pharm. Sci.* 96 (3):595-602 (2007); Eichman et al., *Pharm. Sci. Technol. Today* 3:232-45 (2000); Forstner et al., *Biomacrorolecules* 15:2461-74 (2014), each of which is hereby incorporated by reference in its entirety). The 1→2 branching of the PAMAM dendrimer affords fewer termini per generation compared to the 1→3 branching of the Newkome type dendrimer (GEORGE R. NEWKOME ET AL., DENDRIMERS AND DENDRONS: CONCEPTS, SYNTHESIS, APPLICATIONS (2001); Newkome et al., *Chem. Rev.* 110:6338-42 (2010), each of which is hereby incorporated by reference in its entirety). PAMAM dendrimers are, however, commercially available and well-studied, making both dendrimers viable choices for modification with avobenzone.

To probe the potential advantages of a dendrimer-supported avobenzone, three generations of PAMAM dendrimers and three generations of Newkome-type dendrimers were modified with avobenzone attached to a linker. The resulting materials were tested for UV activity, film forming ability, and light stability.

Avobenzone was modified with 11-bromo-1-undecanol via a substitution reaction catalyzed by DBU and accelerated in the microwave. This yielded a hydroxyl handle that can be coupled to dendrimers containing carboxylic acids on the periphery. Both Newkome-type and PAMAM dendrimers were synthesized with free terminal acids and used for ligation to the modified avobenzone.

Succinated PAMAM dendrimers were purchased and used as received. All Newkome-type dendrimers were synthesized from commercially available dendrons di-t-butyl-4-[2-(t-butoxycarbonyl) ethyl]-4-aminoheptanedi carboxylate (aminotriester) and 4-(2-carboxyethyl)-4-nitroheptanedioic acid (nitrotriacid) purchased from Fischer Scientific and used as received.

Newkome-type dendrons were synthesized according to previously published procedures (Newkome et al., *Chem. Rev.* 110:6338-42 (2010), which is hereby incorporated by reference in its entirety). Dendrons were coupled to the avobenzone moiety using carbodiimide/DIPEA peptide-coupling schemes (Newkome et al., *Chem. Rev.* 110:6338-42 (2010), which is hereby incorporated by reference in its entirety). The dendrimers conjugates were characterized using $^1$H NMR and $^{13}$C NMR spectroscopies, and mass spectrometry. The G0 Newkome-type dendrimer conjugate was isolated in 22.4% yield with full conversion. The G1 Newkome type conjugate was isolated in 13.6% yield with full conversion. The G2 Newkome type conjugate was isolated in 13.5% yield with full conversion. The G2 PAMAM conjugate was isolated in 37.8% yield with full conversion. The G3 PAMAM conjugate was isolated in 31.6% yield with 87.5%-96.8% avobenzone moieties.

UV analysis was run on each conjugate to test the absorbance and degradation profile of each compound. The linker and scaffold must not shift the UV absorbance profile of the avobenzone if it is to be used as an additive in sunscreen formulations. Otherwise, it might no longer be active as a UV-A filter. UV calibrations were run for free avobenzone, avobenzone with linker, and each class and generation of dendrimer-avobenzone conjugate to compare the modified molecules to the original under the same conditions.

The molar attenuation coefficient for each compound was calculated at 357 nM, the absorption maximum in the UVA-1 range. Modification at the carbon alpha to the carbonyls does not result in a shift in the UV spectrum. Additionally, no shift was observed after ligation to the dendrimer scaffolds. Molar attenuation coefficients of each compound, corresponding the absorbance at 357 nM, remained on the same order of magnitude and the system was tested for stability over time during exposure to UV irradiation.

Extinction coefficient curves were taken in isopropanol, a protic solvent known to stabilize avobenzone under UV irradiation, allowing the curve to be run on a single sample of avobenzone per curve without loss of activity (Mturi et al., *J. Phoochem. Pholobiol.* 200:410-20 (2008), which is hereby incorporated by reference in its entirety). The molar attenuation coefficient of bare avobenzone was found to be 1,039 $M^{-1}$ $cm^{-1}$. The addition of the avobenzone with linker was found to have a molar attenuation coefficient of 2,899 $M^{-1}$ $cm^{-1}$. This increased absorptivity indicated that modifications at the alpha carbons do not negatively affect the UV properties of avobenzone.

The ligation to various dendrimers was not found to negatively impact the molar attenuation coefficient and was calculated for moles of the dendrimer as well as for each avobenzone on the scaffold. The G0 Newkome-type dendrimer was found to have a molar attenuation coefficient of 3,473 $M^{-1}$ $cm^{-1}$ for the conjugate and, with two avobenzones per scaffold, the molar attenuation coefficient per avobenzone was found to be 1,871 $M^{-1}cm^{-1}$. The G1 Newkome-type dendrimer was found to have a molar attenuation coefficient of 2, 6142 $M^{-1}cm^{-1}$ for the conjugate and, with six avobenzones per scaffold, the molar attenuation coefficient per avobenzone was found to be 4,357 $M^{-1}cm^{-1}$. The G2 Newkome-type dendrimer was found to have a molar attenuation coefficient of 45,895 $M^{-1}cm^{-1}$ for the conjugate and, with eighteen avobenzones per scaffold, the molar attenuation coefficient per avobenzone was found to be 2,549 $M^{-1}cm^{-1}$. The G2 PAMAM dendrimer was found to have a molar attenuation coefficient of 29,941 $M^{-1}$ $cm^{-1}$ for the conjugate and, with sixteen avobenzones per scaffold, the molar attenuation coefficient per avobenzone was found to be 1,871 $M^{-1}cm^{-1}$. The G3 PAMAM dendrimer was found to have a molar attenuation coefficient of 78,032 $M^{-1}$ $cm^{-1}$ for the conjugate and, with thirty-two avobenzones per scaffold, the molar attenuation coefficient per avobenzone was found to be 2,438 $M^{-1}cm^{-1}$.

UV stability experiments were run in triplicate in ethyl acetate (Mturi et al., *J. Photochem. Photobiol.* 200:410-20 (2008), which is hereby incorporated by reference in its entirety). Unlike isopropanol, this solvent is known to encourage degradation and was chosen so that the experimental time scales would be similar to the time scale of sun exposure in vivo. Due to FDA regulations, all commercial sunscreens are labeled with instructions to reapply every two hours. The avobenzone systems were tested over four hours, double that time. The avobenzone, avobenzone linker, or avobenzone-dendrimer conjugate was dissolved in a small amount of isopropanol. In each study 90 μL of the stock solution was added to 3 mL of ethyl acetate and sealed in an airtight quartz cuvette.

The initial absorptions were measured and the samples were sealed in quartz cuvettes and left under a UV lamp emitting at 365 nM. The absorption profile was measured at regular intervals. The maximum of the peak at 357 nM (or in the case of a shift in absorption the peak closest to 357 nM) was used to calculate degradation and in each case except for the G0 dendrimer the peak did not shift over the course of four hours. The initial absorbance was normalized to 1 and degradation or increase in activity was measured as the change from this absorbance over time.

Figure 3:
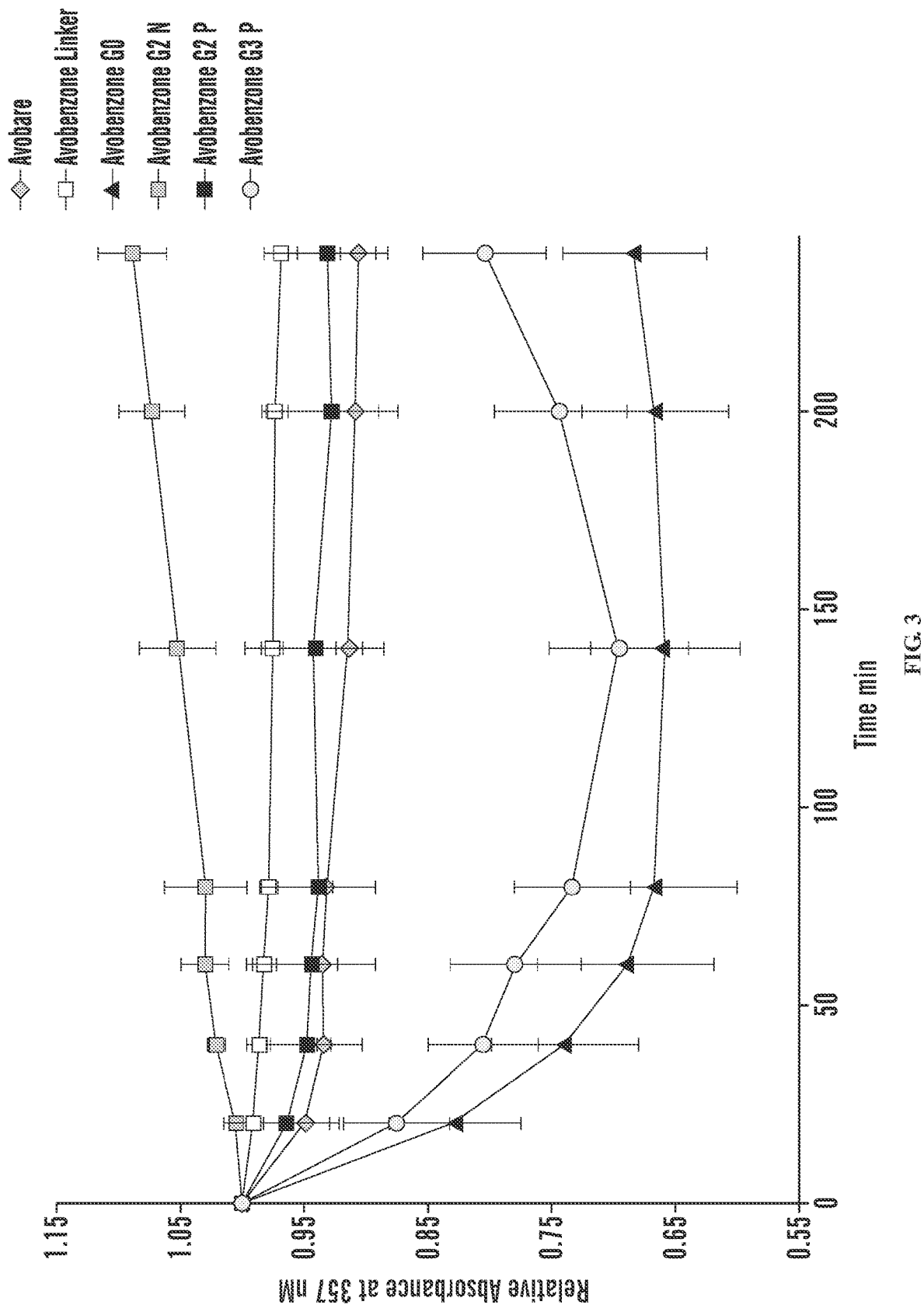
FIG. 3 is the graph showing results of the stability experiments for avobenzone conjugates, excluding G1, over time: bare avobenzone (pink, "Avobare"); avobenzone with linker (dark blue, "Avobenzone Linker"); G0 avobenzone (green, "Avobenzone G0"); G2 Newkome-type avobenzone in ethyl acetate (light blue, "Avobenzone G2 N"); G2 PAMAM avobenzone in ethyl acetate (purple, "Avobenzone G2 P"); G3 PAMAM in avobenzone (orange, "Avobenzone G3 P"). (The color of the lines in the graph of FIG. 3 are, from top to bottom: dark blue, light blue, purple, pink, orange, green.)

Over the course of the stability experiments several trends emerged (FIG. 3). The bare avobenzone was found to degrade over time with a large initial drop in absorbance and over four hours was found to be on average 90.7±1.4% as active as its initial absorbance. The avobenzone is expected to degrade and the dendrimer conjugate must be more stable than the avobenzone for it to be advantageous to sun care. The avobenzone with linker was found to be increasingly active over time under UV exposure with final absorbance on average 108±1.8% of the initial absorbance. This increase in activity is promising as there is no shift in the maximum absorbance and the compound exhibits increased stability compared to bare avobenzone.

The G0 avobenzone conjugate was the least photostable; in addition to a shift in absorbance maximum from 347 to 357, the final absorbance was on average 68±5.8% that of the initial absorbance (FIG. 3). This disqualifies the G0 as a potential sunscreen additive.

Figure 4:
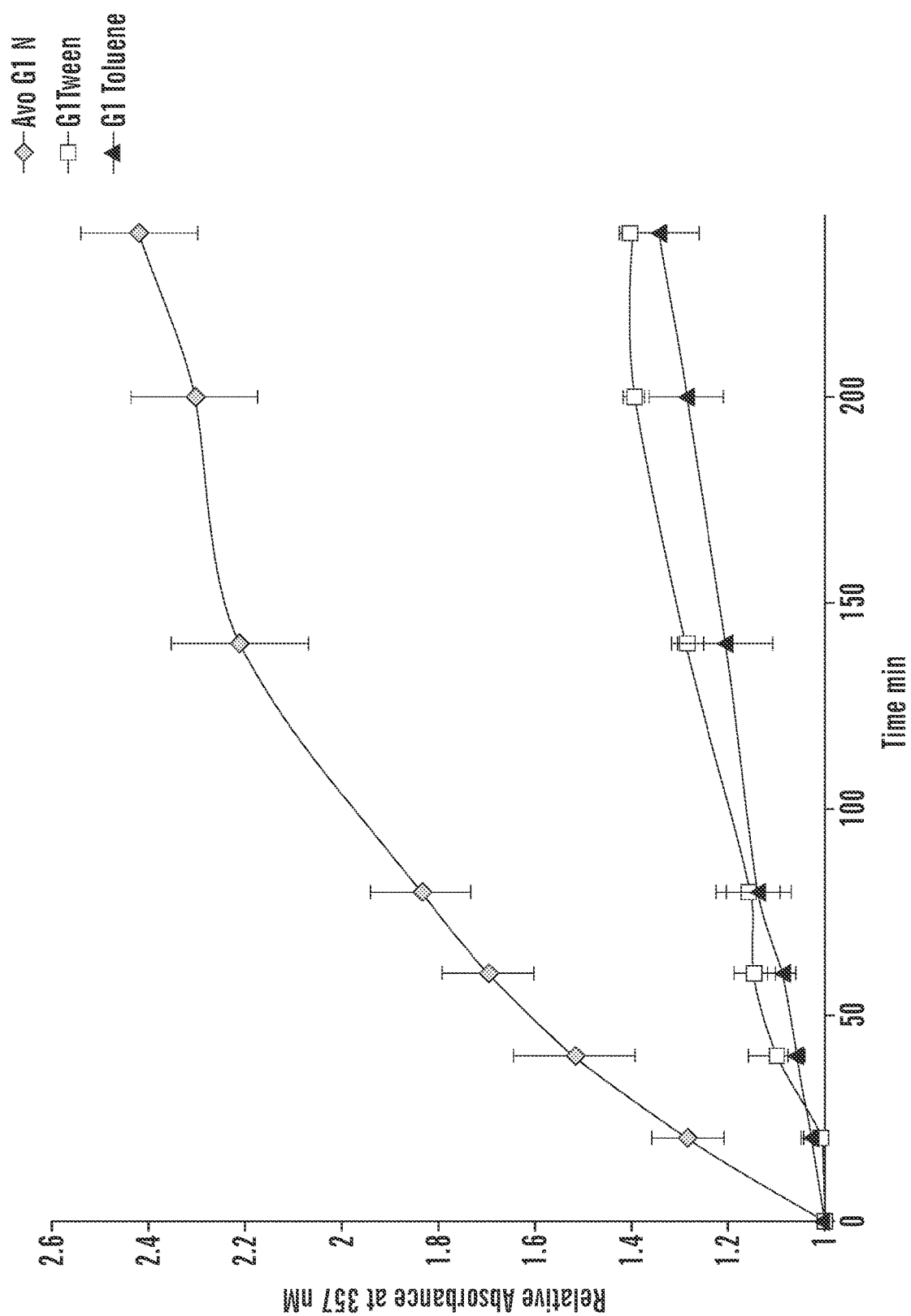
FIG. 4 is the graph showing relative absorbance of G1 Newkome-type dendrimer Avobenzone conjugate over time in: ethyl acetate (red, "Avo G1 N"); ethyl acetate with TWEEN® (pink, "G1Tween"); and toluene (burgundy, "G1 Toluene"). (The color of the lines in the graph of FIG. 4 are, from top to bottom: red, pink, burgundy.)

The G1 Newkome-type avobenzone dendrimer conjugate showed the most promise as the UV absorbance after four hours in ethyl acetate was on average 242±11% as active as the initial absorbance (FIG. 4). To further investigate this phenomenon and rule out aggregation as a possible reason for the increase in absorbance, the experiment was repeated in duplicate in ethyl acetate with 1% TWEEN®, a non ionic and UV inactive surfactant which is approved for use in cosmetics. The final absorbance with surfactant was found to be on average 1402.1% of the initial absorbance. Finally the G1 dendrimer was rerun in duplicate in toluene and the final absorbance was found to be 134±7.6% the initial absorbance. Together these studies suggest that the G1 dendrimer is able to stabilize the photoactive isomer of avobenzone.

The G2 Newkome-type dendrimer conjugate showed stabilization comparable to the free avobenzone with a final absorbance of 96.92.7% of the original activity (FIG. 3). This generation is significantly less stabilizing but presents the opportunity for better film formation due to the increased size of the dendrimer.

The G2 PAMAM and G3 PAMAM dendrimer conjugates were tested for their ability to stabilize avobenzone. The G2 PAMAM dendrimer showed a greater initial drop in absorbance compared to avobenzone but over four hours recovered activity such that the final absorbance was 90.84.9% of the initial absorbance (FIG. 3). This dendrimer provides no advantage over free avobenzone with respect to stability. The G3 PAMAM dendrimers show a similar shaped curve to the G2 PAMAM dendrimer with a sharp loss in absorbance and a recovery of activity. Despite the recovery, the final absorbance is 80.4±5.6% of the initial absorbance (FIG. 3). Neither PAMAM dendrimer was therefore suitable to stabilize avobenzone. G2 PAMAM, however, was found to increase the molar attenuation coefficient per avobenzone without decreasing stability and, thus, would still be an acceptable substitute for bare avobenzone.

Of every dendrimer tested, the most promising generation was the G1 Newkome-type dendrimer. Over the four-hour experiment not only did the absorbance at 357 consistently become more active but also the absorbance between 290 and 270 nM consistently decreased suggesting a decrease in the diketo-species. In studies of pure avobenzone in the literature this trend is inverted and represents the breakdown of avobenzone in solution. Previous work with avobenzone has shown that as the molecule undergoes photoisomerization, the absorbance at 357 nM decreases and the absorbance at 270 nM increases. The implication from the data on the first generation Newkome dendrimer is that the more active conformation is stabilized in solution. This stabilization of the most active photoisomer presents a unique new opportunity to use dendrimers to not only stabilize avobenzone but, in an optimal system, enhances the activity of avobenzone in solution.

The results presented herein demonstrate that a polymer support can significantly stabilize avobenzone. This stabilization increases the lifespan of avobenzone and, ultimately, its efficacy in formulation for sun screen. Polymers already have widespread use in cosmetics and dendrimers have been shown to be safe in a variety of formulations. These Newkome-type dendrimer avobenzone conjugates expand the possible applications of dendrimers and demonstrate the range of activity possible within one class of scaffold and the potential for optimization of a polymer system for stabilization of a reactive molecule.

Through the exploration of ligation of avobenzone to several PAMAM and Newkome-type dendrimers, an optimal dendrimer backbone and generation was found. The increase in activity over time of the G1 avobenzone conjugate is indicative of the dendrimer's ability to prevent photobleaching of an important UV filter.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An avobenzone-dendrimer conjugate comprising: a polyamide dendrimer conjugated with 1 to 18 units of avobenzone.

2. The avobenzone-dendrimer conjugate according to claim 1, wherein the avobenzone-dendrimer conjugate has a formula selected from the group consisting of:

(a) Formula IA:

$$[B \dash_3 A \dash B]_3 \qquad \qquad IA,$$

wherein:

A is an amide dendrimer core;

each B is, independently, a moiety of formula

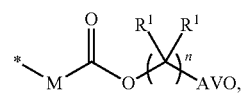

wherein:

\*- is the point of attachment to A;

M is optionally present and, if present, is an aromatic or aliphatic moiety;

each $R^1$ is selected from the group consisting of H and $C_{1-3}$ alkyl;

each AVO is, independently, a capping group or avobenzone, wherein at least one AVO is avobenzone; and n is an integer from 1 to 30; and (b) Formula IB:

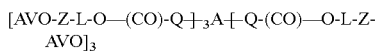  IB, wherein:

A is an amide dendrimer core;

Q is optionally present and, if present, is an aromatic or aliphatic moiety;

each L is a linker;

each Z is optionally present and, if present, is a spacer; and each AVO is, independently, a capping group or avobenzone.

3. The avobenzone-dendrimer conjugate according to claim 1, wherein the avobenzone-dendrimer conjugate has a formula of Formula II:

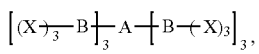  II wherein:

A is an amide dendrimer core;

each B is, independently, a moiety of formula

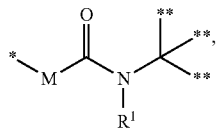

wherein:

*- is the point of attachment to A;

** is the point of attachment to X;

M is an aromatic or aliphatic moiety; and each $R^1$ is selected from the group consisting of H and $C_{1-3}$ alkyl; and each X is, independently, a moiety of formula ***-Q-(CO)—O-L-Z-AVO, wherein:

***- is the point of attachment to B;

Q is optionally present and, if present, is an aromatic or aliphatic moiety;

each L is a linker;

each Z is optionally present and, if present, is a spacer; and each AVO is, independently, a capping group or avobenzone.

4. The avobenzone-dendrimer conjugate according to claim 1, wherein the avobenzone-dendrimer conjugate has a formula of Formula III:

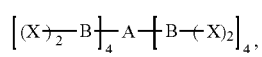  III wherein:

A is an amide dendrimer core;

each B is, independently, a moiety of formula

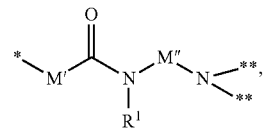

wherein:

*- is the point of attachment to A;

** is the point of attachment to X;

each M' and M" are, independently, an aromatic or aliphatic moiety; and each $R^1$ is selected from the group consisting of H and $C_{1-3}$ alkyl; and each X is, independently, a moiety of formula ***-Q-(CO)—O-L-Z-AVO, wherein:

***- is the point of attachment to B;

Q is optionally present and, if present, is an aromatic or aliphatic moiety;

each L is a linker;

each Z is optionally present and, if present, is a spacer; and each AVO is, independently, a capping group or avobenzone.

5. A sunscreen formulation comprising:

an avobenzone-dendrimer conjugate according to claim 1 and a dermatologically acceptable vehicle.

* * * * *

UNITED STATES PATENT AND TRADEMARK OFFICE
CERTIFICATE OF CORRECTION

PATENT NO. : 11,291,620 B2
APPLICATION NO. : 16/977340
DATED : April 5, 2022
INVENTOR(S) : Weck and Kaufman It is certified that error appears in the above-identified patent and that said Letters Patent is hereby corrected as shown below:

In the Claims

At Claim 2, Column 62, Line 49 (Formula IA), delete "[B┤₃A├B]₃" and insert --[B├₃A┤B]₃-- in its place.

At Claim 2, Column 63, Lines 8-9 (Formula IB), delete "[AVO-Z-L-O—(CO)-Q┤₃A├Q-(CO)—O-L-Z-AVO]₃" and insert --[AVO-Z-L-O-(CO)-Q├₃A┤Q-(CO)-O-L-Z-AVO]₃-- in its place.

At Claim 3, Column 64, Lines 1-2, delete "*-Q-(CO)—O-L-Z-AVO" and insert --*—Q–(CO)–O–L–Z–AVO-- in its place.

At Claim 4, Column 64, Lines 37-38, delete "*-Q-(CO)—O-L-Z-AVO" and insert --*—Q–(CO)–O–L–Z–AVO-- in its place.

Signed and Sealed this
Twenty-ninth Day of November, 2022

Katherine Kelly Vidal
*Director of the United States Patent and Trademark Office*